United States Patent
Glass et al.

(10) Patent No.: US 11,668,051 B2
(45) Date of Patent: *Jun. 6, 2023

(54) SANITARY TISSUE PRODUCT WITH A SHAPED LINE OF WEAKNESS

(71) Applicant: The Procter & Gamble Company, Cincinnati, OH (US)

(72) Inventors: Katie Kristine Glass, Maineville, OH (US); Angela Marie Leimbach, Hamilton, OH (US); Gustav Andre Mellin, Amberley Village, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 119 days.

This patent is subject to a terminal disclaimer.

(21) Appl. No.: 17/186,031

(22) Filed: Feb. 26, 2021

(65) Prior Publication Data
US 2021/0180258 A1 Jun. 17, 2021

Related U.S. Application Data

(63) Continuation of application No. 16/127,519, filed on Sep. 11, 2018, now Pat. No. 10,947,671.
(Continued)

(51) Int. Cl.
*D21H 25/00* (2006.01)
*B26F 1/14* (2006.01)
(Continued)

(52) U.S. Cl.
CPC ........... *D21H 25/005* (2013.01); *B26D 1/085* (2013.01); *B26D 1/385* (2013.01); *B26D 3/10* (2013.01);
(Continued)

(58) Field of Classification Search
CPC .... D21H 25/005; D21H 27/002; D21H 27/02; D21H 27/004; D21H 27/005; B26F 1/20;
(Continued)

(56) References Cited

U.S. PATENT DOCUMENTS

D17,308 S    5/1887  Kelsey
405,412 A    6/1889  Hicks
(Continued)

FOREIGN PATENT DOCUMENTS

CA    2373812 A1    1/2001
CA    3072361 A1 *  3/2019  ............. B26D 1/085
(Continued)

OTHER PUBLICATIONS

Unpublished U.S. Appl. No. 17/182,312, filed Feb. 23, 2021, to Kathryn Christian Kie et al.
(Continued)

*Primary Examiner* — Jose A Fortuna
(74) *Attorney, Agent, or Firm* — Richard L. Alexander; Andrew J. Mueller

(57) ABSTRACT

A web of sanitary tissue of the present disclosure may comprise a shaped line of weakness, wherein the toilet tissue exhibits a Line of Weakness Performance Factor (LWP Factor) of from about 7 to about 30, and a Full Sheet Average Trapezoidal Tear Strength of between about 8 g and about 20 g according to the Full Sheet Average Trapezoidal Tear Force Test Method.

20 Claims, 17 Drawing Sheets

Related U.S. Application Data

(60) Provisional application No. 62/556,720, filed on Sep. 11, 2017.

(51) Int. Cl.

| | | |
|---|---|---|
| *B26D 3/10* | (2006.01) | |
| *D21H 27/00* | (2006.01) | |
| *A47K 10/16* | (2006.01) | |
| *A61K 8/02* | (2006.01) | |
| *B26D 1/08* | (2006.01) | |
| *B26D 7/20* | (2006.01) | |
| *B26D 1/38* | (2006.01) | |
| *B26F 1/38* | (2006.01) | |
| *B26F 1/44* | (2006.01) | |
| *D21F 11/00* | (2006.01) | |
| *B26F 1/20* | (2006.01) | |

(52) U.S. Cl.
CPC .............. *B26D 7/204* (2013.01); *B26F 1/14* (2013.01); *B26F 1/384* (2013.01); *B26F 1/44* (2013.01); *D21F 11/008* (2013.01); *D21H 27/004* (2013.01); *D21H 27/005* (2013.01); *A47K 10/16* (2013.01); *A61K 8/0208* (2013.01); *B26F 1/20* (2013.01); *B26F 2001/4472* (2013.01); *D21F 11/006* (2013.01)

(58) Field of Classification Search
CPC .... B26F 1/22; B26F 1/384; B26F 2001/4472; B26F 1/14; B26F 1/44; B26D 1/385; B26D 7/204; B26D 1/085; B26D 3/10; A47K 10/16; B65H 2301/5152; A61K 8/0208; D21F 11/006; D21F 11/008; Y10T 428/15; Y10T 428/24273
See application file for complete search history.

(56) References Cited

U.S. PATENT DOCUMENTS

| | | |
|---|---|---|
| 714,652 A | 11/1902 | David |
| 1,383,868 A | 7/1921 | Smith |
| 2,007,544 A | 7/1935 | Meisel |
| 2,007,731 A | 7/1935 | Tomlin |
| 2,328,109 A | 8/1943 | Thompson |
| 2,588,581 A | 3/1952 | Sieger |
| 2,744,624 A | 5/1956 | Hoogstoel et al. |
| 2,805,715 A | 9/1957 | Abraham |
| D819,983 S | 3/1961 | Krause |
| 3,190,163 A | 6/1965 | Bradley |
| 3,228,274 A | 1/1966 | George |
| 3,264,921 A | 8/1966 | Daniel |
| 3,321,145 A | 5/1967 | Gorman |
| 3,323,269 A | 6/1967 | Widdowson |
| 3,467,250 A | 9/1969 | D'Elia et al. |
| 3,583,558 A | 6/1971 | Davis |
| 3,716,132 A | 2/1973 | Lewyckyj |
| 3,733,949 A | 5/1973 | Bradley |
| 3,752,304 A | 8/1973 | Alef |
| 3,762,542 A | 10/1973 | Grimes |
| 3,769,868 A | 11/1973 | Hornung |
| 3,770,172 A | 11/1973 | Nystrand et al. |
| 3,779,123 A | 12/1973 | Chafee |
| 3,931,886 A | 1/1976 | Yamauchi |
| 4,034,637 A | 7/1977 | Ollery |
| 4,044,641 A | 8/1977 | Burt, Jr. |
| 4,164,329 A | 8/1979 | Higby |
| 4,199,090 A | 4/1980 | Reed |
| 4,210,688 A | 7/1980 | Sato |
| 4,244,251 A | 1/1981 | Iwao |
| 4,452,114 A | 6/1984 | Rynik et al. |
| 4,457,964 A | 7/1984 | Kaminstein |
| 4,610,189 A | 9/1986 | Lombardo |
| 4,747,364 A | 5/1988 | Horowitz |
| 4,759,247 A | 7/1988 | Bell et al. |
| 4,884,719 A | 12/1989 | Levine et al. |
| 5,041,317 A | 8/1991 | Greyvenstein |
| 5,048,387 A | 9/1991 | Niitsuma et al. |
| 5,114,771 A | 5/1992 | Ogg et al. |
| 5,117,718 A | 6/1992 | Wittkopf |
| 5,125,302 A | 6/1992 | Biagiotti |
| 5,205,454 A | 4/1993 | Schutz et al. |
| 5,246,110 A | 9/1993 | Greyvenstein |
| 5,284,304 A | 2/1994 | Biagiotti |
| 5,344,091 A | 9/1994 | Molison |
| 5,445,054 A | 8/1995 | Pryor |
| 5,453,311 A | 9/1995 | Svensson |
| D175,829 S | 10/1995 | Fitzpatrick |
| D368,775 S | 4/1996 | Gobran |
| 5,562,964 A | 10/1996 | Jones |
| 5,613,347 A | 3/1997 | Weder |
| 5,616,387 A | 4/1997 | Augst et al. |
| D385,910 S | 11/1997 | Hansen |
| 5,704,566 A | 1/1998 | Schulz et al. |
| 5,740,657 A | 4/1998 | Weder |
| 5,740,658 A | 4/1998 | Weder |
| D393,950 S | 5/1998 | Alutsu |
| 5,755,654 A | 5/1998 | Schulz |
| 5,789,050 A | 8/1998 | Kang |
| 5,797,305 A | 8/1998 | Harrod et al. |
| 5,806,399 A | 9/1998 | Oechsner |
| 5,853,117 A | 12/1998 | Traise |
| D405,466 S | 2/1999 | Hansen |
| D410,950 S | 6/1999 | Kraus et al. |
| D413,351 S | 8/1999 | Escobedo et al. |
| D414,510 S | 9/1999 | Kraus et al. |
| 6,092,354 A | 7/2000 | Takahashi |
| 6,139,186 A | 10/2000 | Fraser |
| 6,029,921 A | 12/2000 | Johnson |
| 6,228,454 B1 | 5/2001 | Johnson et al. |
| 6,276,032 B1 | 8/2001 | Nortman et al. |
| D456,837 S | 5/2002 | Leon |
| D457,913 S | 5/2002 | Leon |
| 6,431,491 B1 | 8/2002 | Biagiotti |
| 6,447,864 B2 | 9/2002 | Johnson et al. |
| 6,460,727 B1 | 10/2002 | Irwin |
| 6,464,120 B1 | 10/2002 | Johnson et al. |
| D466,152 S | 11/2002 | Leon |
| 6,536,624 B2 | 3/2003 | Johnson et al. |
| 6,565,794 B1 | 5/2003 | Fraser |
| D483,120 S | 12/2003 | Klebba et al. |
| D483,486 S | 12/2003 | Klebba et al. |
| D483,867 S | 12/2003 | Klebba et al. |
| 6,698,323 B2 | 3/2004 | Forman et al. |
| D489,450 S | 5/2004 | Wu et al. |
| 6,694,535 B1 | 12/2004 | Gschwind |
| 6,838,040 B2 | 1/2005 | Mlinar et al. |
| 6,877,689 B2 | 4/2005 | Butterworth |
| D527,102 S | 8/2006 | Mills et al. |
| D527,818 S | 9/2006 | Mills et al. |
| 7,195,810 B1 | 3/2007 | Schmidt et al. |
| D544,960 S | 6/2007 | Schroer, Jr. |
| D550,367 S | 9/2007 | Nash |
| D560,070 S | 1/2008 | Fujimoto et al. |
| D562,461 S | 2/2008 | Nash |
| D573,763 S | 7/2008 | Policicchio et al. |
| D589,264 S | 3/2009 | Hanafusa |
| D599,013 S | 8/2009 | Johnson et al. |
| 7,707,661 B2 | 5/2010 | Issachar |
| 7,971,514 B2 | 7/2011 | Alalu |
| 7,988,607 B2 | 8/2011 | Baggot et al. |
| 8,277,917 B2 | 2/2012 | Neto et al. |
| 8,166,857 B2 | 5/2012 | Powell et al. |
| 8,268,429 B2 | 9/2012 | McNeil et al. |
| 8,283,013 B2 | 10/2012 | Feldmann et al. |
| 8,287,976 B2 | 10/2012 | Hupp |
| 8,287,977 B2 | 10/2012 | McNeil et al. |
| 8,312,797 B2 | 11/2012 | Hsu |
| 8,353,236 B2 | 1/2013 | Marco |
| 8,443,725 B2 | 5/2013 | McNeil et al. |
| 8,448,816 B2 | 5/2013 | Gordon |
| 8,468,938 B2 | 6/2013 | Redd |
| 8,535,483 B2 | 9/2013 | McNeil et al. |

(56) References Cited

U.S. PATENT DOCUMENTS

| | | | |
|---|---|---|---|
| 8,539,867 B2 | 9/2013 | Powell et al. | |
| 8,621,966 B2 | 1/2014 | Germaine et al. | |
| 8,757,058 B2 | 6/2014 | Kien et al. | |
| 8,763,523 B2 | 7/2014 | McNeil et al. | |
| 8,763,526 B2 | 7/2014 | McNeil et al. | |
| 8,802,211 B2 | 8/2014 | Cattacin et al. | |
| 8,947,626 B2 | 2/2015 | Iwamoto | |
| 9,195,861 B2 | 11/2015 | Bigari et al. | |
| 9,259,848 B2 | 2/2016 | Hupp et al. | |
| 9,409,372 B2 | 8/2016 | Hada et al. | |
| 9,486,932 B2 | 11/2016 | Baggot et al. | |
| 9,539,735 B2 | 1/2017 | Ferguson | |
| 9,592,621 B2 | 3/2017 | Demarco et al. | |
| 9,914,234 B2 | 3/2018 | Baggot et al. | |
| 9,918,595 B2 | 3/2018 | Olson et al. | |
| 9,918,596 B2 | 3/2018 | Olson et al. | |
| 9,950,892 B2 | 4/2018 | Slovut et al. | |
| D817,009 S | 5/2018 | Nelson et al. | |
| 10,005,197 B2 | 6/2018 | Kien et al. | |
| 10,188,242 B2 | 1/2019 | Olson et al. | |
| 10,232,524 B2 | 3/2019 | Slovut et al. | |
| 10,293,510 B2 | 5/2019 | Slovut et al. | |
| D859,005 S | 9/2019 | Schuh et al. | |
| 10,524,622 B2 | 1/2020 | Olson et al. | |
| D876,109 S | 2/2020 | Hood | |
| D895,731 S | 9/2020 | Schwab et al. | |
| 10,814,513 B2 | 10/2020 | Kien et al. | |
| 10,857,690 B2 | 12/2020 | Schwamberger et al. | |
| 10,919,168 B2 | 2/2021 | Slovut et al. | |
| 10,947,671 B2* | 3/2021 | Glass | B26D 3/10 |
| 10,960,566 B2 | 3/2021 | Slovut et al. | |
| 11,008,709 B2* | 5/2021 | Glass | D21H 27/004 |
| 11,008,710 B2* | 5/2021 | Glass | B26F 1/14 |
| 11,180,892 B2* | 11/2021 | Glass | D21F 11/008 |
| 11,268,243 B2* | 3/2022 | Glass | D21F 11/008 |
| 2001/0000737 A1 | 5/2001 | Johnson et al. | |
| 2002/0062117 A1 | 5/2002 | Raufman | |
| 2002/0155246 A1 | 10/2002 | Johnson et al. | |
| 2003/0000357 A1 | 1/2003 | Tanaka | |
| 2003/0033914 A1 | 2/2003 | Mutchnik et al. | |
| 2003/0106405 A1 | 6/2003 | Hartmann et al. | |
| 2003/0132549 A1 | 7/2003 | Mlinar et al. | |
| 2003/0172785 A1 | 9/2003 | Formon et al. | |
| 2003/0218040 A1 | 11/2003 | Faulks et al. | |
| 2003/0226431 A1 | 12/2003 | Motard | |
| 2004/0003699 A1 | 1/2004 | Welch | |
| 2004/0064911 A1 | 4/2004 | Klupfel et al. | |
| 2004/0159693 A1 | 8/2004 | Adachi et al. | |
| 2004/0182213 A1 | 9/2004 | Wagner | |
| 2004/0188556 A1 | 9/2004 | Jong | |
| 2004/0244556 A1 | 12/2004 | Neal | |
| 2005/0100715 A1 | 5/2005 | Bredahl et al. | |
| 2005/0115372 A1 | 6/2005 | Cavlin | |
| 2005/0155478 A1 | 7/2005 | Zimmer | |
| 2006/0011030 A1 | 1/2006 | Wagner et al. | |
| 2007/0000364 A1 | 1/2007 | Powell et al. | |
| 2007/0014961 A1 | 1/2007 | Schneider et al. | |
| 2007/0023135 A1 | 2/2007 | Giacometti | |
| 2007/0044613 A1 | 3/2007 | Cohen | |
| 2007/0144324 A1 | 6/2007 | Robert et al. | |
| 2007/0209099 A1 | 9/2007 | Issachar | |
| 2008/0028902 A1 | 2/2008 | Baggot et al. | |
| 2008/0280088 A1 | 11/2008 | Baum | |
| 2009/0212153 A1 | 8/2009 | Alalu | |
| 2009/0235800 A1 | 9/2009 | Germaine et al. | |
| 2010/0112264 A1 | 5/2010 | Barredo | |
| 2010/0167896 A1 | 7/2010 | Hasa et al. | |
| 2010/0199822 A1 | 8/2010 | DeMarco et al. | |
| 2010/0242698 A1 | 9/2010 | Hsu | |
| 2010/0243780 A1 | 9/2010 | Neto | |
| 2010/0264159 A1 | 10/2010 | Gordon | |
| 2010/0309544 A1 | 12/2010 | Nomura et al. | |
| 2011/0192263 A1 | 8/2011 | De Marco et al. | |
| 2011/0290920 A1 | 12/2011 | Kim et al. | |
| 2011/0308363 A1 | 12/2011 | Kien et al. | |
| 2011/0308366 A1 | 12/2011 | Redd | |
| 2011/0308370 A1 | 12/2011 | Hupp et al. | |
| 2011/0308372 A1 | 12/2011 | McNeil et al. | |
| 2011/0308405 A1 | 12/2011 | McNeil et al. | |
| 2011/0308406 A1 | 12/2011 | McNeil et al. | |
| 2011/0308754 A1 | 12/2011 | McNeil et al. | |
| 2011/0311748 A1 | 12/2011 | Hupp | |
| 2011/0311749 A1 | 12/2011 | McNeil et al. | |
| 2011/0311750 A1 | 12/2011 | McNeil et al. | |
| 2011/0311751 A1 | 12/2011 | Feldmann et al. | |
| 2012/0111166 A1 | 5/2012 | Yamada et al. | |
| 2012/0174720 A1 | 7/2012 | Powell et al. | |
| 2012/0198979 A1 | 8/2012 | Ohsawa | |
| 2012/0216663 A1 | 8/2012 | Carmichael | |
| 2012/0234145 A1 | 9/2012 | Kandemir | |
| 2012/0234152 A1 | 9/2012 | Carmichael | |
| 2012/0245011 A1 | 9/2012 | De Matteis | |
| 2013/0036884 A1 | 2/2013 | Schurch et al. | |
| 2013/0049438 A1 | 2/2013 | Nootbaar et al. | |
| 2013/0294808 A1 | 11/2013 | Douillard et al. | |
| 2014/0174270 A1 | 6/2014 | Demarco et al. | |
| 2014/0238210 A1 | 8/2014 | Baggot et al. | |
| 2014/0344702 A1 | 11/2014 | Edge et al. | |
| 2014/0346704 A1 | 11/2014 | Sartini et al. | |
| 2014/0366695 A1 | 12/2014 | Kien et al. | |
| 2014/0366702 A1 | 12/2014 | Kien et al. | |
| 2014/0370224 A1 | 12/2014 | Kien et al. | |
| 2015/0135925 A1 | 5/2015 | Abrahams | |
| 2015/0176218 A1 | 6/2015 | Maladen et al. | |
| 2015/0298340 A1 | 10/2015 | Baggot et al. | |
| 2016/0121501 A1 | 5/2016 | Baggot et al. | |
| 2016/0144525 A1 | 5/2016 | Kenmotsu et al. | |
| 2016/0271820 A1 | 9/2016 | Slovut et al. | |
| 2016/0271823 A1 | 9/2016 | Slovut et al. | |
| 2016/0271824 A1 | 9/2016 | Slovut et al. | |
| 2016/0345761 A1 | 12/2016 | Olson et al. | |
| 2016/0345786 A1 | 12/2016 | Olson et al. | |
| 2017/0280946 A1 | 10/2017 | Weisang et al. | |
| 2018/0132674 A1 | 5/2018 | Olson et al. | |
| 2018/0199766 A1 | 7/2018 | Olson et al. | |
| 2018/0201464 A1 | 7/2018 | Slovut et al. | |
| 2018/0264676 A1 | 9/2018 | Kien et al. | |
| 2018/0361606 A1 | 12/2018 | Banowetz et al. | |
| 2019/0077038 A1 | 3/2019 | Glass et al. | |
| 2019/0077039 A1 | 3/2019 | Glass et al. | |
| 2019/0078263 A1* | 3/2019 | Glass | B26D 3/10 |
| 2019/0078264 A1* | 3/2019 | Glass | D21H 27/005 |
| 2019/0078265 A1* | 3/2019 | Glass | D21H 27/004 |
| 2019/0078266 A1* | 3/2019 | Glass | D21F 11/008 |
| 2019/0078267 A1* | 3/2019 | Glass | B26D 1/085 |
| 2019/0125139 A1 | 5/2019 | Olson et al. | |
| 2019/0152081 A1 | 5/2019 | Slovut et al. | |
| 2020/0078976 A1 | 3/2020 | Schwamberger et al. | |
| 2020/0085246 A1 | 3/2020 | Olson et al. | |
| 2020/0094998 A1* | 3/2020 | Horz | B65B 7/2807 |
| 2020/0214511 A1 | 7/2020 | Olson et al. | |
| 2020/0290792 A1* | 9/2020 | Yasui | D21H 17/72 |
| 2021/0060809 A1 | 3/2021 | Schwamberger et al. | |
| 2021/0101772 A1 | 4/2021 | Slovut et al. | |
| 2021/0180258 A1* | 6/2021 | Glass | B26D 3/10 |
| 2021/0317613 A1* | 10/2021 | Glass | D21F 11/008 |

FOREIGN PATENT DOCUMENTS

| | | | |
|---|---|---|---|
| CA | 3072516 A1 * | 3/2019 | B26D 1/085 |
| CA | 3072603 A1 * | 3/2019 | B26D 1/085 |
| CA | 3072779 A1 * | 3/2019 | B26D 1/085 |
| DE | 1090069 | 9/1960 | |
| DE | 1112881 B | 8/1961 | |
| DE | 1291188 | 3/1969 | |
| DE | 2706234 | 8/1978 | |
| DE | 10356037 | 7/2005 | |
| DE | 202005017013 | 1/2006 | |
| DE | 102005041180 | 3/2007 | |
| EP | 1010503 | 6/2000 | |
| FR | 2161144 | 7/1973 | |
| FR | 2377471 | 8/1978 | |
| GB | 808244 | 1/1959 | |
| GB | 923029 A | 4/1963 | |

(56) References Cited

FOREIGN PATENT DOCUMENTS

| | | | | |
|---|---|---|---|---|
| GB | 2488782 | 9/2012 | | |
| JP | H 0884685 | 4/1996 | | |
| JP | 2005153997 | 6/2005 | | |
| JP | 2005296588 | 10/2005 | | |
| JP | 2007117366 | 5/2007 | | |
| WO | WO 9002639 | 3/1990 | | |
| WO | WO 9723398 | 7/1997 | | |
| WO | WO 9825738 | 6/1998 | | |
| WO | WO 02100614 | 12/2002 | | |
| WO | WO-2019051458 A1 | * | 3/2019 | ............. B26D 1/085 |
| WO | WO-2019051459 A1 | * | 3/2019 | ............. B26D 1/085 |
| WO | WO-2019051460 A1 | * | 3/2019 | ............. B26D 1/085 |
| WO | WO-2019051461 A1 | * | 3/2019 | ............. B26D 1/085 |
| WO | WO-2019051462 A1 | * | 3/2019 | ............. B26D 1/085 |

OTHER PUBLICATIONS

Unpublished U.S. Appl. No. 17/195,852, filed Mar. 9, 2021, to Deborah Sue Slovut et al.
Unpublished U.S. Appl. No. 17/156,744, filed Jan. 25, 2021, to Deborah Sue Slovut et al.
PCT Search Report and Written Opinion for PCT/US2018/050378 dated Nov. 15, 2018, 14 pages.
Final Office Action; U.S. Appl. No. 16/124,587 dated Apr. 21, 2021.
Final Office Action; U.S. Appl. No. 16/124,587 dated May 20, 2022.
Final Office Action; U.S. Appl. No. 16/124,621 dated Mar. 29, 2021.
Final Office Action; U.S. Appl. No. 16/124,621 dated Oct. 13, 2022.
Final Office Action; U.S. Appl. No. 16/124,621 dated Nov. 9, 2020.
Final Office Action; U.S. Appl. No. 16/124,621 dated Dec. 21, 2021.
Final Office Action; U.S. Appl. No. 16/127,417 dated Jun. 29, 2021.
Final Office Action; U.S. Appl. No. 16/127,417 dated Jul. 24, 2020.
Final Office Action; U.S. Appl. No. 16/127,450 dated Jul. 24, 2020.
Final Office Action; U.S. Appl. No. 16/127,519 dated Jul. 24, 2020.
Final Office Action; U.S. Appl. No. 16/127,540 dated Oct. 8, 2020.
Final Office Action; U.S. Appl. No. 16/127,561 dated Oct. 8, 2020.
Non-Final Office Action; U.S. Appl. No. 16/124,587 dated Sep. 4, 2020.
Non-Final Office Action; U.S. Appl. No. 16/124,587 dated Sep. 28, 2021.
Non-Final Office Action; U.S. Appl. No. 16/124,587 dated Oct. 5, 2022.
Non-Final Office Action; U.S. Appl. No. 16/124,621 dated Apr. 4, 2022.
Non-Final Office Action; U.S. Appl. No. 16/124,621 dated Jun. 12, 2020.
Non-Final Office Action; U.S. Appl. No. 16/124,621 dated Jul. 29, 2021.
Non-Final Office Action; U.S. Appl. No. 16/127,417 dated Mar. 31, 2020.
Non-Final Office Action; U.S. Appl. No. 16/127,417 dated Dec. 9, 2020.
Non-Final Office Action; U.S. Appl. No. 16/127,450 dated Mar. 31, 2020.
Non-Final Office Action; U.S. Appl. No. 16/127,450 dated Nov. 9, 2020.
Non-Final Office Action; U.S. Appl. No. 16/127,519 dated Mar. 31, 2020.
Non-Final Office Action; U.S. Appl. No. 16/127,540 dated Jun. 25, 2020.
Non-Final Office Action; U.S. Appl. No. 16/127,561 dated Jun. 29, 2020.
Notice of Allowance; U.S. Appl. No. 16/127,417 dated Nov. 1, 2021.
Notice of Allowance; U.S. Appl. No. 16/127,450 dated Mar. 24, 2021.
Notice of Allowance; U.S. Appl. No. 16/127,450 dated Jul. 15, 2021.
Notice of Allowance; U.S. Appl. No. 16/127,519 dated Nov. 12, 2020.
Notice of Allowance; U.S. Appl. No. 16/127,540 dated Jan. 22, 2021.
Notice of Allowance; U.S. Appl. No. 16/127,561 dated Jan. 21, 2021.

* cited by examiner

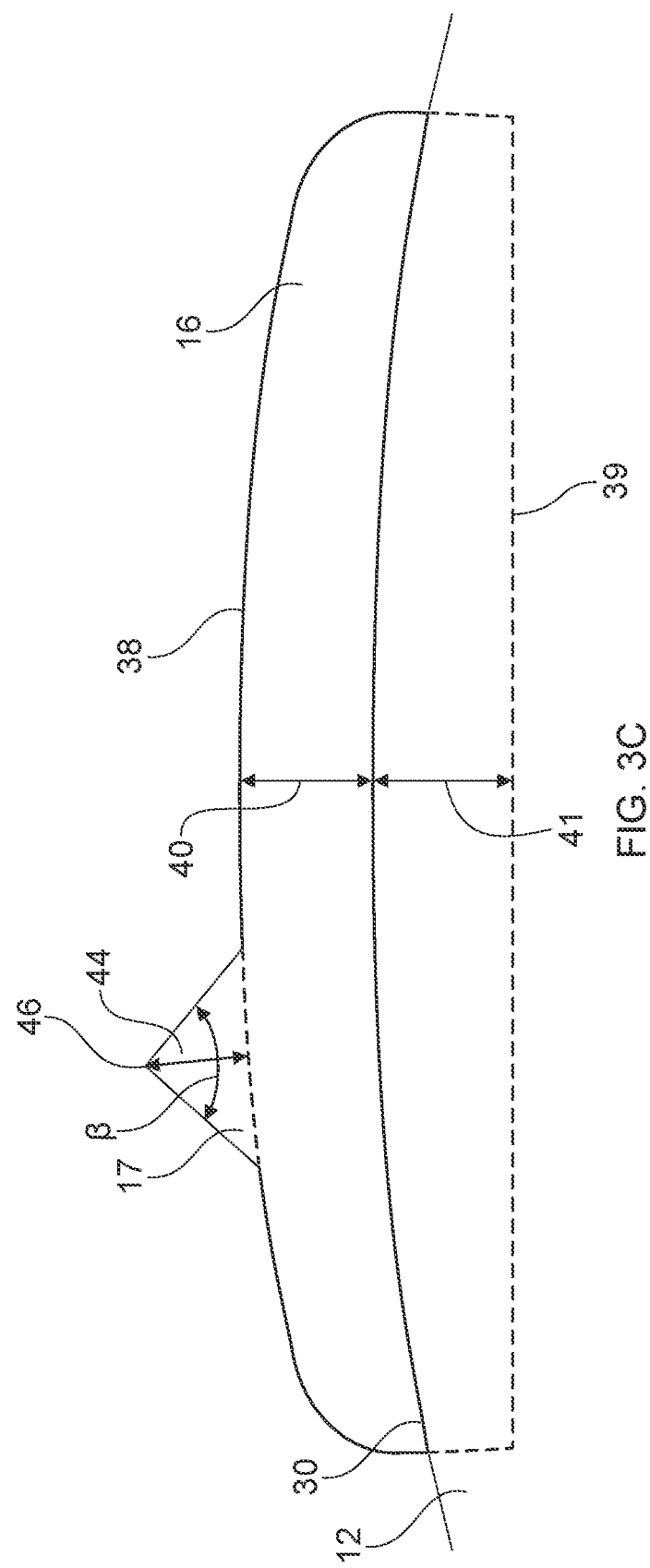

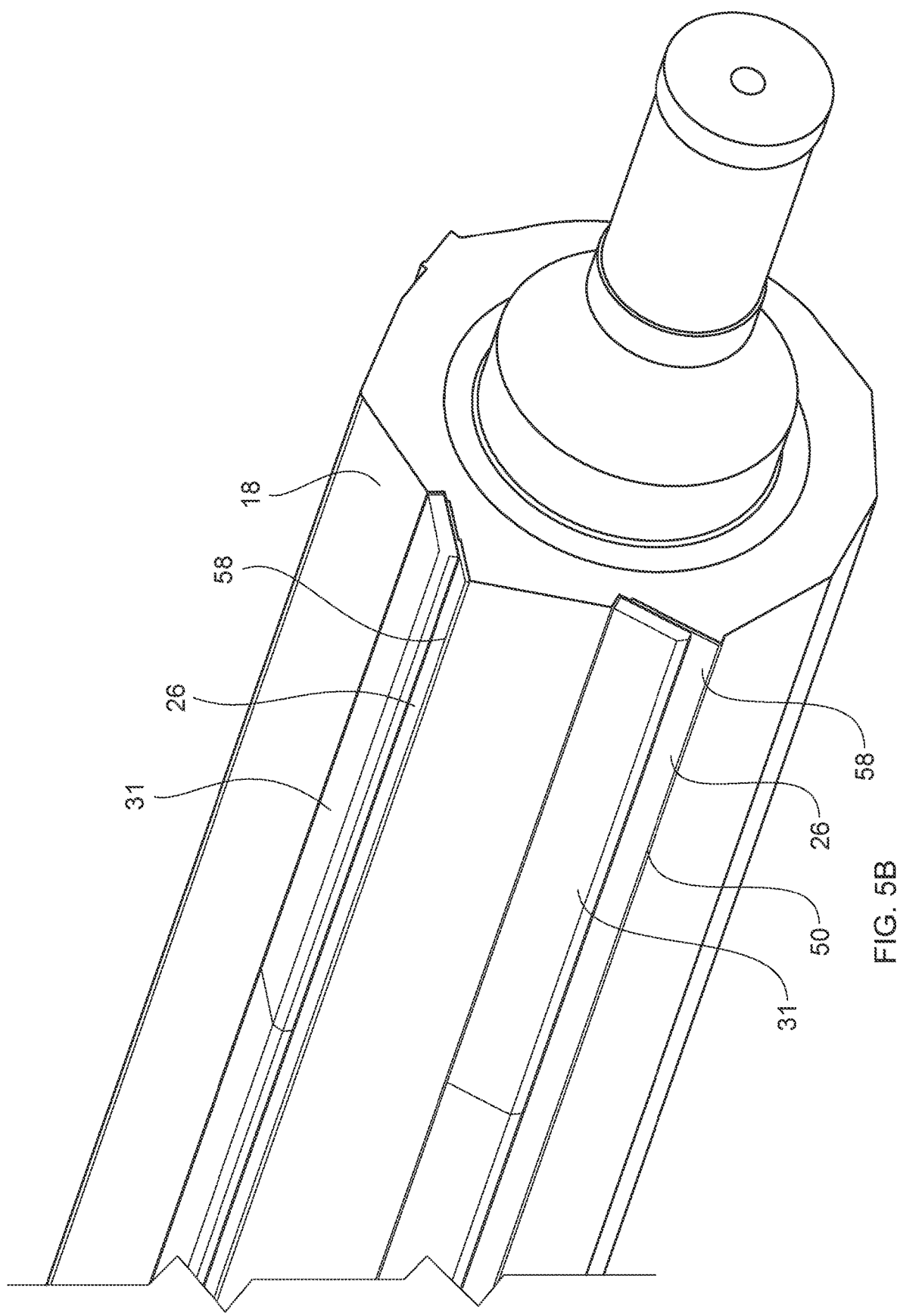

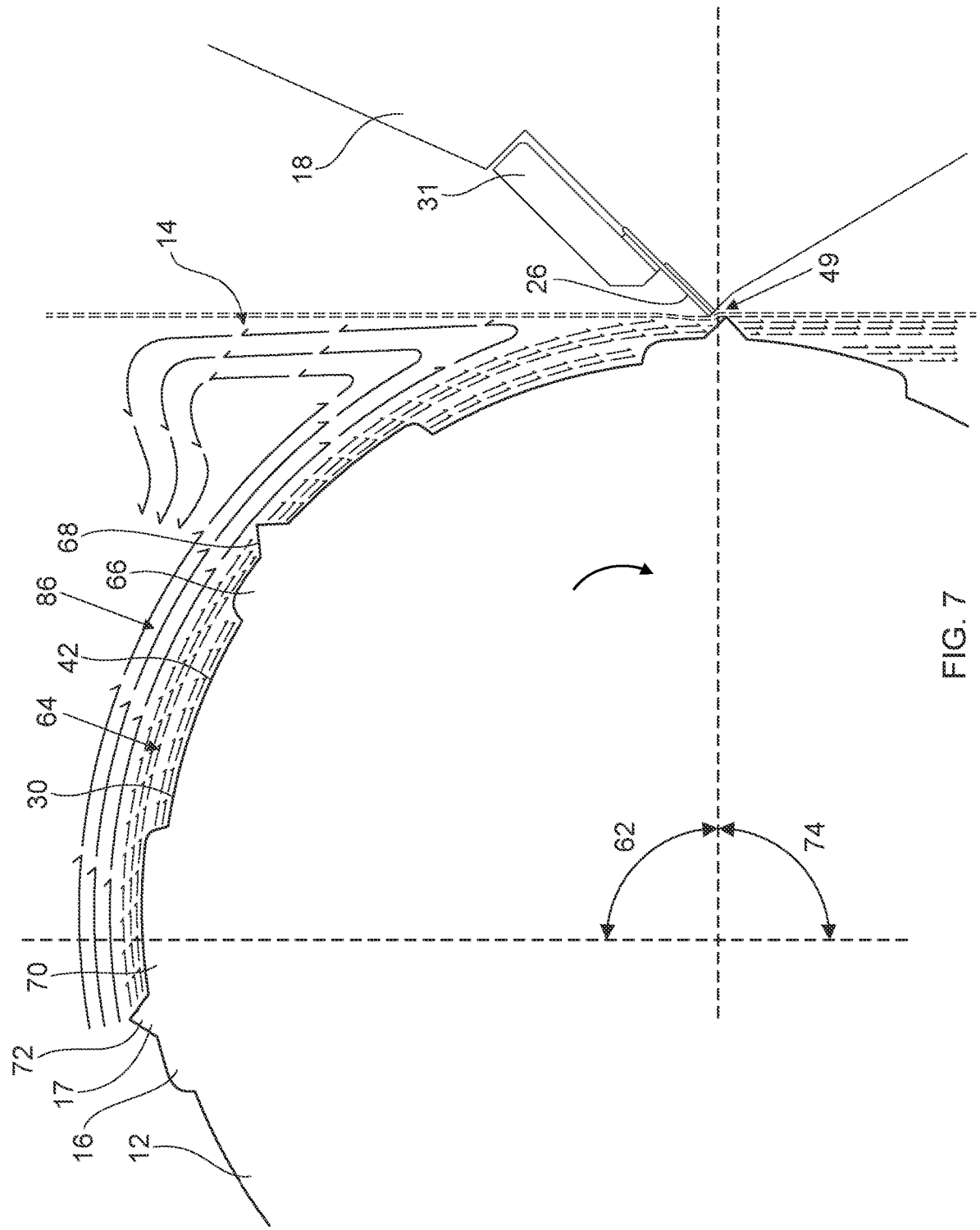

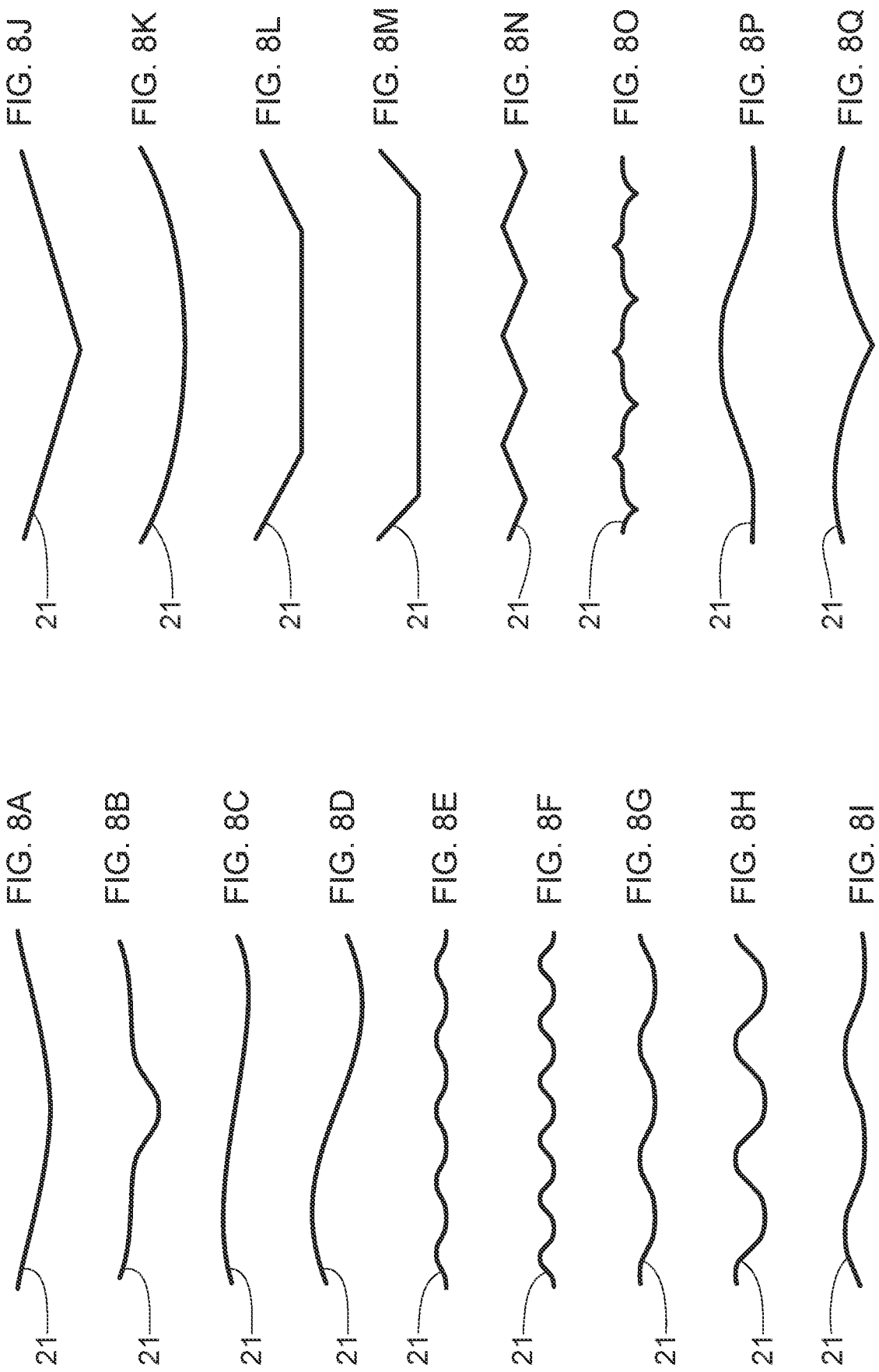

SANITARY TISSUE PRODUCT WITH A SHAPED LINE OF WEAKNESS

CROSS REFERENCE TO RELATED APPLICATIONS

This application is a continuation of, and claims priority under 35 U.S.C. § 120 to, U.S. patent application Ser. No. 16/127,519, filed on Sep. 11, 2018, which claims the benefit, under 35 USC § 119(e), of U.S. Provisional Patent Application Ser. No. 62/556,720, filed on Sep. 11, 2017, the entire disclosures of which are fully incorporated by reference herein.

FIELD OF THE INVENTION

The present disclosure relates to sanitary tissue products with a shaped line of weakness, and more specifically, to rolled sanitary tissue products with a shaped line of weakness that meet the needs of the consumer for reliable one hand tearing and dispensability, while also being commercial-scale converting process friendly.

BACKGROUND

Many rolled products include a line of weakness having one or more perforations to aid in tearing individual articles off the product roll. For example, such products can include wax paper, aluminum foil, disposable bags, and sanitary tissue products such as toilet tissue and paper towels. Specifically, rolls of sanitary tissue products may include perforation lines to more easily allow the tearing of discrete sheets from the roll. Such products are commonly used in households, businesses, restaurants, shops, and the like.

Typically, a line of weakness in a sanitary tissue product consists of a straight line perforation across the width of the web (parallel to the CD direction of the web). However, it has been found that sanitary tissue consumers desire products that have a distinguishing feature over other products. Accordingly, sanitary tissue manufacturers desire to produce products in which consumers can easily distinguish their products from similar products produced by competitors. A shaped (i.e., a nonlinear or curvilinear) line of weakness is one distinguishing characteristic that can be added to a sanitary tissue product to address the wants of both manufacturer and consumer. Moreover, a shaped line of weakness not only provides a way for consumers to distinguish a manufacture's product, but also communicates to consumers a perception of luxury, elegance, softness, and/or strength, as well as potential for ease of dispensability.

Previous attempts to run commercial-scale production of rolled sanitary tissue products that include a shaped line of weakness have been unsuccessful. Early test-stand development work showed promise, but the scale-up to high speed, commercial-scale converting lines was met with failure. Previous approaches failed because they did not consider the impacts of the high speeds of the commercial-scale converting equipment, the dust hygiene implications on such equipment, the tight tolerances between the equipment (e.g., spacing between roll body surfaces of the converting equipment), the web sheet aerodynamics, the large web sheet widths, and the extremes of the CD and MD property variation of the sanitary tissue webs being converted, as well as other factors. Accordingly, previous commercial-scale production attempts were plagued by short run times of just a few minutes due to web breaks, an inability to reach or maintain target production rates (i.e., low reliability percentage), an inability to reach target web tensions without web breaks, and an inability to wind rolls to target compressibility or firmness (e.g., the sanitary tissue rolls were mushy and would not be acceptable to consumers, nor run well on downstream high-speed converting and packaging equipment). Net, from a commercial-scale converting process perspective, previous attempts to impart a shaped line of weakness feature on rolled sanitary tissue products were dramatically unsuccessful based upon their inability to obtain the combination of both process reliability and product quality requirements.

Accordingly, there is a need for sanitary tissue products with a shaped line of weakness that exhibit one or more performance parameters and/or performance factors that indicate that the sanitary tissue both meets the needs of a consumer for reliable one hand tearing dispensability, and is also commercial-scale converting process friendly. Additionally, there is a need for sanitary tissue products with a shaped line of weakness that exhibit one or more performance parameters and/or performance factors that indicate that the sanitary tissue both meets the needs of a consumer for reliable one hand tearing dispensability, and is also commercial-scale converting process friendly, while also communicating the softness of the sanitary tissue to the consumer.

Accordingly, there is also a need for a roll of sanitary tissue product with a shaped line of weakness, wherein the roll exhibits a target roll compressibility. Further, there is a need for a roll of sanitary tissues with a shaped line of weakness, wherein the roll exhibits a target roll compressibility, and the sanitary tissue on the roll meets target consumer dispensability as measured by the Full Sheet Average Trapezoidal Tear Strength Test Method. Further, there is a need for a roll of sanitary tissues with a shaped line of weakness, wherein the roll exhibits a target roll compressibility, and comprises one or more performance parameters and/or performance factors that indicate that the sanitary tissue on the roll both meets the needs of a consumer for reliable one hand tearing dispensability, and is also commercial-scale converting process friendly, while also communicating the softness of the sanitary tissue to the consumer through the free fiber ends along the ruptured shaped line of weakness.

BRIEF DESCRIPTION OF THE DRAWINGS

The above-mentioned and other features and advantages of this disclosure, and the manner of attaining them, will become more apparent and the disclosure itself will be better understood by reference to the following description of non-limiting examples of the disclosure taken in conjunction with the accompanying drawings, wherein:

FIG. 3C is a partial side view of an anvil block and an anvil bead in accordance with one non-limiting form of the present disclosure;

FIG. 5B is a partial perspective view of a support including a blade in accordance with one non-limiting form of the present disclosure;

FIG. 7 is a partial side view of a cylinder and a support and the air flow during perforation of a web in accordance with one non-limiting form of the present disclosure.

FIGS. 8A-8Q are schematic representations of the shape of a line of weakness in accordance with one non-limiting form of the present disclosure;

DETAILED DESCRIPTION

Figure 1:
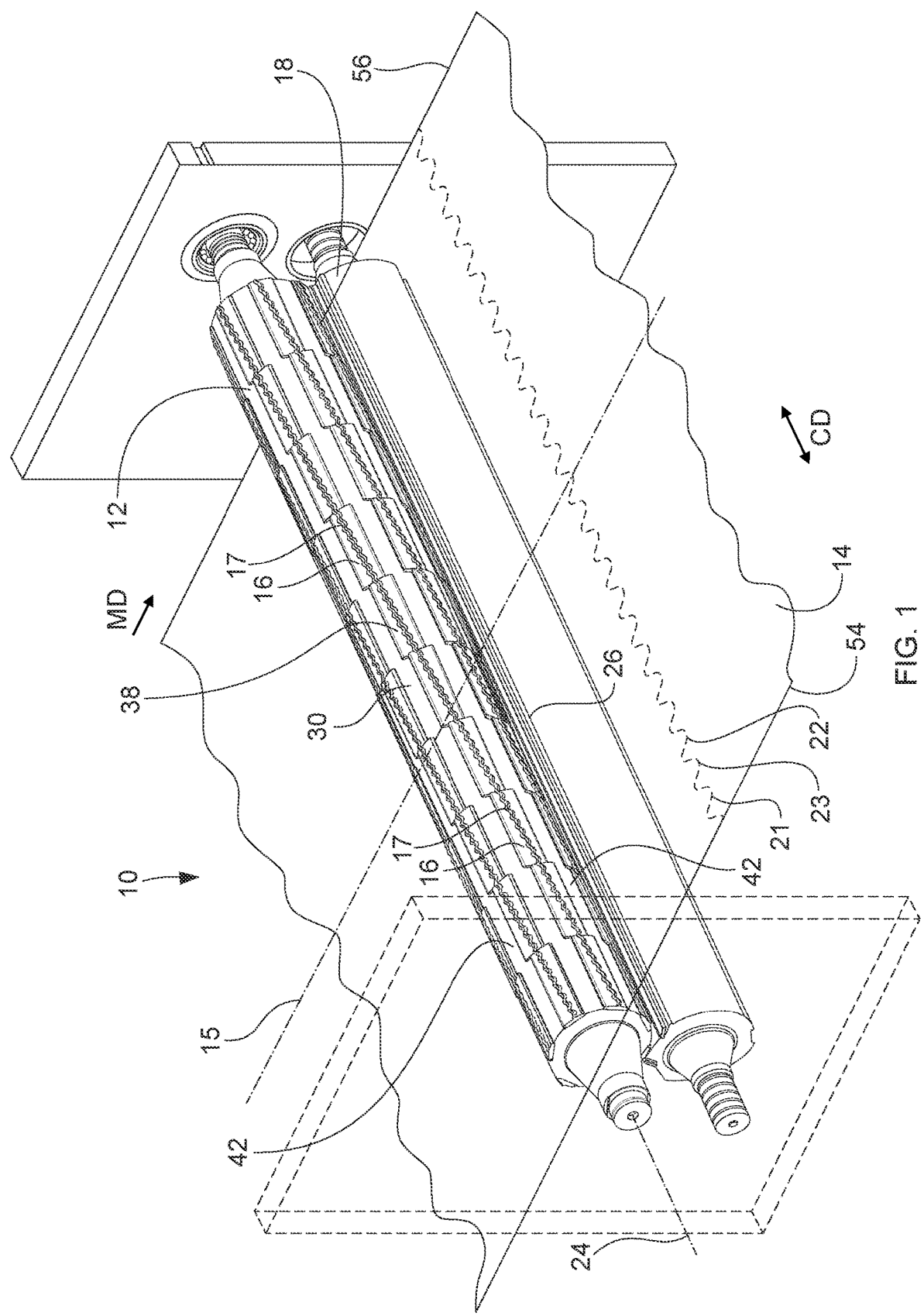
FIG. 1 is a perspective view of a perforating apparatus in accordance with one non-limiting form of the present disclosure.

Various non-limiting forms of the present disclosure will now be described to provide an overall understanding of the principles of the structure, properties, function, manufacture, and use of a web comprising a shaped line of weakness. The features in connection with any particular non-limiting form detailed or illustrated herein can be combined with the features of other non-limiting forms detailed or illustrated herein. Such modifications and variations are intended to be included within the scope of this disclosure.

"Fibrous structure" as used herein means a structure that comprises one or more fibrous elements. In one example, a fibrous structure according to the present disclosure means an association of fibrous elements that together form a structure capable of performing a function. A nonlimiting example of a fibrous structure of the present disclosure is an absorbent paper product, which can be a sanitary tissue product such as a paper towel, bath tissue, or other rolled, absorbent paper product.

Non-limiting examples of processes for making fibrous structures include known wet-laid papermaking processes, air-laid papermaking processes, and wet, solution, and dry filament spinning processes, for example meltblowing and spunbonding spinning processes, that are typically referred to as nonwoven processes. Such processes can comprise the steps of preparing a fiber composition in the form of a suspension in a medium, either wet, more specifically aqueous medium, or dry, more specifically gaseous, i.e. with air as medium. The aqueous medium used for wet-laid processes is oftentimes referred to as fiber slurry. The fibrous suspension is then used to deposit a plurality of fibers onto a forming wire or belt such that an embryonic fibrous structure is formed, after which drying and/or bonding the fibers together results in a fibrous structure. Further processing the fibrous structure can be carried out such that a finished fibrous structure is formed. For example, in typical papermaking processes, the finished fibrous structure is the fibrous structure that is wound on the reel at the end of papermaking and can subsequently be converted into a finished product (e.g., a sanitary tissue product).

"Fibrous element" as used herein means an elongate particulate having a length greatly exceeding its average diameter, i.e., a length to average diameter ratio of at least about 10. A fibrous element may be a filament or a fiber. In one example, the fibrous element is a single fibrous element rather than a yarn comprising a plurality of fibrous elements.

The fibrous elements of the present disclosure may be spun from polymer melt compositions via suitable spinning operations, such as meltblowing and/or spunbonding and/or they may be obtained from natural sources such as vegetative sources, for example trees.

The fibrous elements of the present disclosure may be monocomponent and/or multicomponent. For example, the fibrous elements may comprise bicomponent fibers and/or filaments. The bicomponent fibers and/or filaments may be in any form, such as side-by-side, core and sheath, islands-in-the-sea and the like.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol, thermoplastic polymer, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.). A fiber can be elongate physical structure having an apparent length greatly exceeding its apparent diameter (i.e., a length to diameter ratio of at least about 10.) Fibers having a non-circular cross-section and/or tubular shape are common; the "diameter" in this case can be considered to be the diameter of a circle having a cross-sectional area equal to the cross-sectional area of the fiber.

Fibers are typically considered discontinuous in nature. Non-limiting examples of fibers include pulp fibers, such as wood pulp fibers, and synthetic staple fibers such as polypropylene, polyethylene, polyester, copolymers thereof, rayon, glass fibers and polyvinyl alcohol fibers.

Staple fibers may be produced by spinning a filament tow and then cutting the tow into segments of less than 5.08 cm (2 in.) thus producing fibers.

In one example of the present disclosure, a fiber may be a naturally occurring fiber, which means it is obtained from a naturally occurring source, such as a vegetative source, for example a tree and/or other plant. Such fibers are typically used in papermaking and are oftentimes referred to as papermaking fibers. Papermaking fibers useful in the present disclosure include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp.

Chemical pulps, however, may be preferred since they impart a superior tactile sense of softness to fibrous structures made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. Also applicable to the present disclosure are fibers derived from recycled paper, which may contain any or all of the above categories of fibers as well as other non-fibrous polymers such as fillers, softening agents, wet and dry strength agents, and adhesives used to facilitate the original papermaking.

In addition to the various wood pulp fibers, other cellulosic fibers such as cotton linters, rayon, lyocell, bamboo, and bagasse fibers can be used in the fibrous structures of the present disclosure.

"Sanitary tissue product" or "sanitary tissue" as used herein means one or more finished fibrous structures, that are useful as a wiping implement for post-urinary and post-bowel movement cleaning (e.g., toilet tissue, also referred to as bath tissue), for otorhinolaryngological discharges (e.g., facial tissue), and multi-functional absorbent and cleaning and drying uses (e.g., paper towels, shop towels). The sanitary tissue products can be embossed or not embossed, and/or creped or uncreped. Any of the sanitary tissue products detailed herein can be provided in the form of "Rolled product(s)," as defined herein.

"Basis Weight" as used herein is the weight per unit area of a sample reported in lbs/3000 ft$^2$ or g/m$^2$.

"Density" as used herein is calculated as the quotient of the Basis Weight expressed in grams per square meter divided by the Caliper expressed in microns. The resulting Density is expressed as grams per cubic centimeter (g/cm$^3$ or g/cc).

"Ply" as used herein means an individual, integral fibrous structure.

"Plies" as used herein means two or more individual, integral fibrous structures disposed in a substantially contiguous, face-to-face relationship with one another, forming a multi-ply fibrous structure and/or multi-ply sanitary tissue product. It is also contemplated that an individual, integral fibrous structure can effectively form a multi-ply fibrous structure, for example, by being folded on itself.

"Rolled product(s)" as used herein include fibrous structures, paper, and sanitary tissue products that are in the form of a web and can be wound about a core. For example, rolled sanitary tissue products can be convolutedly wound upon itself about a core or without a core to form a sanitary tissue product roll perforated into the form of discrete sheets, as is commonly known for toilet tissue and paper towels.

"Machine Direction," MD, as used herein is the direction of manufacture for a perforated web. The machine direction can be the direction in which a web is fed through a perforating apparatus that can comprise a rotating cylinder and support, as discussed below in one form. The machine direction can be the direction in which web travels as it passes through a blade and an anvil of a perforating apparatus.

"Cross Machine Direction," CD as used herein is the direction substantially perpendicular to the machine direction. The cross machine direction can be substantially perpendicular to the direction in which a web is fed through a cylinder and lower support in one form. The cross machine direction can be the direction substantially perpendicular to the direction in which web travels as it passes through a blade and an anvil of a perforating apparatus.

"Roll Bulk" as used herein is the volume of paper divided by its mass on the wound roll. Roll Bulk is calculated by multiplying pi (3.142) by the quantity obtained by calculating the difference of the roll diameter squared in cm squared (cm$^2$) and the outer core diameter squared in cm squared (cm$^2$) divided by 4, divided by the quantity sheet length in cm multiplied by the sheet count multiplied by the Bone Dry Basis Weight of the sheet in grams (g) per cm squared (cm$^2$).

The following disclosure relates to the processes utilized to manufacture the rolled sanitary tissue products of the present disclosure (e.g., rolled sanitary tissue products with a shaped line of weakness that meet the needs of the consumer for reliable one hand tearing and dispensability, while also being commercial-scale converting process friendly).

The process and apparatus for perforating the web includes rotating a cylinder about a longitudinal cylinder axis. The cylinder may include an outer circumferential surface that substantially surrounds the longitudinal cylinder axis. The outer circumferential surface may include a plurality of recessed portions. These recessed portions may be positioned both longitudinally, also referred to herein as axially, and radially about the outer circumferential surface. The recessed portions are configured to accept an anvil block or two or more anvil block segments. The anvil blocks may be removably connected with the recessed portions. The anvil blocks may be offset from one another in the longitudinal/axial direction. Further, the anvil blocks may be positioned radially about the outer circumferential surface and cavities are formed between adjacent, radially positioned anvil blocks. These cavities are formed by the anvil blocks extending radially above the outer circumferential surface of the cylinder. Each of the anvil blocks may include an anvil bead. The anvil bead may be removably connected to the anvil block or the anvil bead and the anvil block may be manufactured together. The anvil beads together form a shape extending along the longitudinal cylinder axis. The anvil beads operatively engage the blade. The blade may be supported by a support and a clamp. The blade may include a single blade or a plurality of blades. The blade may be stationary or the blade may oscillate in a direction substantially parallel to the cross direction to minimize wear. The web is fed between the anvil bead and the blade to form perforations. The perforations imparted to the web form a shaped, or non-linear, line of weakness. However, debris is generated from perforating the web and/or upstream processing of the web. This debris is controlled due to the shape of the cylinder in combination with the anvil block and the anvil bead. As previously discussed, the cavity is formed between adjacent anvil blocks, including anvil beads. Due to the air flow created by the rotating cylinder and the geometry of the anvil block, anvil bead, and the cavity, the debris is drawn into the cavity and away from the web. This substantially minimizes any adverse effect the debris may have on the web and/or the perforating process. The debris is held in the cavity until the cavity is rotated to a position downstream of the nip, where the anvil bead engages the blade. Once the cavity is downstream of the nip, the debris may be expelled from the cavity and any other debris may be pushed away from the outer circumferential surface of the cylinder. Due the aforementioned process, the strain on the web may be maintained throughout the perforating process.

Referring to FIG. 1, a perforating apparatus 10 is shown for forming a shaped line of weakness 21 comprising one or more perforations 22 and one or more bond areas 23 therebetween on a web 14. The perforating apparatus 10 comprises a cylinder 12 and a support 18. The cylinder 12 may be suspended between one or more braces that serve to hold the cylinder in operative position and allow the cylinder to rotate. The cylinder 12 has a longitudinal cylinder axis 24 about which the cylinder 12 is rotatable. The cylinder 12 may have a substantially circular shaped cross-section or any other shaped cross-section that may rotate about an axis and produce a web 14 with a line of weakness 21. The cylinder 12 may be a solid or substantially hollow cylindrical shaped device. The cylinder 12 may comprise an outer circumferential surface 30 positioned radially outward from and substantially surrounding the longitudinal cylinder axis 24.

As illustrated in FIG. 1, a plurality of anvil blocks 16 may be disposed on the outer circumferential surface 30 of the cylinder 12. The anvil blocks 16 may be offset from one another along the longitudinal cylinder axis 24. Further, there may be anvil blocks 16 disposed radially about the outer circumferential surface 30 of the cylinder 12. Adjacent anvil blocks positioned radially about the outer circumferential surface 30 define cavities 42 therebetween. Each of the anvil blocks 16 may include an anvil bead 17. The anvil bead 17 protrudes radially away from a surface 38 of the anvil block 16. The anvil bead 17 may be shaped, also referred to herein as non-linear. Further, the anvil beads 17 may be helically mounted along the longitudinal cylinder axis 24.

Opposite the cylinder 12, the support 18 may comprise a blade 26. The blade 26 may be disposed on the support 18. By disposed is meant the blade may be attached, removeably attached, clamped, bolted, or otherwise held by the support 18 in a stable operative position with respect to the cylinder 12. The blade 26 may be a single blade or include a plurality of blade segments.

The cylinder 12 may be rotated about the longitudinal cylinder axis 24 such that the anvil beads 17 engage the blade 26. The web 14 may include a longitudinal web axis 15, a first side edge 54, and a second side edge 56 opposite the first side edge 54. The web 14 may be fed through the perforating apparatus such that the line of weakness imparted to the web extends from the first side edge 54 to the second side edge 56. The web 14 is fed between the anvil beads 17 and the blade 26 such that the longitudinal web axis 15 extends in a direction substantially parallel to the machine direction MD. The longitudinal web axis 15 is also tangential to the outer circumferential surface 30 of the cylinder 12 as the web 14 passes between the anvil bead 17 and the blade 26. The anvil bead 17 and the blade 26 cooperate in contacting relationship as the web 14 traverses through, resulting a shaped line of weakness 21. The shaped line of weakness includes perforations 22 and bond areas 23. Generally, the shape of the line of weakness is the same as or similar to the shape of the anvil bead 17.

Figure 2A:
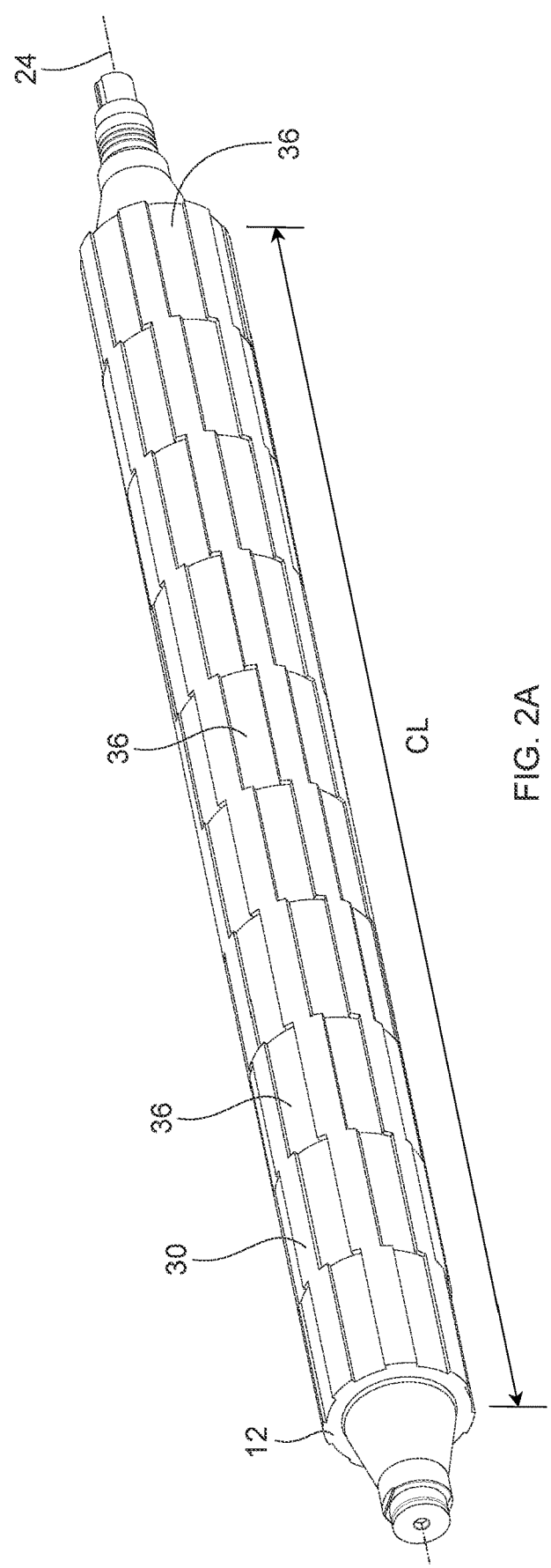
FIG. 2A is a perspective view of a cylinder in accordance with one non-limiting form of the present disclosure.
Figure 2B:
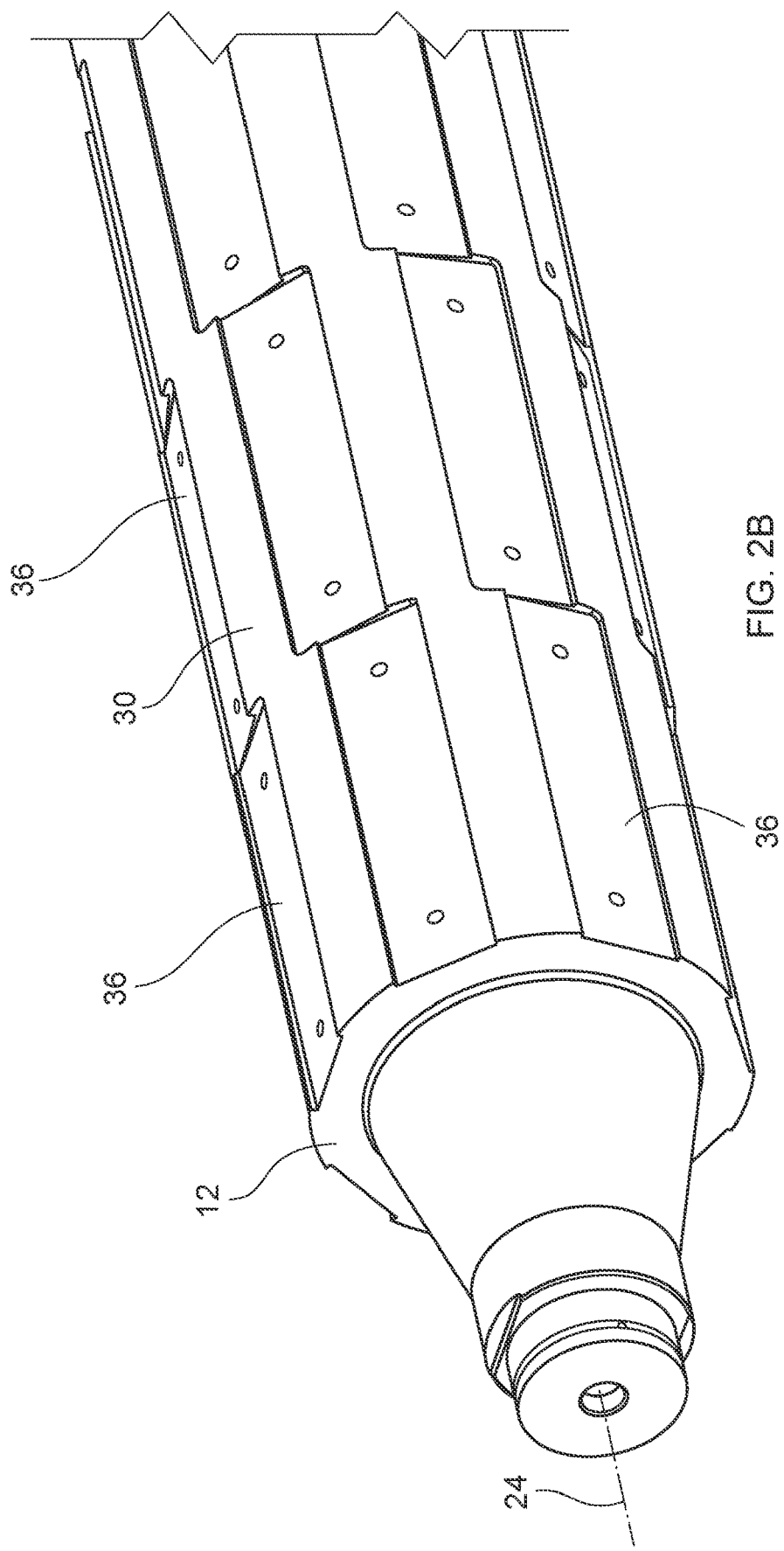
FIG. 2B is a partial perspective view of a cylinder in accordance with one non-limiting form of the present disclosure.

As previously stated, the perforating apparatus 10 may include a cylinder 12. The cylinder 12 may be configured to rotate about a longitudinal cylinder axis 24. The cylinder 12 may define a plurality of recessed portions 36, as illustrated in FIGS. 2A and 2B. The recessed portions 36 may be spaced along the longitudinal cylinder axis 24 and circumferentially about the outer circumferential surface 30. The recessed portions 36 may be configured to accept one or more anvil blocks 16. The recessed portions 36 may be any size and shape such that the anvil blocks 16 may be disposed within the recessed portion. The cylinder 12 may have a cylinder length CL extending in the cross direction CD. The cylinder length CL may be the same length as or longer than the web 14 that is to undergo processing. The cylinder length CL may be from about 50 inches to about 200 inches and/or from about 75 inches to about 150 inches and/or from about 90 inches to 110 inches, including all 0.1 inch increments between the recited ranges. The cylinder 12 may be made from metal, such as steel, aluminum, tungsten carbide, or another material that may be rotated at the desired manufacturing speeds.

It is to be appreciated that in some forms, the cylinder 12 may not include recessed portions and the anvil blocks may be attached to the outer circumferential surface 30 of the cylinder 12. It is also to be appreciated that a protruding portion may be machined or attached to the outer circumferential surface 30 of the cylinder onto which the anvil block 16 and/or the anvil bead 17 may be removably connected.

Figure 3A:
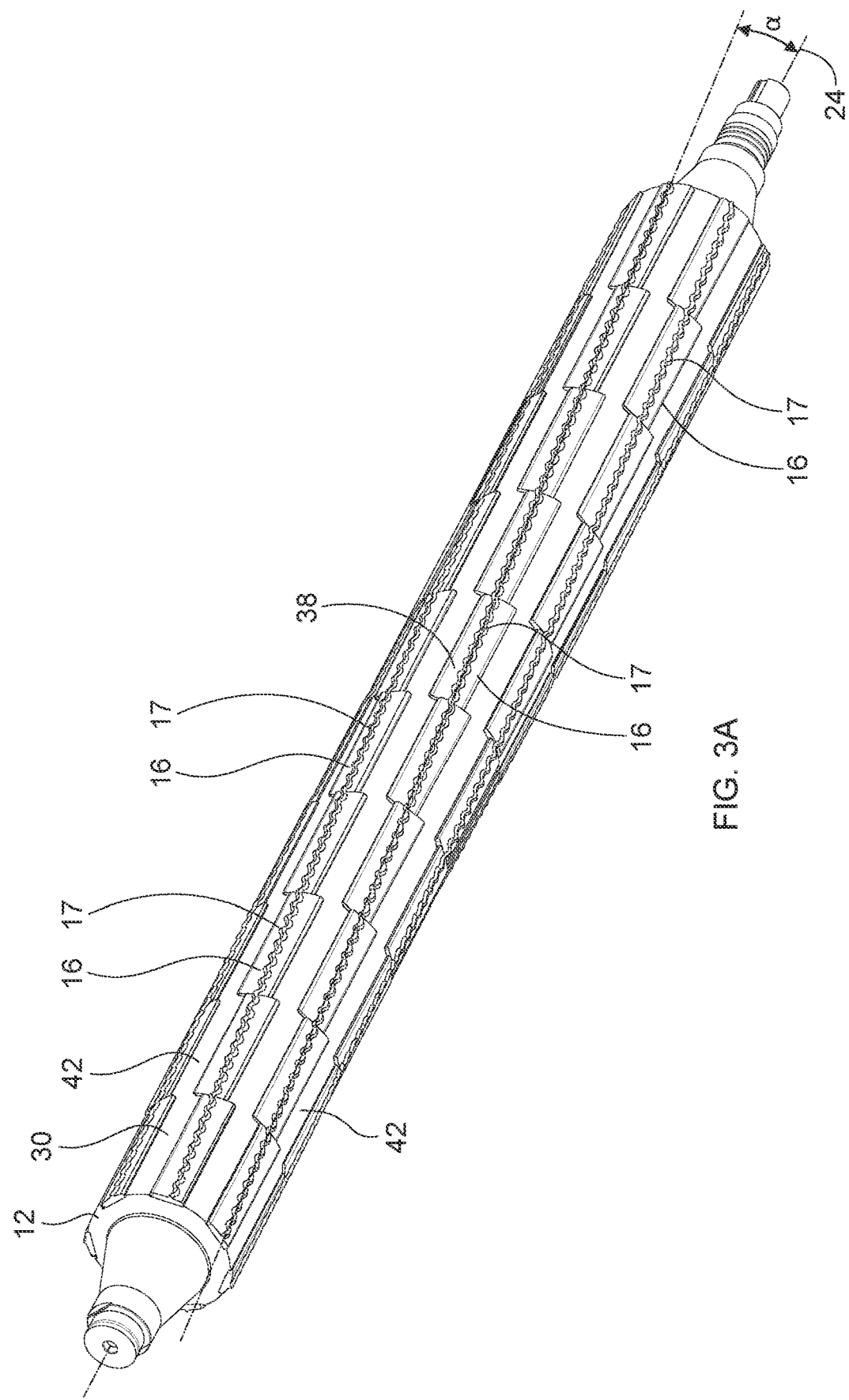
FIG. 3A is a perspective view of a cylinder including an anvil block and an anvil bead in accordance with one non-limiting form of the present disclosure.
Figure 3B:
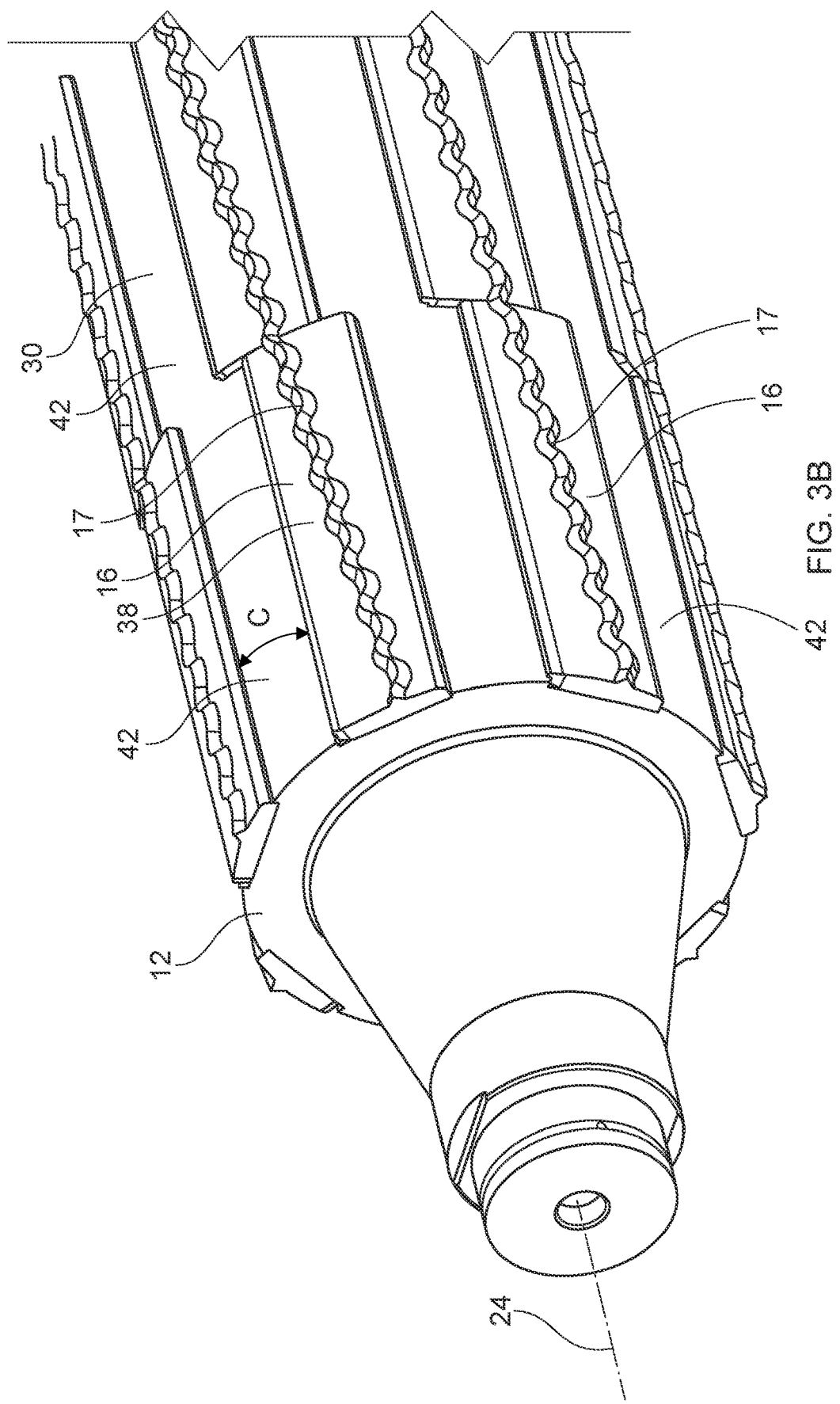
FIG. 3B is a partial perspective view of a cylinder including an anvil block and an anvil bead in accordance with one non-limiting form of the present disclosure.

As illustrated in FIGS. 3A-3C, the anvil blocks 16 may be removably connected to the cylinder 12. In some forms, the anvil blocks 16 may be magnetically attached to the recessed portions 36 of the cylinder 12. In some forms, the anvil blocks 16 may be chemically attached, such as by adhesive, or mechanically attached, such as by screwing, pinning, clamping, bolting, or otherwise joining the anvil block to the outer circumferential surface 30 of the cylinder 12. The individual anvil blocks allow for ease of replacement and individual adjustment. For example, worn and/or damaged anvil blocks may be individually replaced. Further, the removable anvil blocks allow for different anvil bead profiles to be switch out easily and for each anvil block to be individually adjusted for optimum processing.

The anvil blocks 16 may include a first anvil block surface 38 and a second anvil block surface 39, which is opposite the first anvil block surface 38. The second anvil block surface 39 may be in contacting relationship with the recessed portion and/or the outer circumferential surface 30 of the cylinder 12. The anvil block 16 may include a recessed anvil block height 41, which is the portion of the anvil block positioned below the outer circumferential surface 30. The recessed anvil block height 41 is measured from the outer circumferential surface 30 to the second anvil block surface 39. The recessed anvil block height may be from about 0.05 inches to about 0.4 inches and/or from about 0.1 inches to about 0.3 inches, including all 0.01 inch increments between the recited ranges. The first anvil block surface 38 may protrude radially away from the outer circumferential surface 30 of the cylinder 12 forming an anvil block height 40. The anvil block height 40 includes the portion of the anvil block that extends above the outer circumferential surface 30 of the cylinder. The anvil block height is measured from the outer circumferential surface 30 to the first anvil block surface 38. In some forms, the anvil block height 40 may be from about 0.1 inches to about 0.5 inches and/or from about 0.2 inches to about 0.4 inches, including all 0.01 inch increments between the recited ranges. For example, an anvil block height 40 of 0.3 inches would be included in the aforementioned recited ranges. Each anvil block 16 may have an anvil block height 40 such that a cavity 42 is formed between adjacent, radially positioned anvil blocks 16, as indicated by arrow C in FIG. 3B. More specifically, anvil blocks 16 disposed longitudinally along the longitudinal cylinder axis and positioned about the outer circumferential surface 30, form cavities 42 extending between the anvil blocks that are adjacent to one another radially about the outer circumferential surface and along the longitudinal cylinder axis. The cavity 42 allows debris from the manufacturing process to be controlled during the manufacturing process, which will be described in more detail herein. It is also to be appreciated that that the anvil block surface 38 and the anvil block surface 39 may each have a radius of curvature, may be substantially planar, or any other shape that allows for perforation of the web as described herein.

The number of anvil blocks including anvil beads positioned radially about the outer circumferential surface may be based on the distance that is desired between adjacent lines of weakness on the web and/or the size of the cylinder. Successive lines of weakness 21 imparted to the web 14 may be spaced at a distance equal to about the distance between adjacent, radially positioned anvil beads. In some forms, the anvil blocks may be spaced such that the anvil blocks are equally spaced from one another about the outer circumferential surface of the cylinder. For example, for a cylinder 12 including three anvil blocks positioned radially about the circumference of the cylinder, the three anvil blocks will be spaced at about one-third increments about the outer circumferential surface 30 of the cylinder 12.

It is also to be appreciated that a single anvil block may include one or more anvil block segments. For example, several anvil block segments may fit within a recessed portion 36 to form an anvil block. The anvil block may be broken into one or more segments for machinability and/or ease of replacement, for example.

Still referring to FIGS. 3A-3C, the anvil block 16 may include an anvil bead 17. The anvil bead 17 may protrude from the first anvil block surface 38 away from the longitudinal cylinder axis 24. The anvil beads 17 present on each anvil block 16 may abut one another such that the anvil beads form a substantially continuous shape along the cylinder 12. Each individual anvil bead 17 may be shaped and the plurality of anvil beads 17 may form any shape along the cylinder that is desired to be imparted to the web 14. It is to be appreciated that the shape of each individual anvil bead may be the same or different. For example, the anvil beads may form a sinusoidal shape or a saw-tooth shape. FIG. 8A-8Q illustrates various shapes the plurality of anvil beads may form, alone or in combination. The shape of the anvil beads is the same as, or similar to, the shape imparted to the web 14 as a line of weakness 21. In some forms, for example the anvil beads may form a sinusoidal shape along the longitudinal cylinder axis such that the line of weakness imparted to the web has a wavelength 34 of from about 0.75 inches to about 2.5 inches and an amplitude 32 of from about 0.1 inches to about 1 inch. For example, a line of weakness having a wavelength 34 of about 1.38 inches and an amplitude 32 of about 0.236 inches may be manufactured by the disclosed process and apparatus and is within the above specified ranges.

It is to be appreciated that a shaped blade may be used in place of the anvil beads. It is also to be appreciated that to obtain a shaped line of weakness, the shaped element, such as the anvil beads or blades, should be present on the rotating device, such as the rotating cylinder. The same result does not occur if the shape is on the stationary, or non-rotating, device.

It is also to be appreciated that the anvil bead 17 and the anvil block 16 may be machined from the same material such that the anvil bead 17 is attached to the anvil block 16. The anvil bead 17 may also be removably connected to the anvil block 16 such that the anvil bead 17 is separate from the anvil block 16 when not connected. This allows for the anvil bead to be changed independent of the anvil block 16. For example, the shape of the anvil bead may be changed without changing the anvil block. The anvil bead may be switch from a non-linear, shaped anvil bead to a straight, linear anvil bead. The anvil block may also not contain any anvil bead. The cylinder may be operated without the anvil block having the anvil bead. This may be done to retain the surface profile of the cylinder but to have a particular anvil block not affect the traversing web.

Each anvil bead 17 may have an anvil bead height 44 measured from the first anvil block surface 38 to an anvil bead tip 46. The anvil bead height 44 may be from about 0.01 inches to about 0.40 inches, including all 0.01 inches therebetween. The anvil bead height 44 in combination with the anvil block height 40 allow for control of the debris from the manufacturing process. For example, in some forms, the height from the outer circumferential surface 30 to the anvil bead tip 46 is from about 0.02 inches to about 0.8 inches and/or from about 0.1 inches to about 0.6 inches and/or from about 0.2 inches to about 0.45 inches, including all 0.01 inch increments between the recited ranges. The combination of these heights generally results in the cavity 42. The design of the surface of the cylinder 12 including the anvil block 16 and anvil bead 17 causes the air to flow over the anvil bead and into the cavity 42. The debris from the web 14 perforation process and/or upstream processes is then caught in this air stream and flows into the cavity 42 and away from the web 14.

Figure 4:
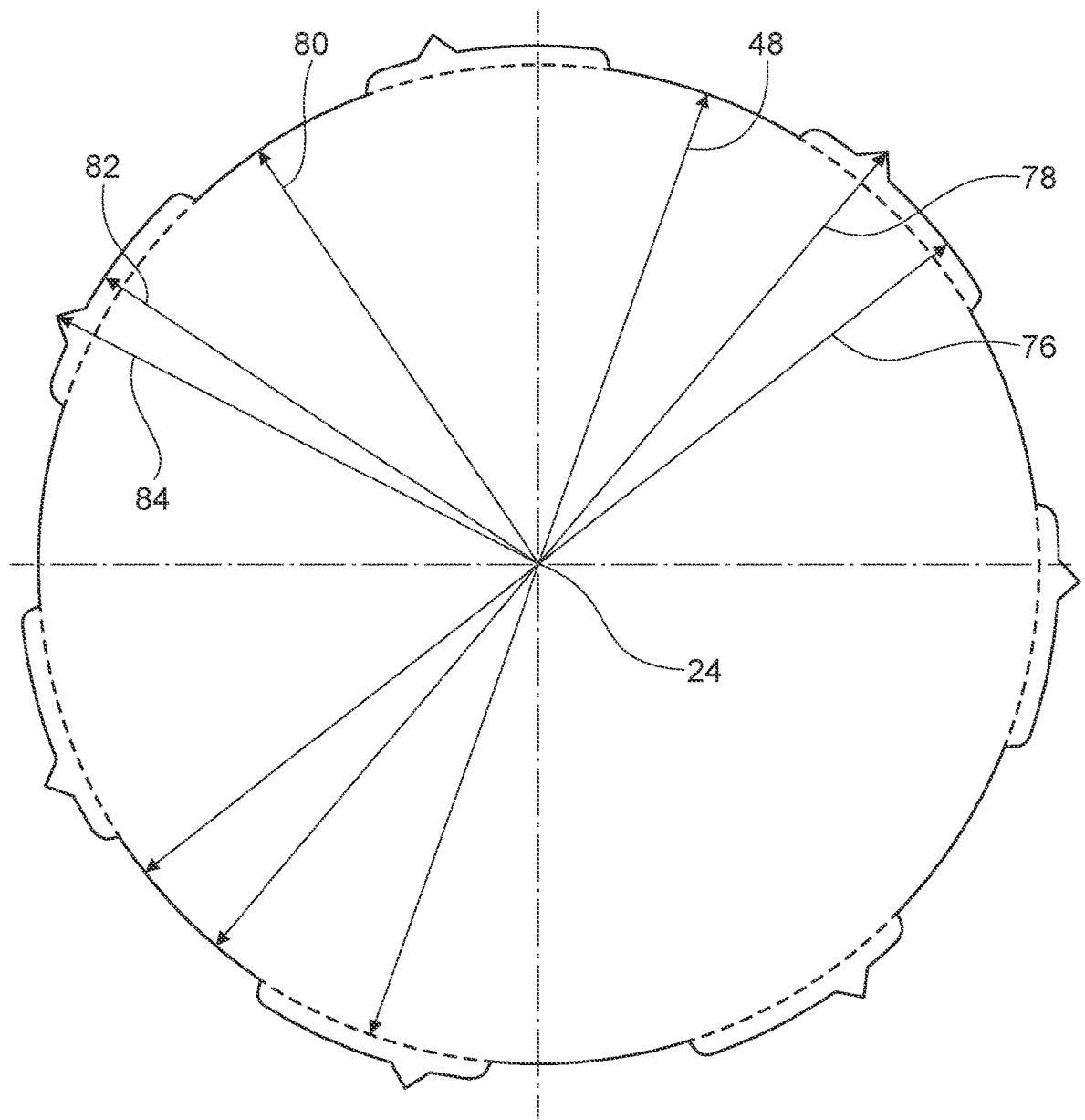
FIG. 4 is an end view of a cylinder including an anvil block and an anvil bead in accordance with one non-limiting form of the present disclosure.

More specifically, the difference in the diameters of the cylinder 12 including the anvil blocks 16 and anvil beads 17 aids in controlling the air flow and thus the debris from the perforating process. The difference in diameter or radii of the cylinder 12, anvil block 16 and anvil beads 17 determines, in part, the characteristics, such as the depth, of the cavity 42, which is used to control the debris generated in the perforating process. As illustrated in FIG. 4, the cylinder 12 may include a cylinder diameter 48 measured from the outer circumferential surface 30. The anvil block 16 may include an anvil block diameter 76 measured from the first anvil block surface 38 to the outer circumferential surface 30. Similarly, the anvil bead 17 may include an anvil bead diameter 78 measured from the anvil bead tip 46 to the outer circumferential surface 30. The difference of the cylinder diameter and the anvil block diameter may be from about 0.3 inches to about 1.2 inches. The difference of the cylinder diameter and the anvil bead diameter may be from about 0.4 inches to about 1.7 inches, and the difference of the anvil block diameter and the anvil bead diameter may be from about 0.2 inches to about 0.6 inches. Having the cylinder 12 designed such that the difference in diameters of the cylinder, anvil block, and anvil bead are as previously disclosed, the debris from the perforating process may be directed away from the web 14 and into the cavity 42. In some forms, the anvil bead diameter may be from about 8 inches to about 20 inches and/or from about 11 inches to about 15 inches; the anvil block diameter may be from about 7 inches to about 18 inches and/or from about 10 inches to about 15 inches; and the cylinder diameter may be from about 5 inches to about 16 inches and/or from about 8 inches to about 10 inches. It is to be appreciated that all 0.01 increments are included between the aforementioned recited ranges.

As previously stated, the ability to control the debris from the perforating process and/or upstream processes may also be obtained by having the appropriate comparison of radii of the cylinder 12, anvil block 16, and anvil bead 17. For example, as illustrated in FIG. 4, the cylinder 12 may include a cylinder radius 80 measured from the longitudinal cylinder axis 24 to the outer circumferential surface 30. The anvil block 16 may include an anvil block radius 82 measured from the first anvil block surface 38 to the longitudinal cylinder axis 24. Similarly, the anvil bead 17 may include an anvil bead radius 84 measured from the anvil bead tip 46 to the longitudinal cylinder axis 24. The difference of the cylinder radius and the anvil block radius may be from about 0.15 inches to about 0.6 inches. The difference of the cylinder radius and the anvil bead radius may be from about 0.2 inches to about 0.85 inches, and the difference of the anvil block radius and the anvil bead radius may be from about 0.1 inches to about 0.3 inches. It is again to be appreciated that all 0.01 increments are included between the aforementioned recited ranges. Having the cylinder 12 designed such that the difference in radii of the cylinder, anvil block, and anvil bead are as previously disclosed, the debris may be directed away from the web 14 and into the cavity 42.

Prior cylinder and anvil designs have failed to address the need to run at relatively high manufacturing speeds and to control the debris generated from the shaped perforation process and/or upstream processes. Prior designs are unable to obtain desired manufacturing run times due to, for example, premature breaking of web. The web is prone to failure when the debris is allowed to flow back towards the web and ultimately get captured on the web and interfere with the perforating process. The design described herein allows for sustained manufacturing run times and control of the debris in the process such that the debris generally moves away from the web and does not negatively impact the perforating process or other downstream processes.

Due to the relatively high manufacturing speeds, the anvil beads may be helically angled along the longitudinal cylinder axis, as illustrated in FIG. 3A. Each anvil bead may have a helix angle α measured from the longitudinal cylinder axis 24. The helix angle α may be from about 1 degrees to about 10 degrees and/or from about 2 degrees to about 8 degrees and/or from about 4 degrees to about 6 degrees, including all 0.1 degree increments between the recited ranges. The helix angle of the anvil beads may be determined, in part, due to the number of anvil blocks positioned about the circumference of the outer circumferential surface of the cylinder. The helix angle aids in minimizing vibration in the apparatus by maintaining contact points along the blade during processing. The helix angle may be increased or decreased to maintain a certain number of contact points between the blade and the anvil bead. For example, the helix and shape of the anvil bead may provide for from about 4 to about 10 contact points between the anvil bead and the blade. For example, the blade 26 may engage the helically mounted anvil bead such that the perforations 22 are created by a consecutive series of interaction points across the web 14 in a zipper-like manner. Further, helically mounting the anvil 16 may allow the anvil 16 to be in constant engagement with the blade 26.

The helix angle of the anvil beads also allows for the web 14 to be processed at relatively high manufacturing speeds, such as where the web traverses at a speed of from about 300 m/min to about 900 m/min and/or from about 500 m/min to about 750 m/min, including all 0.1 m/min increments between the recited ranges. As the web 14 is impacted by the helically angled anvil bead, the anvil bead imparts a shaped line of weakness that is substantially parallel to the cross direction CD. It is to be appreciated that the speed of the web and/or the anvil bead may be adjusted to change the direction and other properties of the lines of weakness. The speed of the anvil bead may be set with respect to the speed of the traversing web. The anvil bead may rotate at an overspeed of up to about 50% of the speed of the traversing web. The anvil bead may also be rotated at an underspeed with respect to the traversing web or at a substantially matched speed to the traversing web.

Further, the anvil bead 17 may be made from the same material as the anvil block 16 and/or the cylinder 12, or a different material. The anvil bead 17 may be made from a material that provides sufficient rigidity and life, strength and wear resistance, such that the anvil bead does not deflect or deflects minimally when engaging the blade and can sustain relatively prolonged manufacturing run time. The anvil bead 17 may be made from metal such as steel, aluminum, or tungsten carbide. The anvil bead 17 may also be made from non-metal such as ceramic, carbon fiber, or hard plastic. It is also to be appreciated that the anvil bead 17 may be made from two different materials. For example, the anvil bead body made be made from a first material and the anvil bead tip may be coated with a second material that is different than the first material. The second material may be applied by known methods such as laser cladding. As previously discussed, the anvil bead 17 operatively engages the blade 26. Thus, the anvil bead 17 should be made of a material that withstands continuous contact and wears advantageously for the perforating process. For example, the wear profile of the anvil bead may impact the quality of the perforation and, thus, the line of weakness imparted to the web 14. A material should be selected that allows for slow wear and a wear profile that does not negatively impact the line of weakness.

The anvil bead 17 may have an anvil bead cross sectional shape. The shape of the anvil bead may be such that the anvil bead is able to interact with the blade 26 to create lines of weakness. For example, the anvil bead may have a cross section shape that is substantially triangular shape or trapezoidal shape. The anvil bead may have a cross sectional angle 13 of from about 50 degrees to about 120 degrees and/or from about 70 degrees to about 100 degrees and/or from about 80 degrees to about 90 degrees, including all 0.1 degrees between each of the recited ranges. It is to be appreciated that the shape of the anvil bead may change as the anvil bead wears due to contact with the blade 26.

Figure 5A:
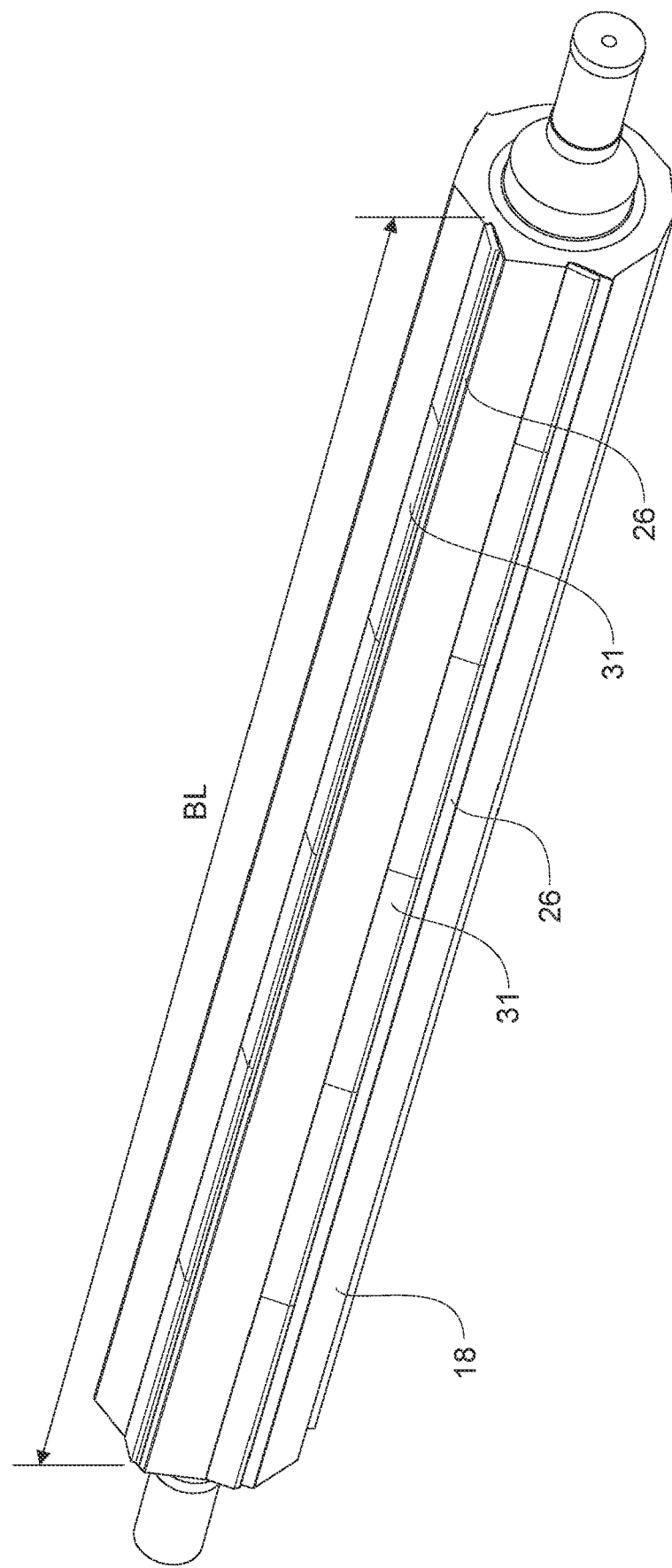
FIG. 5A is a perspective view of a support including a blade in accordance with one non-limiting form of the present disclosure.

Referring to FIGS. 5A and 5B, the support 18 may be positioned adjacent the cylinder 12. The support 18 may be formed from metal, such as steel or a steel alloy, or from some other material as would be known to those skilled in the art to be suitable as a structural support of perforating equipment. The support 18 may be in a block shape, a cylindrical shape, or another shape that would adequately support a blade 26. The support 18 may be placed in a fixed, non-moveable, non-rotatable position during contacting relationship with the anvil bead 17, independent of the shape of the support 18. In one example form, the support 18 may be a cylindrical shape or a substantially square shape such that when one or more blades 26 disposed on the outer surface wear or break, the support 18 may be rotated and fixed in a position so that a new blade 26 may be placed in contacting relationship with the anvil 16. Alternatively, the support 18 may be rotated and/or adjusted in and out of contacting relationship with the anvil 16 to easily and readily replace worn or damaged blades 26. A support 18 include more than one blade may also allow for various types of blades, such as blades having teeth with different spacing, to be quickly and easily placed into and out of operation.

The support 18 may include one or more blades 26 configured to operate in contacting engagement with the anvil bead 17. In some forms, the blade 26 interacts with the anvil bead in a shearing action. A portion of the blade 26 may be supported by the support 18 and another portion of the blade may be supported by a clamp 31. The clamp 31 and the support 18 act to hold the blade 26 in position, such that a portion of the blade 26 extends outward from the support 18 and is exposed for contact with the anvil bead. The blade may be held between the clamp 31 and the support such that the blade 26 may deflect during operative engagement with the anvil bead 17. This may be referred to as a flex-rigid configuration. This deflection and the inherent flexibility of the blade 26 allows for improved perforation reliability by being more forgiving to slight differences in machine tolerances. The support 18 may include a recessed portion, such that a portion of the support 18 is positioned under the blade 26 or opposite the first blade surface 58 but does not contact the blade 26 when the blade is inoperable. The portion of the support 18 disposed under the blade 26 but not contacting the blade 26, may be used to ensure that the blade does not deflect too much and/or to aid avoiding breaking the blade. The clamp 31 may be removably connected to the blade 26 and/or the support 18. This allows for timely replacement of worn and/or damaged blades. The blade 26 also extends in a direction substantially parallel to the longitudinal cylinder axis 24 or the cross direction CD. The blade 26 may have a total blade length BL that generally is as long as or longer than the width of the web such that the line of weakness extends from the first edge to the second edge of the web. The blade 26 may be a single blade or may include a plurality of blade segments.

The blade may be made from metal such as steel, tungsten, or any other hardened material that may withstand continued engagement with the anvil. The blade 26 may include a number of teeth extending along the total blade length. The spacing and number of teeth may be determined based on the desired number of perforations 22 and characteristics of the line of weakness in the web 14, such as disclosed in US Patent Publication Nos. 2014/0366695; 2014/0366702; and 2014/0370224. The tooth may be equally spaced along the total blade length or the teeth may be spaced at various increments along the total blade length.

Figure 5C:
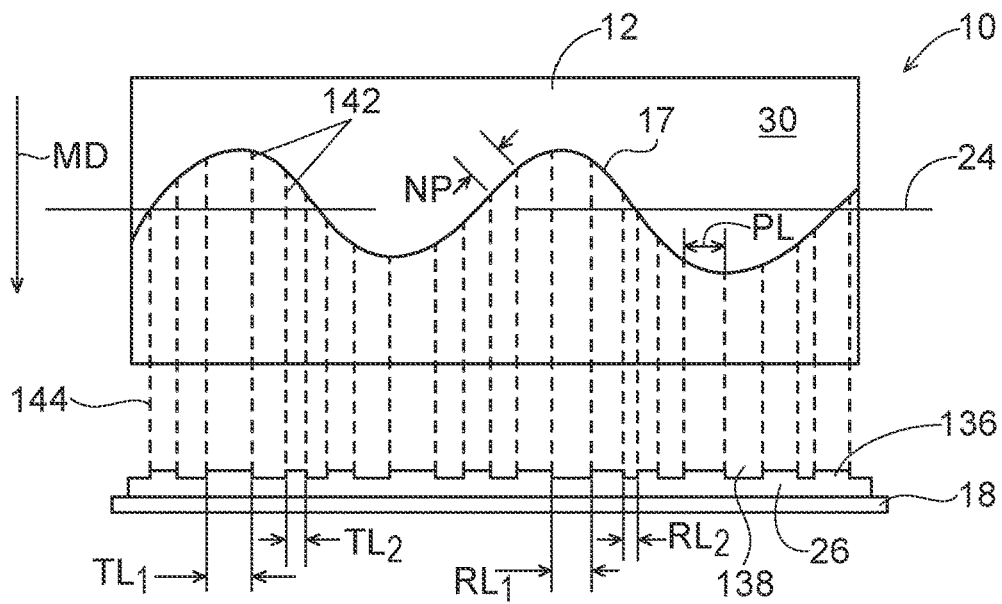
FIG. 5C is a schematic representation of a notched blade disposed on a support and a shaped anvil disposed in a cylinder in accordance with one non-limiting form of the present disclosure.
Figure 8:
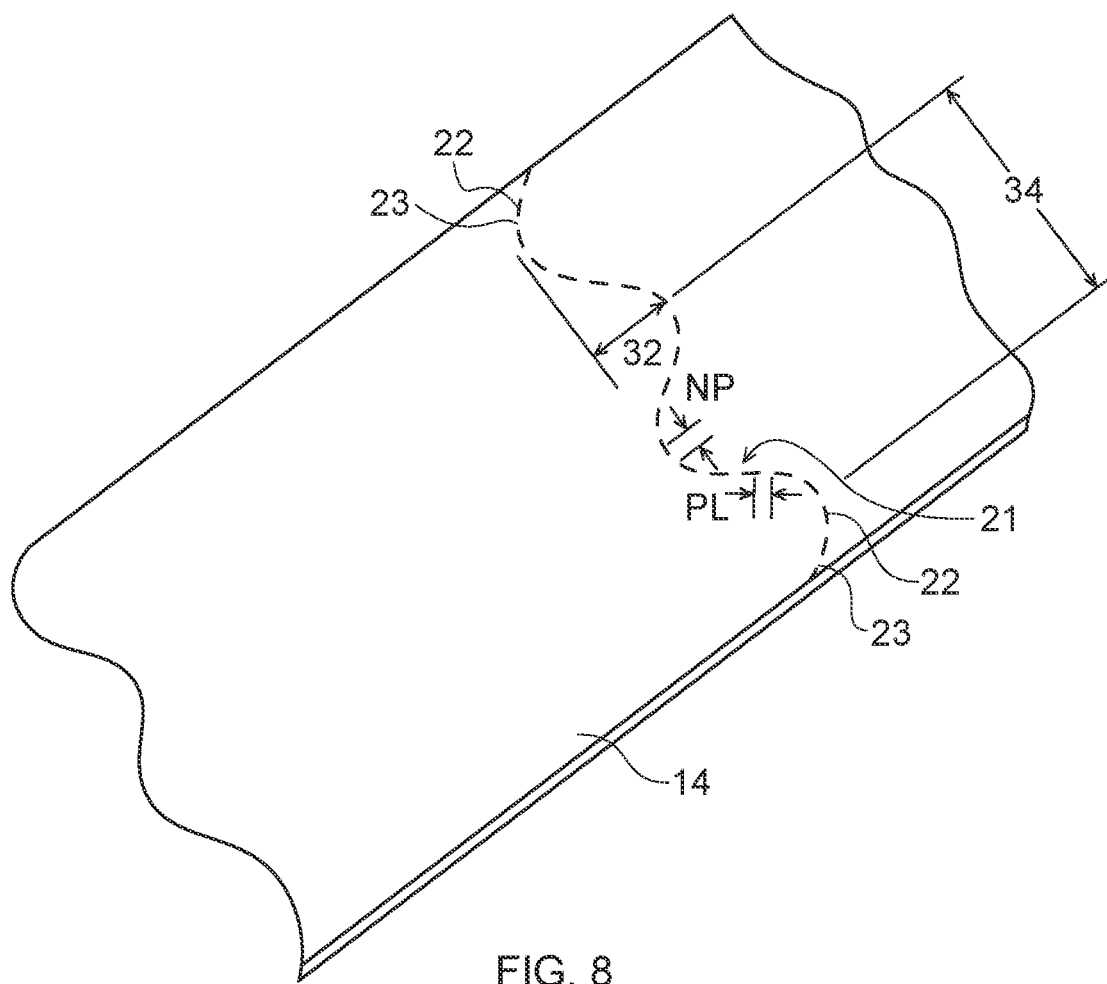
FIG. 8 is a perspective view of a web in accordance with one non-limiting form of the present disclosure.

Referring now to FIG. 5C, as can be understood by considering the present disclosure, a blade 26 and/or an anvil bead 17 can comprise one or more teeth 136 and one or more recessed portions 138 for making a line of weakness 21 comprising one or more perforations 22 and bond areas 23 in the web 14 (as shown in FIG. 8). In one form, the blade 26 disposed on the support 18 comprises one or more teeth 136 and one or more recessed portions 138, and the cylinder 12 comprises an anvil bead 17 in a wave-form shape. Due to the wave-form shape of the anvil bead 17, the rotation of the anvil bead 17 toward the blade 26, and the length of the one or more teeth 136 and the one or more recessed portions 138, a certain perforation length PL, as shown in FIGS. 5C and 5E, can be imparted to the web 14. For example, in one form, the length of the one or more teeth 136 and the one or more recessed portions 138 are uniform in length. The uniform length of the one or more teeth 136 and the one or more recessed portions 138 can result in non-uniform perforation lengths PL due to the curvilinear shape of the anvil bead 17. By "uniform" is meant that the lengths are substantially equal or within about 15% or less of each other. By "non-uniform" is meant that two or more lengths are not equal or are greater than about 15% of one another.

Therefore, in one form, a perforating apparatus 10 can be designed to make a line of weakness 21 comprising one or more perforations 22 having a substantially uniform perforation length PL. Alternatively, or in addition to uniform perforation lengths PL, the space between each perforation 22, i.e., the bond area 23, can have a non-perforation length NP, where the NP can be substantially uniform. As previously disclosed with respect to FIG. 1, the perforating apparatus 10 can comprise a cylinder 12 that rotates about a longitudinal cylinder axis 24 and a fixed support 18 between which a web 14 is advanced in the machine direction MD. More specifically in some forms, a wave-form shaped anvil bead 17 disposed on the cylinder 12 rotates and engages in contacting relationship with a straight, notched blade 26 disposed on the fixed support 18.

Again, the shaped form of the anvil bead 17 can be primarily dependent on the desired shape of the line of weakness 21 in the finished web 14. The blade is schematically depicted as a straight piece comprising one or more teeth 136 and one or more recessed portions 138 with variable lengths. The blade 26 and anvil bead 17 cooperate in contacting relationship to perforate the web. Still referring to FIG. 5C, each tooth 136 has a length TL and can be separated by a recessed portion 138 that also has a length RL. The hash marks 142 on the anvil bead 17 indicate the end positions of each tooth 136 based on the tooth length TL. Further, dashed lines 144 connect the hash mark 142 corresponding to each tooth 136 and, more specifically, the end positions of each tooth 136. If a uniform perforation length PL is desired, the tooth length TL and corresponding recessed length RL must account for the shape of the anvil bead 17. As shown in FIG. 5C, the hash marks 142 placed along the anvil bead 17 can be such that a uniform line of weakness is imparted to the web 14. However, as shown by following the dashed lines 144 from the blade 26 to the anvil bead 17, to achieve uniform perforation lengths PL and/or non-perforated lengths NP, the lengths of the teeth 136 (or recessed portions 138) must vary along the length of the blade 26. For example, tooth length $TL_1$ is longer than $TL_2$, as shown in FIG. 5C, yet each produce a perforation having substantially the same perforation length LP along the shaped anvil bead 17. Similarly, $RL_1$ is longer than $RL_2$, but such spacing or non-perforation portion produce substantially uniform non-perforated lengths NP (i.e., the length of the bond areas 23) along the shaped anvil bead 17.

Each tooth length TL can be individually predetermined such that its projected contacting relationship onto the anvil bead 17 delimits a length of the anvil bead 17 substantially equal to a desired perforation length PL in the web 14. Each recessed portion length RL is individually predetermined such that its projected relationship with respect to the anvil bead 17 delimits a length of the anvil bead 17 substantially equal to a desired bond area having non-perforated length NP in the web 14. For example, each tooth length TL and recessed portion length RL can be designed such that the lines of weakness 21 in the web 14 comprises perforations 22 that are longer at the edge of the web 14 compared to the perforations toward the middle of the web 14, or bond areas 23 that are shorter near the edge compared to the bond areas toward the middle of the web 14.

Figure 5D:
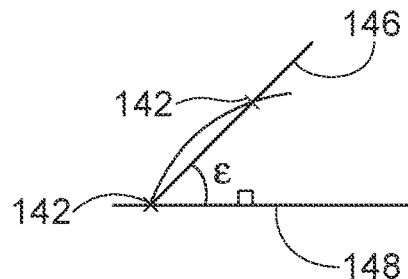
FIG. 5D is a schematic representation of a portion of an anvil indicating perforating length or non-perforating length to determine the tooth length or recessed portion length in accordance with one non-limiting form of the present disclosure.
Figure 5E:
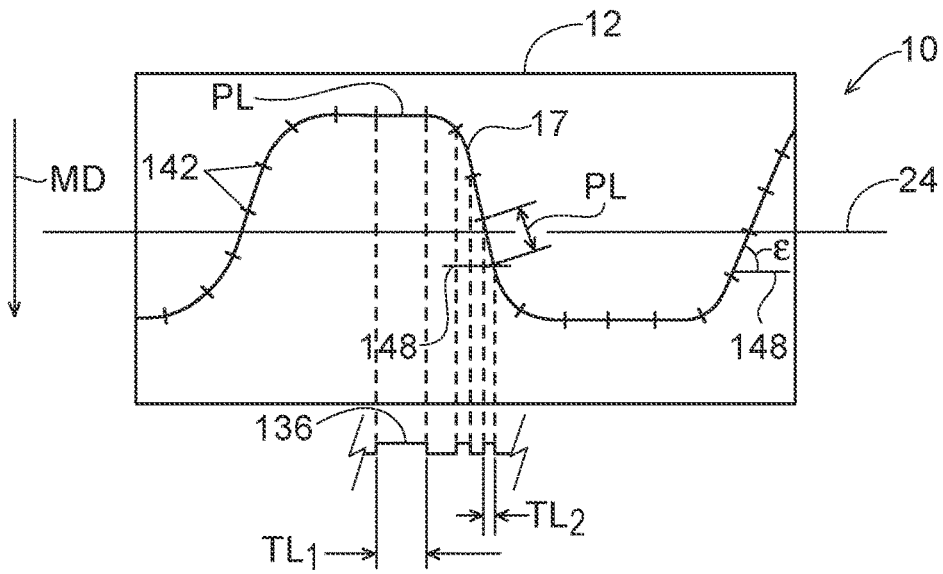
FIG. 5E is a schematic representation of a notched blade disposed on a support and a shaped anvil disposed in a cylinder in accordance with one non-limiting form of the present disclosure.

Referring now to FIGS. 5D and 5E, the tooth length TL and recessed portion length RL for an individual tooth 136 and recessed portion 138 on the blade 26 can be calculated. In one example form, the tooth length TL or the recessed portion length RL can be determined by first measuring or predetermining a desired perforation length PL or non-perforation length NP, as shown between adjacent hash marks 142. Next, connect adjacent harsh marks 142 with a straight line 146 and intersect the straight line 146 with a line 148 substantially parallel to the outside edge of the blade 26 forming an angle E. The straight line 146 should intersect the substantially parallel line 148 at a hash mark 142 so that the angle c is less than about 90 degrees. Assuming that the tooth 136 and/or recessed portion 138 has a surface that is substantially parallel to the outer surface 30 of the cylinder 12, the trigonometry of a right triangle can be used to calculate the tooth length TL and the recessed length RL. More specifically, still referring to FIG. 20, the tooth length TL or recessed portion length RL can be calculated as the desired perforation length PL or non-perforation length NP times the cosine of the angle E. Similarly, if a certain tooth length TL or recessed portion length RL is known, the perforation length PL or non-perforation length NP can be calculated using the geometry of a right triangle. Thus, the notch length NL and recessed portion length RL can be determined for any adjacent harsh marks 142. Additionally, one of ordinary skill in the art would understand that if the blade 26 was not parallel to the outer surface 30 of the cylinder 12, the resulting triangle would not have a right angle and more advanced trigonometry (e.g., the law of sines, law of cosines, and law of tangents) could be used to determine the angles and lengths.

The blade 26 may be configured to oscillate in the cross direction CD and/or substantially parallel to the longitudinal cylinder axis 24 during the perforation process. The blade 26 oscillates by moving a first direction, substantially parallel to the cross direction, by a predetermined amount and, subsequently, moving in a second direction, opposite the first direction by another predetermined amount. The blade 26 may oscillate by the same distance in both the first direction and the second direction, or the blade may oscillate by a different distance in the first direction and the second direction. The predetermined amount the blade may oscillate may depend, in part, on the shape of the line of weakness that is to be imparted to the web and/or the shape of the anvil bead. For example, the shape of the anvil beads may include a pattern that repeats a number of times along the central longitudinal axis. Each of these repeat patterns may include a pattern distance. The pattern distance is the distance from the end of a preceding pattern or the beginning of a new pattern to the beginning of the subsequent pattern or the end of the pattern. The oscillation of the blade may depend on this pattern distance. The blade may oscillate a predetermined distance of from about 1% to about 100% of the pattern distance. For example, for a sinusoidal wave pattern having a pattern distance or wavelength of 1.23 inches, the blade may oscillate from about 0.1 inches to about 0.23 inches in the cross direction CD. The oscillation of the blade 26 aids in reducing wear on the blade during processing and allows for the blade to wear more uniformly than if the blade was kept stationary. Examples of an oscillating blade are disclosed in US Patent Publication Nos. 2016/0271820; 2016/0271823; and 2016/0271824.

Figure 6A:
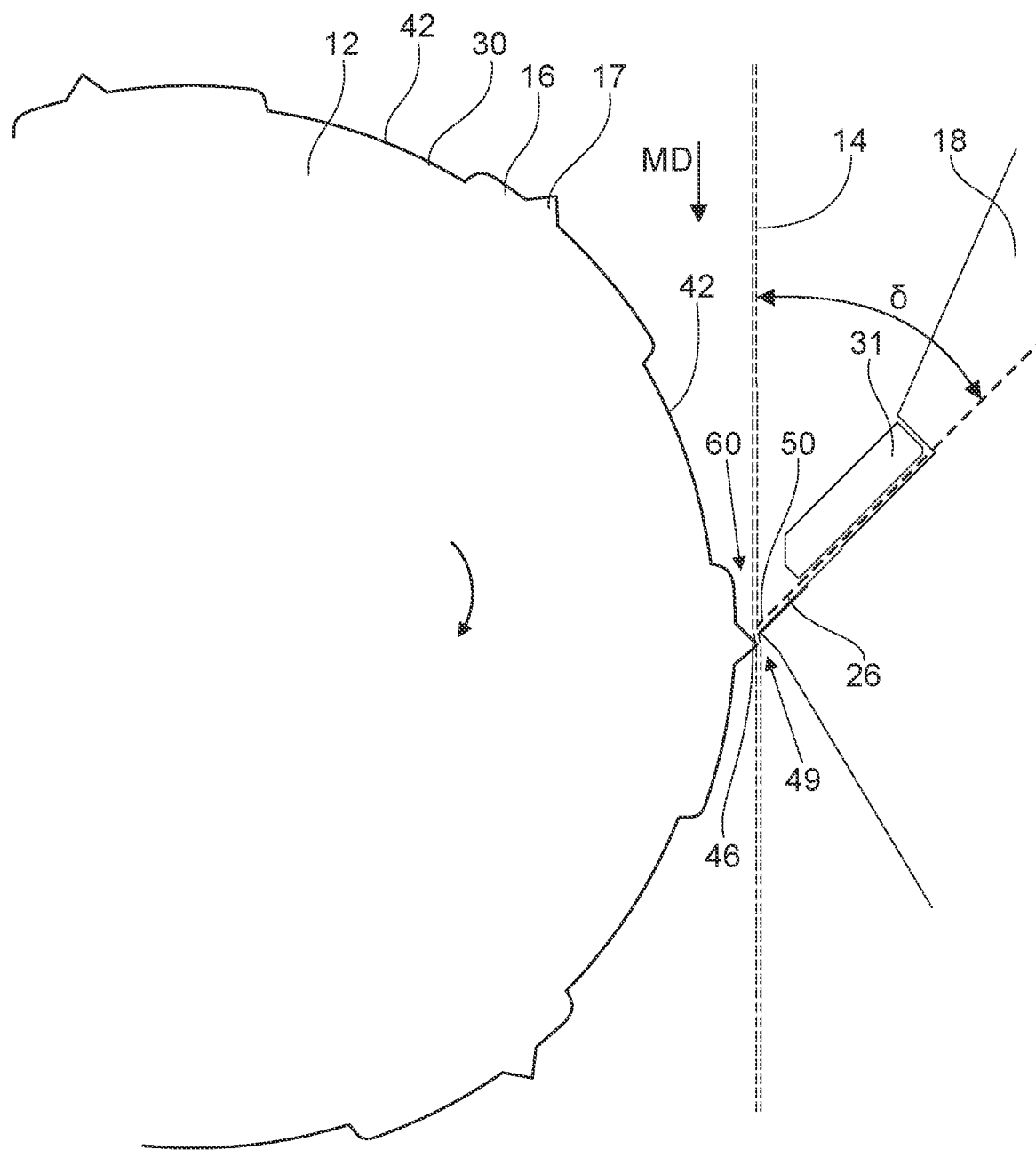
FIG. 6A is a partial side view of a cylinder and a support and a web traversing therebetween in accordance with one non-limiting form of the present disclosure.
Figure 6B:
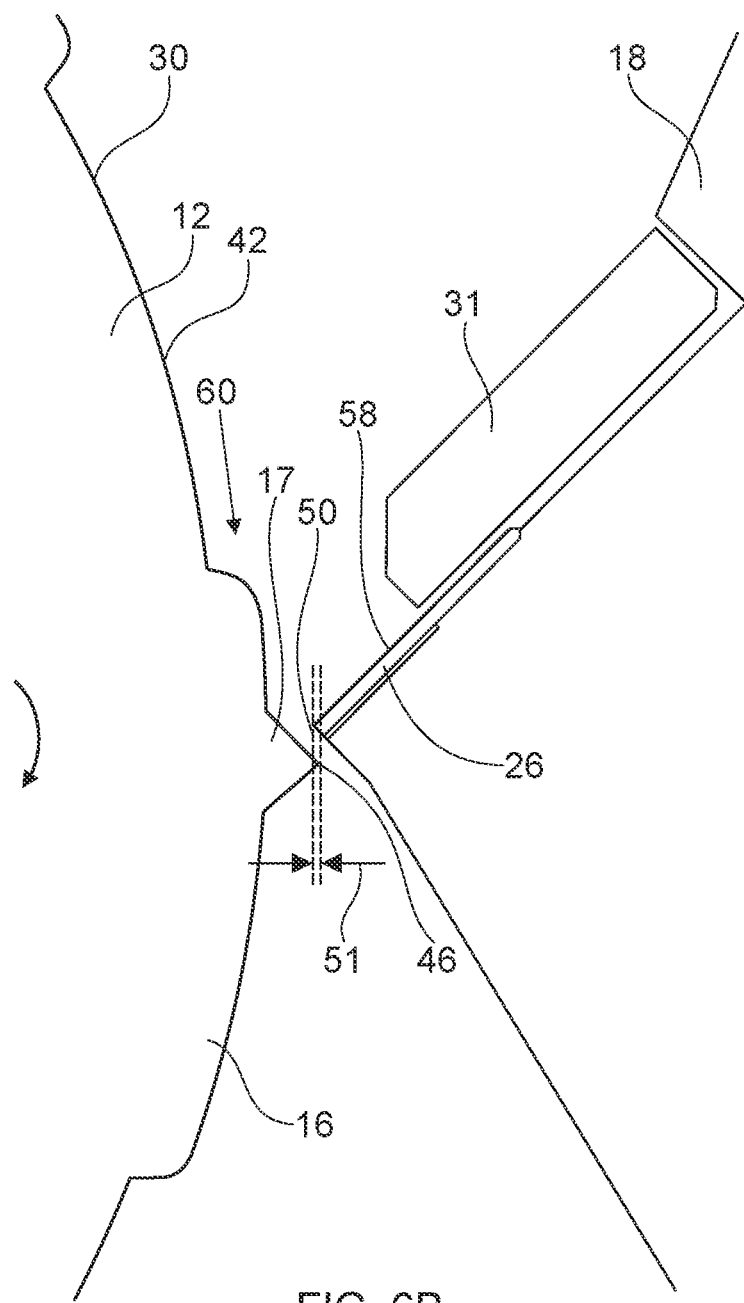
FIG. 6B is a partial side view of a cylinder and a support in accordance with one non-limiting form of the present disclosure.

As illustrated in FIGS. 6A and 6B, the web 14 traverses between the blade 26 and the anvil bead 17. As previously discussed, the anvil bead 17 and the blade 26 operate in contacting relationship to perforate the traversing web 14. The point at which the anvil bead 17 contacts the blade 26 is the nip 49. More specifically, the cylinder 12 rotates about the longitudinal cylinder axis 24 resulting in the anvil block 16 and the anvil bead 17 also rotating about the longitudinal cylinder axis 24. The blade 26 is positioned such that a tip of blade, the blade tip 50, overlaps the anvil bead tip 46 by an overlap distance 51, as illustrated in FIG. 6B. The overlap distance 51 is measured from the blade tip 50 to the anvil bead tip 46 in a direction substantially parallel to the cross direction. The overlap distance 51 may be from about 0.002 inches to about 0.3 inches. If the overlap distance becomes too small and the blade 26 fails to operatively engage the anvil bead 17, the web 14 is not adequately perforated and the resulting characteristics of the line of weakness are likely to be unacceptable from both a manufacturing standpoint and from a consumer acceptance/use standpoint. By decreasing the overlap distance between the blade 26 and the anvil bead 17, the perforations 22 generally become less pronounced, less visible, shorter, and the bond areas 23 generally become wider and thus stronger. If the overlap distance becomes too large such that the blade 26 and the anvil bead 17 have a significant overlap, the web 14 may be unable to traverse through the nip and the web 14 may be separated such that the line of weakness fails during processing and the web splits along the line of weakness or adjacent to the line of weakness. By increasing the overlap between the blade 26 and the anvil bead 17, the perforations 22 generally become more pronounced, more visible, and longer. Maintaining the overlap distance as previously specified and avoiding too much or too little overlap, allows the web 14 to be perforated and a line of weakness to be formed such that the line of weakness is preserved during processing and yet provides ease of use to consumers. The overlap distance may be adjusted, for example, by moving one of the bade 26, the cylinder 12, and/or the support 18.

As illustrated in FIG. 1, the web 14 includes a longitudinal web axis 52, a first side edge 54, and a second side edge 56 opposite the first side edge 54. The web 14 traverses between the blade 26 and the anvil bead 17 such that the longitudinal web axis 52 is substantially parallel to the machine direction or, stated another way, the longitudinal web axis 52 is substantially tangential to the outer circumferential surface 30 of the cylinder 12, as illustrated in FIG. 6A. Further, in some forms, the blade 26 may be positioned with respect to the traversing web 14. More specifically, the blade 26 incudes a blade tip 50 and a first blade surface 58. The first blade surface 58 may be exposed such that the anvil bead operatively engages a portion of the first blade surface 58 and the blade tip 50. The blade 26 is positioned such that the blade tip 50 and blade surface 58 is at a blade angle δ. The blade angle δ is measured from the blade to the surface of the traversing web 14 or a plane that is parallel to the machine direction MD. The blade angle δ is from about 20 degrees to about 60 degrees and/or from about 30 degrees to about 55 degrees and/or from about 45 degrees to about 50 degrees, including all 0.1 degree increments between the recited ranges.

As illustrated in FIGS. 6A and 6B, due to the position of the blade 26 and the profile of the cylinder including the anvil block and anvil bead, the traversing web 14 has a relatively larger gap 60 than previous designs through which the web traverses. Further, the anvil bead height 44 also provides added clearance in the gap 60. This gap 60 allows for imperfections in the web 14 to traverse between the anvil bead and the blade without causing failure in the web 14, such as a tear. For example, the web 14 may comprise a large deposit of pulp in a particular area. This build-up of pulp causes the web 14 to be thicker in this area. The increased thickness may be unnoticeable to a consumer and may not adversely affect the finished product. However, the increased thickness may result in manufacturing issues. These issues are relatively avoided for the perforating process due to the relatively larger gap 60 between the blade 26 and the anvil bead 17.

It is also to be appreciated that the gap 60 allows for strain on the web to be maintained during the manufacturing process. The traversing web 14 may be strained in the machine direction at a strain of from 0% to about 15% and/or from about 0.5% to about 10% and/or from about 3% to about 8%, including all 0.1% increments between the recited ranges. This strain needs to be maintained on the web 14 for downstream processing such as winding the web into a roll or separating the web along lines of weakness. The gap 60 present in the perforating apparatus allows for the strain on the web to be maintained during the perforating process. Past processes required the strain in the web to be reduced prior to traversing through the perforating operating because a portion of the web needed to be disposed on the cylinder during the perforating process for the process to create a line of weakness in the web. By contrast, the gap 60 and, thus, the position of the anvil bead 17 with respect to the blade 26 allows for sufficient clearance between the anvil bead 17 and the blade 26 such that the web may be perforated without additional strain being placed on the web such that the web breaks or tears.

The perforating apparatus previously described is configured to impart a shaped line of weakness onto a traversing web 14. The shaped line of weakness on the web 14 is due in part to the design of the anvil bead, the helix angle, and the speed of the web 14 with respect to the speed of the anvil bead 17. The web 14 may traverse at a web speed, as previously described. The anvil bead 14 may be rotated at a speed greater than, less than, or equal to the speed of the traversing web 14. The speed at which the web 14 and the anvil bead 14 traverse may change the characteristics of the line of weakness on the web 14. For example, the shape of the line of weakness may differ from the shape formed by the anvil beads. For a line of weakness having a sinusoidal shape, the wavelength and/or amplitude of the shaped line of weakness may be different than the wavelength and/or amplitude of the shape formed by the anvil beads. Further, the distance between adjacent lines of weakness on the web 14 may be changed based on the speed of the anvil beads and the traversing web. For example, the speed of the anvil bead may be greater than the speed of the web, oversped, to produce adjacent lines of weakness having a distance between adjacent lines of weakness that is reduced, as compared to having the anvil bead and the web traversing at the same speed. Similarly, the speed of the anvil bead may be less than the speed of the web, undersped, to produce adjacent lines of weakness having a distance between adjacent lines of weakness that is increased, as compared to having the anvil bead and the web traversing at the same speed.

Referring to FIG. 7, as the anvil bead 17 interacts with the blade 26 to perforate the web 14, debris is generated from the perforating process and/or upstream processes. This debris may interfere with the perforating process and result in failure of the web 14 by tearing, incomplete perforations, and/or a line of weakness that is not consumer acceptable. As previously discussed, the cylinder 12, anvil block 16, and anvil bead 17 create a profile that controls the flow of the debris. As the cylinder 12 rotates about the longitudinal cylinder axis 24 air flows over the outer circumferential surface 30. The air flow is generally in the direction of rotation of the cylinder 12, as illustrated by the arrows in FIG. 7. This air flow is interrupted by the engagement of the anvil bead 17 with the blade 26 at the nip 49. This interruption causes the air flow to become turbulent and to carry the debris in an unpredictable pattern that may result in debris interfering with the perforating process and damaging the web 14. The design of the cylinder 12 including the anvil block 16 and the anvil bead 17 controls the air flow by creating a low pressure zone 86 in the wake of the anvil bead 17. This low pressure zone defines a boundary layer 64. The boundary layer 64 extends between radially positioned, adjacent anvil bead tips 46. The low pressure zone 86 encourages the debris into the boundary layer 64. The boundary layer 64 is maintained as the cylinder traverses about the longitudinal cylinder axis and the debris is transferred into the cavity 42, as previously discussed. More specifically, the cylinder 12 may include a pre-perforation zone 62 which is the area of the cylinder prior to the web being perforated. The cavity 42 of the cylinder 12 in the per-perforating zone allows for more air to be controlled prior to perforating. The cavity 42 allows for a relatively greater quality of air to be encouraged to stay adjacent to the outer circumferential surface 30 of the cylinder 12, within the boundary layer 88. The debris is controlled such that the debris flows into the cavity and/or adjacent the outer circumferential surface and thus, the debris that interferes with the web and/or the perforation process is minimized. The debris is controlled such that the web and the line of weakness are not adversely impacted. Thus, in the per-perforation zone, the debris is generally channeled toward the outer circumferential surface 30 and into the cavity 42 and away from the web 14.

The boundary layer 64 of air flow may be present between adjacent anvil beads spaced radially about the outer circumferential surface. This boundary layer 64 of air flow may be present over the cavity defined by the cylinder, anvil blocks, and anvil beads. For example, a boundary layer 64 is formed between a first anvil bead 68 and a radially adjacent second anvil bead 72. The boundary layer encompasses the cavity 42 between the first anvil block 66 and the second anvil block 70. A web 14 traverses through the nip and the first anvil block 66 and the second anvil block 70 traverse in the per-perforation zone 62. The boundary layer 64 is formed as the first anvil bead 68 and the second anvil bead 72 traverse about the longitudinal cylinder axis. Debris is formed by perforating the web 14. The debris is encouraged to travel away from the web and into the boundary layer 64 via the low pressure zone created on the wake of the anvil bead. The debris is then contained within the boundary layer 64 and the cavity 42. The debris is held in this area between the first and second anvil beads and the cavity, until the boundary layer 64 is broken. The boundary layer begins to be broken when the first anvil bead 68 engages the blade 26 at the nip 49. The boundary layer generally gets broken by the disruption in air flow caused by the operative engagement of the anvil bead and the blade. The boundary layer remains effective in the pre-perforation zone until the second anvil bead 72 contacts the blade 26. The first anvil block and bead traverse into the post-perforation zone 74 and the second anvil block 70 and second anvil bead 72 continue to traverse and the second anvil bead 72 operatively engage the blade 26. At this point, the boundary layer is fully broken. Due to the broken boundary layer and centrifugal force, the debris is expelled from the area between the first anvil bead and the second anvil bead and the cavity and falls away from the outer circumferential surface 30 of the cylinder 12. The debris is expelled in the post-perforation zone 74. Thus, the design of the cylinder, anvil blocks, and anvil beads allows for sustained continuous manufacturing time and to produce a final product having its intended properties due, in part, to the control of debris.

After exiting the perforation apparatus, the web 14 may traverse to other downstream processes, such as winding, cutting, and sealing.

The process for perforating the web includes rotating the cylinder 12 about the longitudinal cylinder axis 24. The cylinder 12 includes an outer circumferential surface 30 that substantially surrounds the longitudinal cylinder axis 24. The outer circumferential surface 30 includes a plurality of recessed portions 36. These recessed portions 36 may be positioned both longitudinally and radially about the outer circumferential surface 30. The recessed portions 36 are configured to accept an anvil block 16 or two or more anvil block segments. The anvil blocks 16 may be removably connected with the recessed portions 36. The anvil blocks 16 may be offset from one another in the longitudinal direction. Further, the anvil blocks may be positioned radially about the outer circumferential surface 30 and cavities are formed between adjacent anvil blocks. These cavities 42 are formed by the anvil blocks 16 extending radially above the outer circumferential surface 30 of the cylinder 12. Each of the anvil blocks 16 may include an anvil bead 17. The anvil bead 16 may be removably connected to the anvil block 16 or the anvil bead 16 and the anvil block 17 may be manufactured together. The anvil beads 16 together form a shape extending along the longitudinal cylinder axis 24. The anvil beads operatively engage the blade 26. The blade 26 may be supported by a support 18. The blade may include a single blade or a plurality of blades. The blade 26 may be stationary or the blade 26 may oscillate in a direction substantially parallel to the cross direction. The web 14 is fed between the anvil bead 17 and the blade 26 to form perforations. The perforations imparted to the web 14 form a shaped line of weakness. However, debris is generated from perforating the web and/or upstream processes. This debris is controlled due to the shape of the cylinder in combination with the anvil block and the anvil bead. As previously discussed, a cavity is formed between adjacent anvil blocks, including anvil beads. Due to the air flow created by the cavity, the debris is drawn into the cavity and away from the web. This substantially minimizes any adverse effect the debris may have on the web and/or the perforating process. The debris is held in the cavity until the cavity is rotated to a position downstream of the nip, where the anvil bead engages the blade. Once the cavity is downstream of the nip, the debris may be expelled from the cavity and any other debris may be pushed away from the outer circumferential surface 30 of the cylinder 12. Due the aforementioned process, the strain on the web is maintained. The machine direction strain may be from about 0.5% to about 10%. Further, the web may traverse through the nip at a web speed from about 300 m/min to about 900 m/min and/or from about 500 m/min to about 700 m/min, including all 0.1 increments between the recited ranges. The anvil bead rotates at an anvil bead speed greater than, less than, or equal to the web speed.

Is it also to be appreciated that the above description applies to either of the recited configurations. In some forms, the cylinder 12 may comprise a shaped blade 26 and the support 18 may comprise a straight, linear anvil bead 17, not shown. Likewise, in some forms, the cylinder 12 may comprise a shaped blade 26 and the support 18 may comprise a straight, linear blade.

It is to be further appreciated that the apparatuses and methods detailed herein may be configured in various ways to include various features associated with perforating substrates. For example, the apparatuses and methods herein may be adapted to allow for selectively adjusting and maintaining positions of cutting surfaces used to create lines of weakness for rolled products, such as disclosed in, for example, U.S. Patent Application Ser. No. 62/729,441 entitled "METHOD AND APPARATUS FOR ADJUSTING AND MAINTAINING A POSITION OF A CUTTING SURFACE OF A PERFORATING APPARATUS", filed on Sep. 11, 2018.

A non-limiting example form of a web 14 with the shaped line of weakness produced by the processes of the present disclosure is depicted in FIG. 8. The web 14 can comprise one or more shaped (e.g., curvilinear) lines of weakness 21. The line of weakness 21 can be substantially the same, or similar to, the curvilinear shape as that of the anvil 16, as was discussed in more detail above. The shaped line of weakness 21 can comprise a plurality of perforations 22 and bond areas 23 between adjacent perforations 22. Each of the plurality of perforations 22 has a perforation length PL that can be substantially the same or different with respect to each other perforation length PL across the shaped line of weakness 21. Similarly, between each adjacent perforation 22 can be a bond area 23 having a non-perforation length NP that can be substantially the same or different relative to other and/or adjacent bond areas. The term "substantially" can refer to the degree of similarity between two comparable units, and, more specifically, refers to those comparable units that are within about 15% of one another. Further, the plurality of perforations 22 can protrude through one or more plies of the web 14.

As previously stated, each of the plurality of perforations has a perforation length and each of the bond areas has a non-perforation length (i.e., length of the bond area 23). In one example form, at least two of the perforation lengths are substantially equal. In another example form, at least two of the non-perforation lengths are substantially equal. In another example form, at least two of the perforation lengths are substantially unequal. In another example form, at least two of the non-perforation lengths are substantially unequal. In yet another example form, at least two of the non-perforation lengths are substantially equal and at least two of the perforation lengths are substantially equal. In yet another example form, at least two of the non-perforation lengths are substantially unequal and at least two of the perforation lengths are substantially unequal. In still another example form, the shaped line of weakness 21 can comprise at least one wavelength 34. In still another example form, the shaped line of weakness 21 can comprise at least one wavelength 34, and the one or more perforations 22 and bond areas 23 can be imparted to the web 14 such that the perforation lengths PL near the edge of the web 14 are longer than the perforation lengths PL near the middle of the web 14 and/or the non-perforation lengths NP are shorter near the edge of the web 14 and longer near the middle of the web 14. Similarly, the perforations 22 and bond area 23 can be imparted to the web 14 such that the perforation lengths PL are substantially the same at the crest and trough of the wavelength 34 and different between the crest and the trough of the wavelength 34. Further, the perforations 22 and bond areas 23 can be imparted to the web 14 such that the non-perforation lengths NP are substantially the same length at the crest and trough of the wavelength 34 and a different length between the crest and the trough of the wavelength 34.

As mentioned in the Background above, previous attempts to run commercial-scale production of a web of rolled sanitary tissue products 14 that include a shaped line of weakness 21 have been unsuccessful. Early test-stand development work showed promise, but the scale-up to high speed, commercial-scale converting lines was met with failure. Previous approaches failed because they did not consider the impacts of the high speeds of the commercial-scale converting equipment, the dust hygiene implications on such equipment, the tight tolerances between such equipment (e.g., spacing between roll body surfaces of the converting equipment), the web sheet aerodynamics, the large web sheet widths, and the extremes of CD property variation of the sanitary tissue webs being converted, as well as other factors. Accordingly, previous commercial-scale production attempts were plagued by short run times of just a few minutes due to web breaks, an inability to reach or maintain target production rates, an inability to reach target web tensions without web breaks, and an inability to wind rolls to target compressibility or firmness (e.g., the sanitary tissue rolls were mushy and would not be acceptable to consumers, nor run well on downstream high speed converting and packaging equipment). Net, from a commercial-scale converting line perspective, previous attempts to impart a shaped line of weakness feature 21 on sanitary tissue products were dramatically unsuccessful based upon their inability to meet process reliability and product quality requirements.

The inventors have unexpectedly found, while not wishing to be bound by theory, that process reliability on high speed commercial-scale converting lines and sanitary tissue web property targets and roll property targets (e.g., parameters to indicate one hand tearing dispensability, roll firmness, roll compressibility, etc.) may be simultaneously achieved by appropriately balancing the shaped line of weakness 21 design and/or the design of the process of creating the shaped line of weakness and/or the design of the equipment employed to produce the shaped line of weakness. This balance may be represented by a Line of Weakness Performance Factor ("LWP Factor"). The LWP Factor is defined as the ratio of the Full Sheet Tensile Strength divided by the Full Sheet Average Trapezoidal Tear Strength. The Line of Weakness Performance Factor is shown in the illustration below:

$$LWP\ Factor = \frac{Full\ Sheet\ Tensile\ Strength\,(g/in)}{Full\ Sheet\ Average\ Trapezoidal\ Tear\ Strength(g)}$$

The numerator of the LWP Factor may reflect the requirements for running a reliable and properly web tensioned high-speed converting process as it may represent the tendency for the substrate to experience a sheet break during the converting process. The denominator may be indicative of the shaped line of weakness resistance to tear properties meeting the needs of a consumer for reliable, one hand tearing dispensability. The inventors have unexpectedly discovered delivering inventive levels of the LWP factor yields a reliable and properly web tensioned high-speed converting process, substrate, and roll of substrate, that delights consumers with its reliable, one hand tearing dispensability and roll firmness. Inventive levels of the LWP Factor may be achieved through appropriately balancing the shaped line of weakness 21 design and/or the design of the process of creating the shaped line of weakness and/or the design of the equipment employed to produce the shaped line of weakness, and combinations thereof, as described herein.

In addition, after a shaped line of weakness 21 has been torn by a consumer, there is a series of micro-failures or micro-tears on the separated shaped line of weakness of a sheet. These micro-failures or micro-tears are where the bond areas 23 of the original shaped perf line failed upon dispensing or tearing of a sheet from a roll. The areas where the micro-failures or micro-tears occur, ("failure zones") generally may comprise free fiber ends or loosened fibers extending beyond a smooth curvilinear line running through or fitted to the original shaped line of weakness across the tissue sheet. A measure of the extent of free fiber ends per sheet and/or the free fiber ends per unit length of shaped perf on the original sheet may be viewed by consumers as enhancing the perceived or visual softness of the tissue with the shaped line of weakness 21, the roll of tissue with the shaped line of weakness, and/or the shaped line of weakness failure line itself. Hence, the highest performance tissue product in the perceived views of a consumer may have enhanced levels of free fiber ends per sheet and/or the free fiber ends per unit length of shaped line of weakness. Inventive levels of free fiber ends per sheet and the free fiber ends per unit length of shaped line of weakness may be achieved through the shaped line of weakness design and/or the design of the process of creating the shaped line of weakness and/or the design of the equipment employed to produce the shaped line of weakness, and combinations thereof, as described herein.

Further, a shaped line of weakness 21 on a sanitary tissue paper product, for example, allows consumers to more easily grasp and dispense the exposed sheet of the product due to the shaped line of weakness 21 creating a series of tabs or a visually identifiable edge. Still further, the shaped line of weakness 21 can allow consumers to readily distinguish a product from other manufacturer's products by having a visually distinctive perforation, such as one that complements an emboss or print pattern. FIGS. 8 A-Q illustrate various exemplary shapes of the curvilinear line of weakness 21 that can be imparted to the web. One of ordinary skill in the art based on the aforementioned disclosure would understand that the shape of the line of weakness 21 is due in part to the shape of the shaped anvil bead 17 or shaped blade 26 disposed on the rotating cylinder 12. Thus, the shapes shown in FIGS. 8 A-Q could also be the profiles of the shaped anvil bead 17 or shaped blade 17 disposed on the rotating cylinder 12 and used to generate webs with shaped lines of weakness as described herein. Generally, the profiles depicted in FIGS. 8 A-Q can be described as exhibiting a sinusoidal shape, as being a group of two or more linear elements each connecting at a single inflection point with an adjacent linear element, or a combination of curvilinear and linear elements.

The below parameter values and ranges below were measured and/or estimated with regard to sanitary tissue products, and rolls of sanitary tissue products, that were produced using the processes detailed herein. Unless identified as a sheet or roll of sanitary tissue product with a traditional straight, linear line of weakness parallel to the CD direction of the substrate, the sanitary tissue products that are measured and/or estimated below include a shaped line of weakness as disclosed herein.

The sanitary tissue products of the present disclosure may have a basis weight of from about 15 g/m² (9.2 lbs/3000 ft²) to about 120 g/m² (73.8 lbs/3000 ft²) and/or from about 15 g/m² (9.2 lbs/3000 ft²) to about 110 g/m² (67.7 lbs/3000 ft²)

and/or from about 20 g/m² (12.3 lbs/3000 ft²) to about 100 g/m² (61.5 lbs/3000 ft²) and/or from about 30 (18.5 lbs/3000 ft²) to 90 g/m² (55.4 lbs/3000 ft²)), specifically reciting all 0.1 g/m² increments within the recited ranges. In addition, the sanitary tissue products of the present disclosure may exhibit a basis weight from about 40 g/m² (24.6 lbs/3000 ft²) to about 120 g/m² (73.8 lbs/3000 ft²) and/or from about 50 g/m² (30.8 lbs/3000 ft²) to about 110 g/m² (67.7 lbs/3000 ft²) and/or from about 55 g/m² (33.8 lbs/3000 ft²) to about 105 g/m² (64.6 lbs/3000 ft²) and/or from about 60 g/m² (36.9 lbs/3000 ft²) to 100 g/m² (61.5 lbs/3000 ft²), specifically reciting all 0.1 g/m² increments within the recited ranges.

The sanitary tissue products of the present disclosure may have a caliper of between about 5 mils and about 50 mils, or between about 7 mils and about 45 mils, or about 9 mils and about 40 mils, specifically reciting all 0.1 mil increments within the recited ranges.

The sanitary tissue products of the present disclosure may have a density of less than about 0.60 g/cm³ and/or less than about 0.30 g/cm³ and/or less than about 0.20 g/cm³ and/or less than about 0.10 g/cm³ and/or less than about 0.07 g/cm³ and/or less than about 0.05 g/cm³ and/or from about 0.01 g/cm³ to about 0.20 g/cm³ and/or from about 0.02 g/cm³ to about 0.10 g/cm³, specifically reciting all 0.01 g/cm³ increments within the recited ranges.

The toilet tissue products of the present disclosure may exhibit a total dry tensile strength of greater than about 59 g/cm (150 g/in) and/or from about 78 g/cm (200 g/in) to about 394 g/cm (1000 g/in) and/or from about 98 g/cm (250 g/in) to about 335 g/cm (850 g/in), specifically including all 0.1 g/cm increments between the recited ranges. In addition, the sanitary tissue product of the present disclosure may exhibit a total dry tensile strength of greater than about 196 g/cm (500 g/in) and/or from about 196 g/cm (500 g/in) to about 394 g/cm (1000 g/in) and/or from about 216 g/cm (550 g/in) to about 335 g/cm (850 g/in) and/or from about 236 g/cm (600 g/in) to about 315 g/cm (800 g/in), specifically including all 0.1 g/cm increments between the recited ranges. In one example, the toilet tissue product of the present disclosure exhibits a total dry tensile strength of less than about 394 g/cm (1000 g/in) and/or less than about 335 g/cm (850 g/in), specifically including all 0.1 g/cm increments between the recited ranges. In addition, the toilet tissue products of the present disclosure may exhibit a total dry tensile strength of greater than about 196 g/cm (500 g/in) and/or greater than about 236 g/cm (600 g/in) and/or greater than about 276 g/cm (700 g/in) and/or greater than about 315 g/cm (800 g/in) and/or greater than about 354 g/cm (900 g/in) and/or greater than about 394 g/cm (1000 g/in) and/or from about 315 g/cm (800 g/in) to about 1968 g/cm (5000 g/in) and/or from about 354 g/cm (900 g/in) to about 1181 g/cm (3000 g/in) and/or from about 354 g/cm (900 g/in) to about 984 g/cm (2500 g/in) and/or from about 394 g/cm (1000 g/in) to about 787 g/cm (2000 g/in), specifically including all 0.1 g/cm increments between the recited ranges.

The paper towel products of the present disclosure may exhibit a total dry tensile strength of less than about 3000 g/25.4 mm and/or less than 2000 g/25.4 mm and/or less than 1875 g/25.4 mm and/or less than 1850 g/25.4 mm and/or less than 1800 g/25.4 mm and/or less than 1700 g/25.4 mm and/or less than 1600 g/25.4 mm and/or less than 1560 g/25.4 mm and/or from about 1500 g/25.4 mm to about 400 g/25.4 mm and/or to about 600 g/25.4 mm and/or to about 800 g/25.4 mm and/or to about 1000 g/25.4 mm, specifically including all 0.1 mm increments between the recited ranges. In addition, single-ply paper towel products of the present disclosure may exhibit a total dry tensile strength of less than about 1560 g/25.4 mm and/or less than 1500 g/25.4 mm and/or less than 1400 g/25.4 mm and/or from about 1300 g/25.4 mm to about 300 g/25.4 mm and/or 400 g/25.4 mm and/or to about 600 g/25.4 mm and/or to about 800 g/25.4 mm and/or to about 1000 g/25.4 mm, specifically including all 0.1 mm increments between the recited ranges.

The sanitary tissue products (e.g., toilet tissue products) of the present disclosure may exhibit a geometric mean peak elongation of greater than 10%, and/or greater than 15%, and/or greater than 20%, and/or greater than 25%, as measured according to the Dry Tensile Strength Test Method detailed herein.

The sanitary tissue products (e.g., toilet tissue products) of the present disclosure may exhibit a geometric mean dry tensile strength of greater than about 200 g/in, and/or greater than about 250 g/in, and/or greater than about 300 g/in, and/or greater than about 350 g/in, and/or greater than about 400 g/in, and/or greater than about 500 g/in, and/or greater than about 750 g/in, as measured according to the Dry Tensile Strength Test Method detailed herein.

The sanitary tissue products (e.g., toilet tissue products) of the present disclosure may exhibit a geometric mean modulus of less than about 20,000 g/cm, and/or less than about 15,000 g/cm, and/or less than about 10,000 g/cm, and/or less than about 5,000 g/cm, and/or less than about 3,000 g/cm, and/or less than about 1,500 g/cm, and/or less than about 1,200 g/cm, and/or between about 1,200 g/cm and about 0 g/cm, and/or between about 1,200 g/cm and about 700 g/cm, as measured according to the Dry Tensile Strength Test Method detailed herein.

The sanitary tissue products (e.g., toilet tissue products) of the present disclosure may exhibit a CD elongation of greater than about 8%, and/or greater than about 10%, and/or greater than about 12%, and/or greater than about 15%, and/or greater than about 20%, as measured according to the Dry Tensile Strength Test Method detailed herein. Further, the sanitary tissue products (e.g., toilet tissue products) of the present disclosure may exhibit a CD elongation of from about 8% to about 20%, or from about 10% to about 20%, or from about 10% to about 15%, as measured according to the Dry Tensile Strength Test Method detailed herein.

The sanitary tissue products (e.g., toilet tissue products) of the present disclosure may exhibit a dry burst of less than about 660 g, and/or from about 100 g to about 600 g, as measured according to the Dry Burst Test Method detailed herein. In another example, the sanitary tissue products (e.g., toilet tissue products) of the present disclosure may exhibit a dry burst of greater than about 100 g, and/or from about 100 g to about 1000 g, and/or from about 100 g to about 600 g, as measured according to the Dry Burst Test Method detailed herein.

The paper towel products of the present disclosure may exhibit a wet burst strength of greater than about 270 grams, in another form from about 290 g, about 300 g, or about 315 g to about 360 g, about 380 g, or about 400 g, specifically including all 0.1 g/cm increments between the recited ranges.

The toilet tissue products of the present disclosure may exhibit an initial total wet tensile strength of less than about 78 g/cm (200 g/in) and/or less than about 59 g/cm (150 g/in) and/or less than about 39 g/cm (100 g/in) and/or less than about 29 g/cm (75 g/in) and/or less than about 23 g/cm (60 g/in) and/or less than about 20 g/cm (50 g/in) and/or about less than about 16 g/cm (40 g/cm), specifically including all 0.1 g/cm increments between the recited ranges. In addition, the paper towel products of the present disclosure may exhibit an initial total wet tensile strength of greater than about 118 g/cm (300 g/in) and/or greater than about 157 g/cm (400 g/in) and/or greater than about 196 g/cm (500 g/in) and/or greater than about 236 g/cm (600 g/in) and/or greater than about 276 g/cm (700 g/in) and/or greater than about 315 g/cm (800 g/in) and/or greater than about 354 g/cm (900 g/in) and/or greater than about 394 g/cm (1000 g/in) and/or from about 118 g/cm (300 g/in) to about 1968 g/cm (5000 g/in) and/or from about 157 g/cm (400 g/in) to about 1181 g/cm (3000 g/in) and/or from about 196 g/cm (500 g/in) to about 984 g/cm (2500 g/in) and/or from about 196 g/cm (500 g/in) to about 787 g/cm (2000 g/in) and/or from about 196 g/cm (500 g/in) to about 591 g/cm (1500 g/in), specifically including all 0.1 g/cm increments between the recited ranges.

Furthermore, the paper towel products of present disclosure may exhibit an initial total wet tensile strength of less than about 800 g/25.4 mm and/or less than about 600 g/25.4 mm and/or less than about 450 g/25.4 mm and/or less than about 300 g/25.4 mm and/or less than about 225 g/25.4 mm, specifically including all 0.1 g/mm increments between the recited ranges.

The toilet tissue products of the present disclosure may exhibit a decayed initial total wet tensile strength at 30 minutes of less than about 39 g/cm (100 g/in) and/or less than about 30 g/cm (75 g/in) and/or less than about 20 g/cm (50 g/in) and/or less than about 16 g/cm (40 g/in) and/or less than about 12 g/cm (30 g/in) and/or less than about 8 g/cm (20 g/in) and/or less than about 4 g/cm (10 g/in).

The toilet tissue products of the present disclosure may exhibit a full sheet tensile strength of about 400 g to about 850 g, or about 500 g to about 750 g, or about 550 g to about 700 g, or about 600 g to about 700 g, or greater than 400 g, or greater than 500 g, or greater than 600 g, or greater than 700 g, or greater than 800 g, specifically including all 1.0 g increments between the recited ranges. The toilet tissue products of the present disclosure may exhibit a full sheet tensile strength of about 100 g/in to about 212.5 g/in, or about 125 g/in to about 187.5 g/in, or about 137.5 g/in to about 175 g/in, or about 150 g/in to about 175 g/in, or greater than 100 g/in, or greater than 125 g/in, or greater than 150 g/in, or greater than 175 g/in, or greater than 200 g/in, specifically including all 1.0 g/in increments between the recited ranges. Such toilet tissue products of the present disclosure include a shaped line of weakness as detailed herein.

The toilet tissue products of the present disclosure may exhibit a full sheet average trapezoidal tear force of about 8 g to about 20 g, or about 10 g to about 18 g, or about 11 g to about 17 g, or less than about 20 g, or less than about 18 g, or less than about 16 g, or less than about 14 g, or less than about 12 g, or less than about 10 g, specifically including all 0.1 g increments between the recited ranges. Such toilet tissue products of the present disclosure include a shaped line of weakness as detailed herein.

The toilet tissue products of the present disclosure may exhibit a Line of Weakness Performance Factor ("LWP Factor") of between about 7 to about 30, or between about 8 to about 25, or between about 9 to about 25, or between about 9.5 to about 25, or between about 10 to about 20, or between about 10 to about 18, or between about 11 to about 20, or between about 11 to about 18, or between about 11 to about 17; or greater than about 7, or greater than about 8, or greater than about 9, or greater than about 9.5, or greater than about 10, or greater than about 10.5, or greater than about 11, specifically including all 0.1 increments between the recited ranges. Such toilet tissue products of the present disclosure include a shaped line of weakness as detailed herein. As detailed below, the LWP Factor is calculated by dividing the full sheet tensile strength in units of g/in by the full sheet average trapezoidal tear strength.

In non-limiting examples, the following data in Tables 1, 2 and 3 was obtained:

Example 1

TABLE 1

| | Full Sheet Average Trapezoidal Tear Strength (g) | Full Sheet Tensile Strength (g) | Sheet Width (in) | LWP Factor |
|---|---|---|---|---|
| Toilet Tissue - Straight Line of Weakness | 21.8 | 693 | 3.94 | 8.1 |
| Toilet Tissue - Shaped Line of Weakness | 16.3 | 706 | 3.94 | 11.0 |

Example 2

TABLE 2

| | Full Sheet Average Trapezoidal Tear Strength (g) | Full Sheet Tensile Strength (g) | Sheet Width (in) | LWP Factor |
|---|---|---|---|---|
| Toilet Tissue - Straight Line of Weakness | 14.9 | 556 | 3.94 | 9.5 |
| Toilet Tissue - Shaped Line of Weakness | 11.3 | 700 | 3.94 | 15.7 |

Examples 3-6

TABLE 3

| | Full Sheet Average Trapezoidal Tear Strength (g) | Full Sheet Tensile Strength (g) | Sheet Width (in) | LWP Factor |
|---|---|---|---|---|
| Toilet Tissue - Shaped Line of Weakness | 11.9 | 465 | 3.92 | 10.0 |
| Toilet Tissue - Shaped Line of Weakness | 10.1 | 474 | 3.92 | 12.0 |
| Toilet Tissue - Shaped Line of Weakness | 13.6 | 538 | 3.92 | 10.1 |
| Toilet Tissue - Shaped Line of Weakness | 14.1 | 590 | 4.5 | 9.3 |

The rolled sanitary tissue products of the present disclosure may exhibit a roll compressibility of from about 0.5% to about 15%, or from about 1.0% to about 12.5% or from about 1.0% to about 8%, specifically including all 0.1 increments between the recited ranges. The rolled sanitary tissue products of the present disclosure may exhibit a roll compressibility of less than about 15% and/or less than about 12.5% and/or less than about 10% and/or less than about 8% and/or less than about 7% and/or less than about 6% and/or less than about 5% and/or less than about 4% and/or less than about 3%, or from about 15% to about 0%, and/or from about 15% to about 0.5%, and/or from about 15% to about 1%, specifically including all 0.1 increments between the recited ranges. The rolled sanitary tissue products of the present disclosure may exhibit a roll compressibility of from about 4% to about 10% and/or from about 4% to about 8% and/or from about 4% to about 7% and/or from about 4% to about 6%, specifically including all 0.1 increments between the recited ranges. Such rolled sanitary tissue products of the present disclosure are rolled sanitary tissue substrates that include a shaped line of weakness as detailed herein, and roll compressibility is measured according to the Percent Compressibility Test Method described herein.

The rolled sanitary tissue products of the present disclosure may exhibit a roll bulk of from about 4 cm³/g to about 30 cm³/g and/or from about 6 cm³/g to about 15 cm³/g, specifically including all 0.1 increments between the recited ranges. The rolled sanitary tissue products of the present disclosure may exhibit a roll bulk of greater than about 4 cm³/g, greater than about 5 cm³/g, greater than about 6 cm³/g, greater than about 7 cm³/g, greater than about 8 cm³/g, greater than about 9 cm³/g, greater than about 10 cm³/g and greater than about 12 cm³/g, and less than about 20 cm³/g, less than about 18 cm³/g, less than about 16 cm³/g, and/or less than about 14 cm³/g, specifically including all 0.1 increments between the recited ranges. Such rolled sanitary tissue products of the present disclosure are rolled sanitary tissue substrates that include a shaped line of weakness as detailed herein.

The rolled sanitary tissue products of the present disclosure may exhibit a roll bulk of greater than 4 cm³/g and a percent compressibility of less than 10% and/or a roll bulk of greater than 6 cm³/g and a percent compressibility of less than 8% and/or a roll bulk of greater than 8 cm³/g and a percent compressibility of less than 7%. Such rolled sanitary tissue products of the present disclosure are rolled sanitary tissue substrates that include a shaped line of weakness as detailed herein.

The rolled sanitary tissue products of the present disclosure may exhibit a roll firmness of from about 2.5 mm to about 15 mm and/or from about 3 mm to about 13 mm and/or from about 4 mm to about 10 mm, specifically including all 0.1 increments between the recited ranges. Such rolled sanitary tissue products of the present disclosure are rolled sanitary tissue substrates that include a shaped line of weakness as detailed herein.

The rolled sanitary tissue products of the present disclosure may exhibit a roll diameter of from about 3 in to about 12 in and/or from about 3.5 in to about 8 in and/or from about 4.5 in to about 6.5 in, specifically including all 0.1 increments between the recited ranges. The rolled sanitary tissue products of the present disclosure may exhibit a roll diameter of greater than 4 in, greater than 5 in, greater than 6 in, greater than 7 in and/or greater than 8 in, specifically including all 0.1 increments between the recited ranges. Such rolled sanitary tissue products of the present disclosure are rolled sanitary tissue substrates that include a shaped line of weakness as detailed herein.

The sanitary tissue products of the present disclosure may exhibit an average Free Fiber End value of greater than about 1.5, greater than about 3, greater than about 6, and/or greater than about 9, specifically including all 0.1 increments between the recited ranges. The sanitary tissue products of the present disclosure may exhibit an average Free Fiber End value of greater than about 1.5 and less than about 20, greater than 3 and less than about 15, and/or greater than about 6 and less than about 15. In some examples, the sanitary tissue products of the present disclosure may have a total perforation length of about 46.60 mm, a total non-perforation length of 56.66 mm, a total line of perforation length of 103.26 mm, and thus a Percent Perforation of 42.1%. The sanitary tissue products of the present disclosure may exhibit a Percent Perforation of between about 30% and about 60%, between about 40% and about 50%, and/or between about 42% and about 47%, specifically including all 0.1 increments between the recited ranges. Such sanitary tissue products of the present disclosure are sanitary tissue substrates that include a shaped line of weakness as detailed herein.

When the sanitary tissue products of the present disclosure are run on a converting line, the sanitary tissue may be run at a reliability percentage of greater than about 50%, greater than about 60%, greater than about 70%, greater than about 80%, greater than about 85%, greater than about 90%, greater than about 95%, and/or between about 50% and about 99%, between about 60% and about 99%, between about 70% and about 99%, between about 80% and about 99%, between about 90% and about 99%, or between about 95% and about 99%, specifically including all 1% increments between the recited ranges. The reliability percentage is determined for a production run of a given amount of time, for example, 8 hours, 10 hours, 12 hours, 15 hours, 20 hours, 24 hours, 2 days, 3 days, 5 days, etc. Reliability percentage may be calculated as follows:

$$\text{Reliability \%} = \frac{\text{Total amount of time converting machine is converting product during a set production run (min)}}{\text{Total length of time of the set production run (min)}}$$

Such sanitary tissue products of the present disclosure are rolled sanitary tissue substrates that include a shaped line of weakness as detailed herein.

When the sanitary tissue products of the present disclosure are run on a converting line, the sanitary tissue may be run at a speed of greater than about 500 ft/min, greater than about 600 ft/min, greater than about 700 ft/min, greater than about 800 ft/min, greater than about 900 ft/min, greater than about 1000 ft/min, greater than about 1100 ft/min, greater than about 1200 ft/min, greater than about 1300 ft/min, greater than about 1400 ft/min, greater than about 1500 ft/min, and/or between about 500 ft/min and about 1500 ft/min, or between about 1000 ft/min and about 1500 ft/min, specifically including all 1 ft/min increments between the recited ranges. Such rolled sanitary tissue products of the present disclosure are rolled sanitary tissue substrates that include a shaped line of weakness as detailed herein.

When the sanitary tissue products of the present disclosure are run on a converting line, the sanitary tissue may be run at a speed of greater than about 500 ft/min, greater than about 600 ft/min, greater than about 700 ft/min, greater than about 800 ft/min, greater than about 900 ft/min, greater than about 1000 ft/min, greater than about 1100 ft/min, greater than about 1200 ft/min, greater than about 1300 ft/min, greater than about 1400 ft/min, greater than about 1500 ft/min, and/or between about 500 ft/min and about 1500 ft/min, or between about 1000 ft/min and about 1500 ft/min, specifically including all 1 ft/min increments between the recited ranges, while simultaneously achieving a reliability percentage of greater than about 50%, greater than about 60%, greater than about 70%, greater than about 80%, greater than about 85%, greater than about 90%, greater than about 95%, and/or between about 50% and about 99%, between about 60% and about 99%, between about 70% and about 99%, between about 80% and about 99%, between about 90% and about 99%, or between about 95% and about 99%, specifically including all 1% increments between the recited ranges. Such rolled sanitary tissue products of the present disclosure are rolled sanitary tissue substrates that include a shaped line of weakness as detailed herein.

Methods:

Basis Weight Test Method for Toilet Tissue Samples

Basis weight of a fibrous structure and/or sanitary tissue product is measured on stacks of twelve usable units using a top loading analytical balance with a resolution of ±0.001 g. The balance is protected from air drafts and other disturbances using a draft shield. A precision cutting die, measuring 3.500 in ±0.007 in by 3.500 in ±0.007 in is used to prepare all samples.

Stack six usable units aligning any perforations or folds on the same side of stack. With a precision cutting die, cut the stack into squares. Select six more usable units of the sample; stack and cut in like manner Combine the two stacks to form a single stack twelve squares thick. Measure the mass of the sample stack and record the result to the nearest 0.001 g.

The Basis Weight is calculated in lbs/3000 ft$^2$ or g/m$^2$ as follows:

Basis Weight=(Mass of stack)/[(Area of 1 layer in stack)×(Number of layers)]

For example,

Basis Weight (lbs/3000 ft$^2$)=[[Mass of stack (g)/ 453.6 (g/lbs)]/[12.25 (in$^2$)/144 (in$^2$/ft$^2$)×12]]× 3000

Or,

Basis Weight (g/m$^2$)=Mass of stack (g)/[79.032 (cm$^2$)/10,000 (cm$^2$/m$^2$)×12]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

Basis Weight Test Method for Paper Towel Samples

Basis weight of a fibrous structure and/or sanitary tissue product is measured on stacks of twelve usable units using a top loading analytical balance with a resolution of ±0.001 g. The balance is protected from air drafts and other disturbances using a draft shield. A precision cutting die, measuring 4.000 in ±0.008 in by 4.000 in ±0.008 in is used to prepare all samples.

Stack eight usable units aligning any perforations or folds on the same side of stack. With a precision cutting die, cut the stack into squares. Measure the mass of the sample stack and record the result to the nearest 0.001 g.

The Basis Weight is calculated in lbs/3000 ft$^2$ or g/m$^2$ as follows:

Basis Weight=(Mass of stack)/[(Area of 1 layer in stack)×(Number of layers)]

For example,

Basis Weight (lbs/3000 ft$^2$)=[[Mass of stack (g)/ 453.6 (g/lbs)]/[16 (in$^2$)/144 (in$^2$/ft$^2$)×8]]×3000

Or,

Basis Weight (g/m$^2$)=Mass of stack (g)/[103.23 (cm$^2$)/10,000 (cm$^2$/m$^2$)×8]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

Caliper Test Method for Toilet Tissue and Paper Towel Samples

Caliper of a fibrous structure and/or sanitary tissue product is measured using a ProGage Thickness Tester (Thwing-Albert Instrument Company, West Berlin, N.J.) with a pressure foot diameter of 2.00 inches (area of 3.14 in$^2$) at a pressure of 95 g/in$^2$. Four (4) samples are prepared by cutting of a usable unit such that each cut sample is at least 2.5 inches per side, avoiding creases, folds, and obvious defects. An individual specimen is placed on the anvil with the specimen centered underneath the pressure foot. The foot is lowered at 0.03 in/sec to an applied pressure of 95 g/in$^2$. The reading is taken after 3 sec dwell time, and the foot is raised. The measure is repeated in like fashion for the remaining 3 specimens. The caliper is calculated as the average caliper of the four specimens and is reported in mils (0.001 in) to the nearest 0.1 mils.

Dry Tensile Strength Test Method for Toilet Tissue Samples

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the load cell. Both the movable (upper) and stationary (lower) pneumatic jaws are fitted with smooth stainless steel faced grips, with a design suitable for testing 1 inch wide sheet material (Thwing-Albert item #733GC). An air pressure of about 60 psi is supplied to the jaws.

Twenty usable units of fibrous structures are divided into four stacks of five usable units each. The usable units in each stack are consistently oriented with respect to machine direction (MD) and cross direction (CD). Two of the stacks are designated for testing in the MD and two for CD. Using a one inch precision cutter (Thwing Albert) take a CD stack and cut two, 1.00 in±0.01 in wide by at least 3.0 in long strips from each CD stack (long dimension in CD). Each strip is five usable unit layers thick and will be treated as a unitary specimen for testing. In like fashion cut the remaining CD stack and the two MD stacks (long dimension in MD) to give a total of 8 specimens (five layers each), four CD and four MD.

Program the tensile tester to perform an extension test, collecting force and extension data at an acquisition rate of 20 Hz as the crosshead raises at a rate of 4.00 in/min (10.16 cm/min) until the specimen breaks. The break sensitivity is set to 50%, i.e., the test is terminated when the measured force drops to 50% of the maximum peak force, after which the crosshead is returned to its original position.

Set the gage length to 2.00 inches. Zero the crosshead and load cell. Insert the specimen into the upper and lower open grips such that at least 0.5 inches of specimen length is contained each grip. Align specimen vertically within the upper and lower jaws, then close the upper grip. Verify specimen is aligned, then close lower grip. The specimen should be under enough tension to eliminate any slack, but less than 0.05 N of force measured on the load cell. Start the tensile tester and data collection. Repeat testing in like fashion for all four CD and four MD specimens.

Program the Software to Calculate the Following from the Constructed Force (g) Verses Extension (in) Curve:

Tensile Strength is the maximum peak force (g) divided by the product of the specimen width (1 in) and the number of usable units in the specimen (5), and then reported as W in to the nearest 1 g/in.

Adjusted Gage Length is calculated as the extension measured at 11.12 g of force (in) added to the original gage length (in).

Elongation is calculated as the extension at maximum peak force (in) divided by the Adjusted Gage Length (in) multiplied by 100 and reported as % to the nearest 0.1%.

Tensile Energy Absorption (TEA) is calculated as the area under the force curve integrated from zero extension to the extension at the maximum peak force (g*in), divided by the product of the adjusted Gage Length (in), specimen width (in), and number of usable units in the specimen (5). This is reported as $g*in/in^2$ to the nearest 1 $g*in/in^2$.

Replot the force (g) verses extension (in) curve as a force (g) verses strain curve. Strain is herein defined as the extension (in) divided by the Adjusted Gage Length (in).

Program the Software to Calculate the Following from the Constructed Force (g) Verses Strain Curve:

Tangent Modulus is calculated as the least squares linear regression using the first data point from the force (g) verses strain curve recorded after 190.5 g (38.1 g×5 layers) force and the 5 data points immediately preceding and the 5 data points immediately following it. This slope is then divided by the product of the specimen width (2.54 cm) and the number of usable units in the specimen (5), and then reported to the nearest 1 g/cm.

The Tensile Strength (g/in), Elongation (%), TEA ($g*in/in^2$) and Tangent Modulus (g/cm) are calculated for the four CD specimens and the four MD specimens. Calculate an average for each parameter separately for the CD and MD specimens.

Calculations:

Geometric Mean Tensile=Square Root of [MD Tensile Strength (g/in)×CD Tensile Strength (g/in)]

Geometric Mean Peak Elongation=Square Root of [MD Elongation (%)×CD Elongation (%)]

Geometric Mean TEA=Square Root of [MD TEA ($g*in/in^2$)×CD TEA ($g*in/in^2$)]

Geometric Mean Modulus=Square Root of [MD Modulus (g/cm)×CD Modulus (g/cm)]

Total Dry Tensile Strength (TDT)=MD Tensile Strength (g/in)+CD Tensile Strength (g/in)

Total TEA=MD TEA ($g*in/in^2$)+CD TEA ($g*in/in^2$)

Total Modulus=MD Modulus (g/cm)+CD Modulus (g/cm)

Tensile Ratio=MD Tensile Strength (g/in)/CD Tensile Strength (g/in)

Dry Tensile Strength Test Method for Paper Towel Samples

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the load cell. Both the movable (upper) and stationary (lower) pneumatic jaws are fitted with smooth stainless steel faced grips, with a design suitable for testing 1 inch wide sheet material (Thwing-Albert item #733GC). An air pressure of about 60 psi is supplied to the jaws.

Eight usable units of fibrous structures are divided into two stacks of four usable units each. The usable units in each stack are consistently oriented with respect to machine direction (MD) and cross direction (CD). One of the stacks is designated for testing in the MD and the other for CD. Using a one inch precision cutter (Thwing Albert) take a CD stack and cut one, 1.00 in ±0.01 in wide by at least 5.0 in long stack of strips (long dimension in CD). In like fashion cut the remaining stack in the MD (strip long dimension in MD), to give a total of 8 specimens, four CD and four MD strips. Each strip to be tested is one usable unit thick, and will be treated as a unitary specimen for testing.

Program the tensile tester to perform an extension test, collecting force and extension data at an acquisition rate of 20 Hz as the crosshead raises at a rate of 4.00 in/min (10.16 cm/min) until the specimen breaks. The break sensitivity is set to 50%, i.e., the test is terminated when the measured force drops to 50% of the maximum peak force, after which the crosshead is returned to its original position.

Set the gage length to 4.00 inches. Zero the crosshead and load cell. Insert the specimen into the upper and lower open grips such that at least 0.5 inches of specimen length is contained each grip. Align specimen vertically within the upper and lower jaws, then close the upper grip. Verify specimen is aligned, then close lower grip. The specimen should be under enough tension to eliminate any slack, but less than 0.05 N of force measured on the load cell. Start the tensile tester and data collection. Repeat testing in like fashion for all four CD and four MD specimens.

Program the Software to Calculate the Following from the Constructed Force (g) Verses Extension (in) Curve:

Tensile Strength is the maximum peak force (g) divided by the specimen width (1 in), and reported as W in to the nearest 1 g/in.

Adjusted Gage Length is calculated as the extension measured at 11.12 g of force (in) added to the original gage length (in).

Elongation is calculated as the extension at maximum peak force (in) divided by the Adjusted Gage Length (in) multiplied by 100 and reported as % to the nearest 0.1%.

Tensile Energy Absorption (TEA) is calculated as the area under the force curve integrated from zero extension to the extension at the maximum peak force (g*in), divided by the product of the adjusted Gage Length (in) and specimen width (in). This is reported as $g*in/in^2$ to the nearest 1 $g*in/in^2$.

Replot the force (g) verses extension (in) curve as a force (g) verses strain curve. Strain is herein defined as the extension (in) divided by the Adjusted Gage Length (in).

Program the Software to Calculate the Following from the Constructed Force (g) Verses Strain Curve:

Tangent Modulus is calculated as the least squares linear regression using the first data point from the force (g) verses strain curve recorded after 38.1 g force and the 5 data points immediately preceding and the 5 data points immediately following it. This slope is then divided by the specimen width (2.54 cm), and then reported to the nearest 1 g/cm.

The Tensile Strength (g/in), Elongation (%), TEA ($g*in/in^2$) and Tangent Modulus (g/cm) are calculated for the four CD specimens and the four MD specimens. Calculate an average for each parameter separately for the CD and MD specimens.

Calculations:

Geometric Mean Tensile=Square Root of [MD Tensile Strength (g/in)×CD Tensile Strength (g/in)]

Geometric Mean Peak Elongation=Square Root of [MD Elongation (%)×CD Elongation (%)]

Geometric Mean TEA=Square Root of [MD TEA (g*in/in$^2$)×CD TEA (g*in/in$^2$)]

Geometric Mean Modulus=Square Root of [MD Modulus (g/cm)×CD Modulus (g/cm)]

Total Dry Tensile Strength (TDT)=MD Tensile Strength (g/in)+CD Tensile Strength (g/in)

Total TEA=MD TEA (g*in/in$^2$)+CD TEA (g*in/in$^2$)

Total Modulus=MD Modulus (g/cm)+CD Modulus (g/cm)

Tensile Ratio=MD Tensile Strength (g/in)/CD Tensile Strength (g/in)

Dry Burst Test Method

The Dry Burst Test is run according to ISO 12625-9:2005, except for any deviations described below. Fibrous structure samples for each condition to be tested are cut to a size appropriate for testing, a minimum of five (5) samples for each condition to be tested are prepared.

A burst tester (Burst Tester Intelect-II-STD Tensile Test Instrument, Cat. No. 1451-24PGB available from Thwing-Albert Instrument Co., Philadelphia, Pa., or equivalent) is set up according to the manufacturer's instructions and the following conditions: Speed: 12.7 centimeters per minute; Break Sensitivity: 20 grams; and Peak Load: 2000 grams. The load cell is calibrated according to the expected burst strength.

A fibrous structure sample to be tested is clamped and held between the annular clamps of the burst tester and is subjected to increasing force that is applied by a 0.625 inch diameter, polished stainless steel ball upon operation of the burst tester according to the manufacturer's instructions. The burst strength is that force that causes the sample to fail.

The burst strength for each fibrous structure sample is recorded. An average and a standard deviation for the burst strength for each condition is calculated.

The Dry Burst is reported as the average and standard deviation for each condition to the nearest gram.

Wet Burst Test Method

"Wet Burst Strength" as used herein is a measure of the ability of a fibrous structure and/or a fibrous structure product incorporating a fibrous structure to absorb energy, when wet and subjected to deformation normal to the plane of the fibrous structure and/or fibrous structure product. The Wet Burst Test is run according to ISO 12625-9:2005, except for any deviations or modifications described below.

Wet burst strength may be measured using a Thwing-Albert Burst Tester Cat. No. 177 equipped with a 2000 g load cell commercially available from Thwing-Albert Instrument Company, Philadelphia, Pa., or an equivalent instrument.

Wet burst strength is measured by preparing four (4) multi-ply fibrous structure product samples for testing. First, condition the samples for two (2) hours at a temperature of 73° F.±2° F. (23° C.±1° C.) and a relative humidity of 50% (±2%). Take one sample and horizontally dip the center of the sample into a pan filled with about 25 mm of room temperature distilled water. Leave the sample in the water four (4) (±0.5) seconds. Remove and drain for three (3) (±0.5) seconds holding the sample vertically so the water runs off in the cross machine direction. Proceed with the test immediately after the drain step.

Place the wet sample on the lower ring of the sample holding device of the Burst Tester with the outer surface of the sample facing up so that the wet part of the sample completely covers the open surface of the sample holding ring. If wrinkles are present, discard the samples and repeat with a new sample. After the sample is properly in place on the lower sample holding ring, turn the switch that lowers the upper ring on the Burst Tester. The sample to be tested is now securely gripped in the sample holding unit. Start the burst test immediately at this point by pressing the start button on the Burst Tester. A plunger will begin to rise (or lower) toward the wet surface of the sample. At the point when the sample tears or ruptures, report the maximum reading. The plunger will automatically reverse and return to its original starting position. Repeat this procedure on three (3) more samples for a total of four (4) tests, i.e., four (4) replicates. Report the results as an average of the four (4) replicates, to the nearest gram.

Wet Tensile Test Method

The Wet Tensile Strength test method is utilized for the determination of the wet tensile strength of a fibrous structure product strip after soaking with water, using a tensile-strength-testing apparatus operating with a constant rate of elongation. The Wet Tensile Strength test is run according to ISO 12625-5:2005, except for any deviations or modifications described below. This method uses a vertical tensile-strength tester, in which a device that is held in the lower grip of the tensile-strength tester, called a Finch Cup, is used to achieve the wetting.

Using a one inch JDC precision sample cutter (Thwing Albert) cut six 1.00 in ±0.01 in wide strips from a fibrous structure product sheet in the machine direction (MD), and six strips in the cross machine direction (CD). An electronic tensile tester (Model 1122, Instron Corp., or equivalent) is used and operated at a crosshead speed of 1.0 inch (about 1.3 cm) per minute and a gauge length of 1.0 inch (about 2.5 cm). The two ends of the strip are placed in the upper jaws of the machine, and the center of the strip is placed around a stainless steel peg. The strip is soaked in distilled water at about 20° C. for the identified soak time, and then measured for peak tensile strength. Reference to a machine direction means that the sample being tested is prepared such that the length of the strip is cut parallel to the machine direction of manufacture of the product.

The MD and CD wet peak tensile strengths are determined using the above equipment and calculations in the conventional manner. The reported value is the arithmetic average of the six strips tested for each directional strength to the nearest 0.1 grams force. The total wet tensile strength for a given soak time is the arithmetic total of the MD and CD tensile strengths for that soak time. Initial total wet tensile strength ("ITWT") is measured when the paper has been submerged for 5±0.5 seconds. Decayed total wet tensile ("DTWT") is measured after the paper has been submerged for 30±0.5 minutes.

Full Sheet Tensile Strength Test Method for Toilet Tissue and Paper Towel Samples Elongation, Tensile Strength, TEA and Tangent Modulus are measured by or calculated from data generated by a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the load cell. Both the movable (upper) and stationary (lower) pneumatic jaws are fitted with smooth stainless steel faced grips, with a design suitable for testing the full width of one sheet material. For example, the Thwing-Albert item #734K grips are suitable for testing a sheet having about a four inch width. An air pressure of about 60 psi is supplied to the jaws.

Unless otherwise specified, all tests described herein, including those described in the detailed description, are conducted on samples that have been conditioned in a conditioned room at a temperature of 73° F.±2° F. (23° C.±1° C.) and a relative humidity of 50% (±2%) for 2 hours prior to the test. All tests are conducted in such conditioned room(s). All plastic and paper board packaging materials must be carefully removed from the paper samples prior to testing. If the sample is in roll form, remove at least the leading five sheets by unwinding and tearing off via the closest line of weakness, and discard before testing the sample. Do not test sheet samples with defects such as perforation skips, wrinkles, tears, incomplete perforations, holes, etc.

A full finished product width sheet sample of a paper towel or bath tissue product is cut so that a perforation line passes across the sheet parallel to each cut in the width dimension. More specifically, take two adjacent sheets separated by a line of weakness (comprising one or more perforations), and cut a test sample to include at least a portion of the two tissue sheets. The cuts should be made across the width of the sheet generally parallel to the line of perforation and equally about the line of perforation. For example, the first cut is made at least two inches above the line of weakness comprising perforations and another cut is made on the other side of the line of weakness at least two inches from the line of weakness comprising perforations. At all times the sample should be handled in such a manner that perforations are not damaged or weakened. The prepared sample is placed in the grips so that no part of the line of weakness is touching or inside the clamped grip faces. Further, the line of weakness should be generally parallel to the grips. Stated another way, if an imaginary line were drawn across the width of the sheet connecting the two points at which the line of weakness crosses the edge of the sheet, the imaginary line should be generally parallel to the longitudinal axis of the grips (i.e., perpendicular to the direction of elongation).

Program the tensile tester to perform an extension test, collecting force and extension data at an acquisition rate of 100 Hz as the crosshead raises at a rate of 4.00 in/min (10.16 cm/min) until the specimen breaks (i.e., when the test specimen is physically separated into two parts). The break sensitivity is set to 98%, i.e., the test is terminated when the measured force drops to <2% of the maximum peak force, after which the crosshead is returned to its original position.

Set the gage length to 2.0 inches. Zero the crosshead position and load cell. Insert the sheet sample into the upper and lower open grips such that at least 0.5 inches of sheet length is contained in each grip. Verify that the sheet sample is properly aligned, as previously discussed, and then close lower and upper grips. The sheet sample should be under enough tension to eliminate any slack, but less than 5 g of force measured on the load cell. Start the tensile tester and data collection.

The location of failure (break) should be the line of weakness. Each sample sheet should break completely at the line of weakness. The peak force to tear the line of weakness is reported in grams. If the location of the failure (break) is not the line of weakness, disregard the data and repeat the test with another sheet sample.

Adjusted Gage Length is calculated as the extension measured at 5 g of force (in) added to the original gage length (in).

Peak Tensile is calculated as the force at the maximum or peak force. The result is reported as the Full Sheet Tensile Strength value in units of either total grams force (g) to the nearest 1 g, or grams force (g) per sheet width (in), to the nearest 1 g/in.

Total Energy Absorption to Failure (TEA to Failure) is calculated as the area under the force curve integrated from zero extension to the extension at the "failure" point (g*in), divided by the product of the adjusted Gage Length (in) and sample width (in). The failure point is defined here as the extension when the tension force falls to 5% of the maximum peak force. This is reported with units of $g*in/in^2$ to the nearest 1 $g*in/in^2$.

Repeat the above mentioned steps for each sample sheet. Four sample sheets should be tested and the results from those four tests should be averaged to determine a reportable data point.

Full Sheet Average Trapezoidal Tear Force Test Method for Toilet Tissue and Paper Towel Samples The Full Sheet Average Trapezoidal Tearing Force test method is adapted from ASTM D4533/D4533M-15 to measure the average force required to tear across the entire width of the sheet of a perforated fibrous structure product. The nonparallel sides of an isosceles trapezoid, centered on a line of perforation across a fibrous structure product specimen, are clamped in parallel jaws of a constant rate of extension tensile testing machine. The separation of the jaws is continuously increased to initiate and propagate a tear along the line of perforation while the force is measured, and the average force is calculated.

An outline of an isosceles trapezoid is marked on a specimen of two adjacent sheets of a fibrous structure product, such that a perforation line is centered between the two nonparallel sides of the trapezoid. The trapezoid dimensions are shown in FIG. 1 of ASTM D4533/D4533M-15. The shorter (25 mm) parallel side of the trapezoid is aligned with a side edge of the specimen, as pictured, and the nonparallel lines are then drawn at the depicted dimensions, but extending across the entire width of the sheet. No preliminary cut is made at the edge of the specimen prior to testing.

The specimen is conditioned for at least 2 hours and tested in a room at constant temperature (23° C.±2° C.) and relative humidity (50%±2%).

The distance between the parallel grips is set at 25.0 mm. The pneumatic jaws are designed to hold the grips parallel throughout the test. The load cell is selected such that the forces measured occur between 15% and 85% of the full-scale load. The tensile tester is programed to perform an extension test, collecting force and extension data at an acquisition rate of 100 Hz as the crosshead raises at a rate of 300 mm/min. The crosshead position and load cell are zeroed.

The sample is secured in the tensile testing machine using grips having a width such that the entire width of the specimen is secured. The specimen is clamped along the nonparallel sides of the trapezoid so that the end edges of the grips are in line with the 25 mm long side of the trapezoid, and the center line of the perforation across the width is centered between the grips. The initial slope of the line perforation at the 25 mm edge should be parallel to the grips or sloped downward. The short edge is held taut, but measuring less than 5 grams force, and the remaining width of the specimen is allowed to lie in folds. The load cell is re-zeroed.

The test is started and force data is recorded as the tear is initiated and propagated along the line of perforation across the entire width of the fibrous structure product specimen until the two sheets are fully separated at which time data collection is stopped. If a specimen slips, or fails at a location other than along the line of perforation the data is discarded and another specimen tested.

All force data collected from the initiation of the tear to full separation of the specimen is averaged and the value recorded to the nearest 0.1 grams. Ten replicate specimen samples are prepared and tested in like fashion. The average of the ten replicates is calculated and reported as the Full Sheet Average Trapezoidal Tear Strength to the nearest 0.1 grams.

Line of Weakness Performance Factor

The Line of Weakness Performance Factor is calculated by taking the ratio of the Full Sheet Tensile Strength, in grams force (g) per sheet width (in), to the Full Sheet Average Trapezoidal Tear Strength. The factor is calculated according to the following equation and reported to the nearest 0.1 units:

$$LWP\ Factor = \frac{Full\ Sheet\ Tensile\ Strength\,(g/in)}{Full\ Sheet\ Average\ Trapezoidal\ Tear\ Strength(g)}$$

As defined by the above equation, the units for LWP Factor are (g/in)/g. However, the LWP Factor is reported, and referred to herein, as a unitless number.

Figure 9:
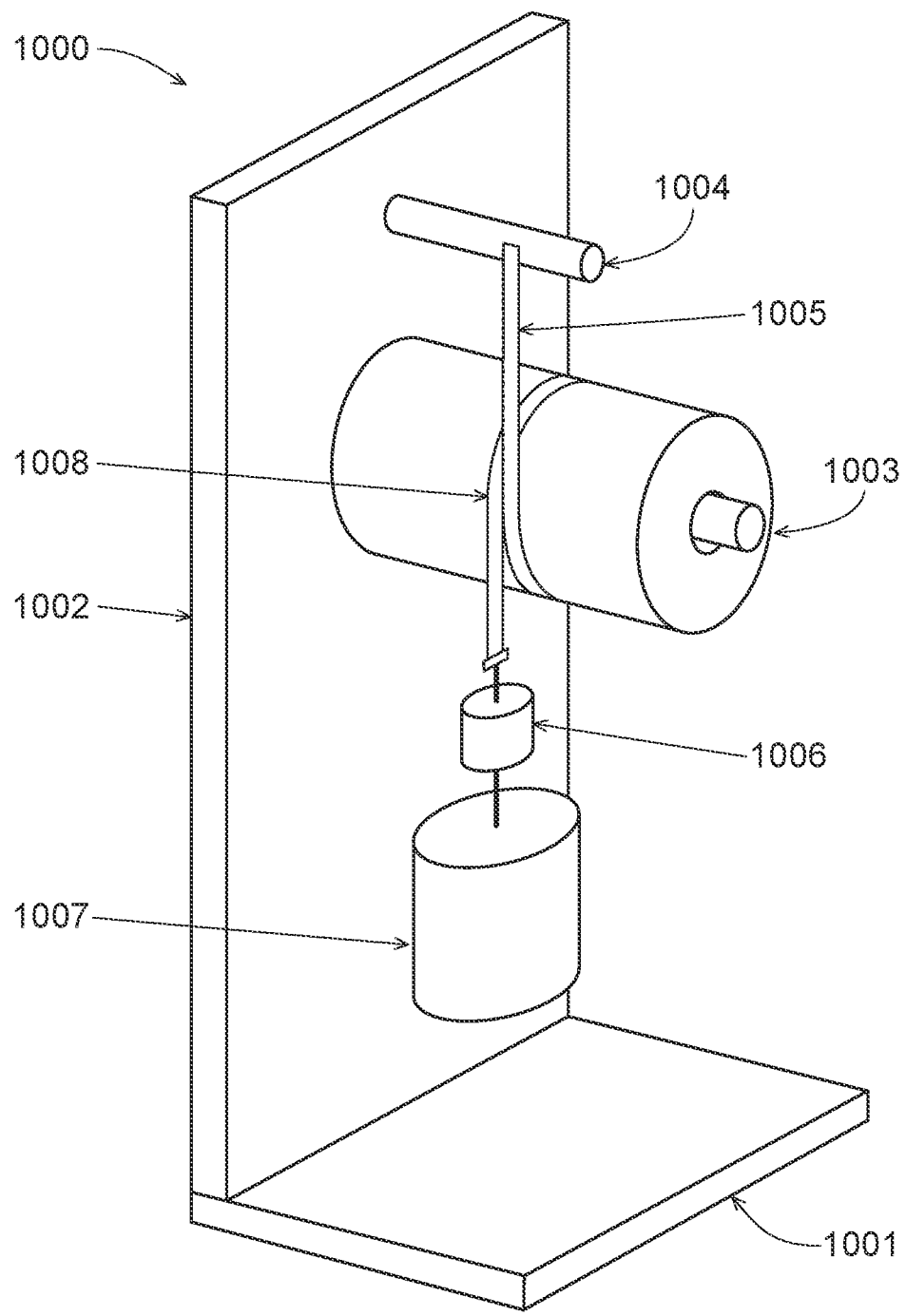
FIG. 9 is a schematic representation of the testing device used in the roll compressibility measurement.

Percent Compressibility Test Method for Toilet Tissue Roll and Paper Towel Roll Samples Percent Roll Compressibility (Percent Compressibility) is determined using the Roll Diameter Tester 1000 as shown in FIG. 9. It is comprised of a support stand made of two aluminum plates, a base plate 1001 and a vertical plate 1002 mounted perpendicular to the base, a sample shaft 1003 to mount the test roll, and a bar 1004 used to suspend a precision diameter tape 1005 that wraps around the circumference of the test roll. Two different weights 1006 and 1007 are suspended from the diameter tape to apply a confining force during the uncompressed and compressed measurement. All testing is performed in a conditioned room maintained at about 23° C.±2 C.° and about 50%±2% relative humidity.

The diameter of the test roll is measured directly using a Pi® tape or equivalent precision diameter tape (e.g. an Executive Diameter tape available from Apex Tool Group, LLC, Apex, N.C., Model No. W606PD) which converts the circumferential distance into a diameter measurement so the roll diameter is directly read from the scale. The diameter tape is graduated to 0.01 inch increments with accuracy certified to 0.001 inch and traceable to NIST. The tape is 0.25 in wide and is made of flexible metal that conforms to the curvature of the test roll but is not elongated under the 1100 g loading used for this test. If necessary the diameter tape is shortened from its original length to a length that allows both of the attached weights to hang freely during the test, yet is still long enough to wrap completely around the test roll being measured. The cut end of the tape is modified to allow for hanging of a weight (e.g. a loop). All weights used are calibrated, Class F hooked weights, traceable to NIST.

The aluminum support stand is approximately 600 mm tall and stable enough to support the test roll horizontally throughout the test. The sample shaft 1003 is a smooth aluminum cylinder that is mounted perpendicularly to the vertical plate 1002 approximately 485 mm from the base. The shaft has a diameter that is at least 90% of the inner diameter of the roll and longer than the width of the roll. A small steal bar 1004 approximately 6.3 mm diameter is mounted perpendicular to the vertical plate 1002 approximately 570 mm from the base and vertically aligned with the sample shaft. The diameter tape is suspended from a point along the length of the bar corresponding to the midpoint of a mounted test roll. The height of the tape is adjusted such that the zero mark is vertically aligned with the horizontal midline of the sample shaft when a test roll is not present.

Condition the samples at about 23° C.±2 C.° and about 50%±2% relative humidity for 2 hours prior to testing. Rolls with cores that are crushed, bent or damaged should not be tested. Place the test roll on the sample shaft 1003 such that the direction the paper was rolled onto its core is the same direction the diameter tape will be wrapped around the test roll. Align the midpoint of the roll's width with the suspended diameter tape. Loosely loop the diameter tape 1004 around the circumference of the roll, placing the tape edges directly adjacent to each other with the surface of the tape lying flat against the test sample. Carefully, without applying any additional force, hang the 100 g weight 1006 from the free end of the tape, letting the weighted end hang freely without swinging. Wait 3 seconds. At the intersection of the diameter tape 1008, read the diameter aligned with the zero mark of the diameter tape and record as the Original Roll Diameter to the nearest 0.01 inches. With the diameter tape still in place, and without any undue delay, carefully hang the 1000 g weight 1007 from the bottom of the 100 g weight, for a total weight of 1100 g. Wait 3 seconds. Again read the roll diameter from the tape and record as the Compressed Roll Diameter to the nearest 0.01 inch. Calculate percent compressibility to the according to the following equation and record to the nearest 0.1%:

$$\%\ Compressibility = \frac{(Original\ Roll\ Diameter) - (Compressed\ Roll\ Diameter)}{Original\ Roll\ Diameter} \times 100$$

Repeat the testing on 10 replicate rolls and record the separate results to the nearest 0.1%.

Average the 10 results and report as the Percent Compressibility to the nearest 0.1%.

Roll Firmness Test Method for Toilet Tissue Roll and Paper Towel Roll Samples

Roll Firmness is measured on a constant rate of extension tensile tester with computer interface (a suitable instrument is the MTS Alliance using Testworks 4.0 Software, as available from MTS Systems Corp., Eden Prairie, Minn.) using a load cell for which the forces measured are within 10% to 90% of the limit of the cell. The roll product is held horizontally, a cylindrical probe is pressed into the test roll, and the compressive force is measured versus the depth of penetration. All testing is performed in a conditioned room maintained at 23° C.±2C° and 50%±2% relative humidity.

Figure 10:
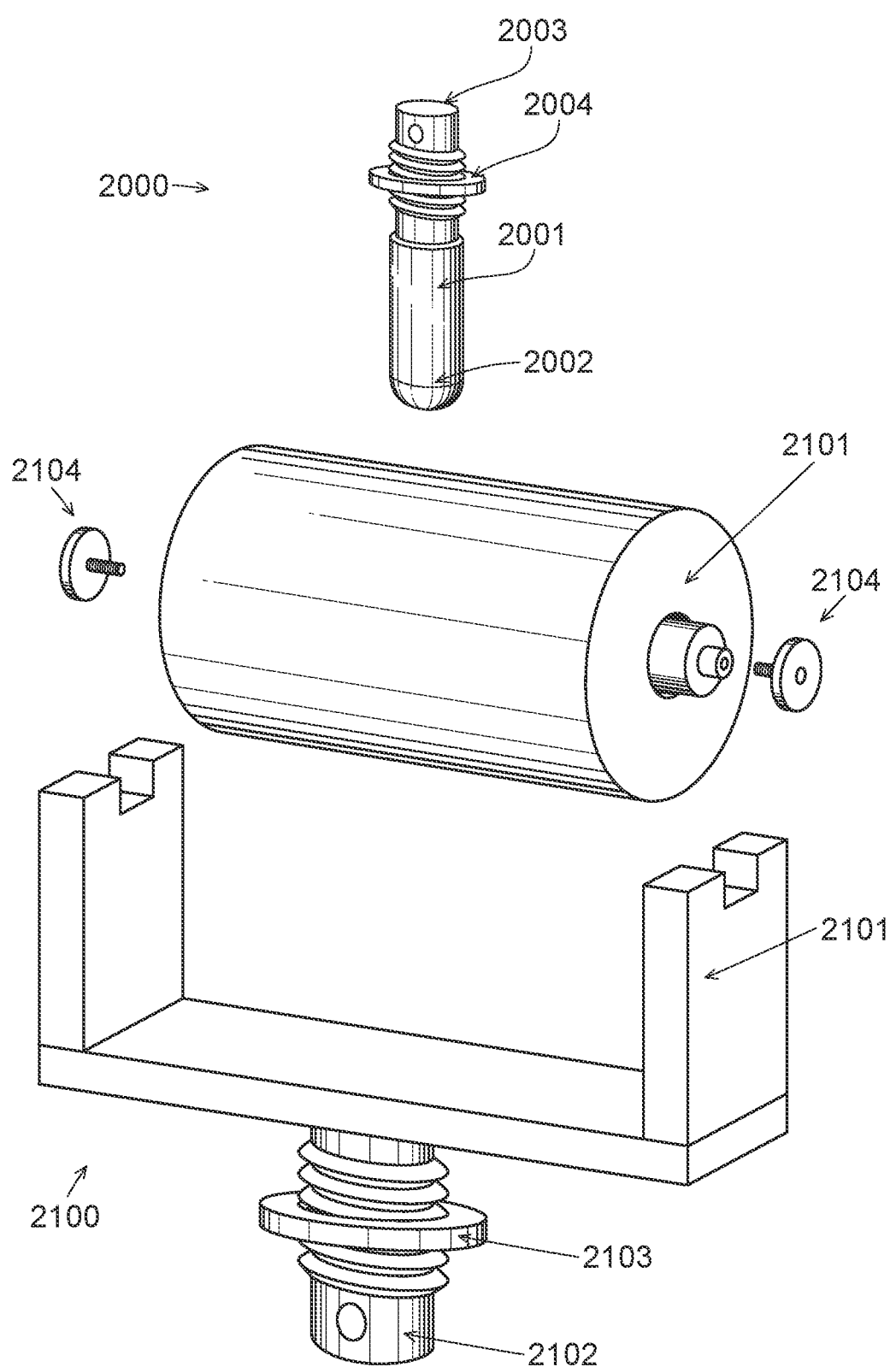
FIG. 10 is a schematic representation of the testing device used in the roll firmness measurement.

Referring to FIG. 10, the upper movable fixture 2000 consist of a cylindrical probe 2001 made of machined aluminum with a 19.00±0.05 mm diameter and a length of 38 mm. The end of the cylindrical probe 2002 is hemispheric (radius of 9.50±0.05 mm) with the opposing end 2003 machined to fit the crosshead of the tensile tester. The fixture includes a locking collar 2004 to stabilize the probe and maintain alignment orthogonal to the lower fixture. The lower stationary fixture 2100 is an aluminum fork with vertical prongs 2101 that supports a smooth aluminum sample shaft 2101 in a horizontal position perpendicular to the probe. The lower fixture has a vertical post 2102 machined to fit its base of the tensile tester and also uses a locking collar 2103 to stabilize the fixture orthogonal to the upper fixture.

The sample shaft 2101 has a diameter that is 85% to 95% of the inner diameter of the roll and longer than the width of the roll. The ends of sample shaft are secured on the vertical prongs with a screw cap 2104 to prevent rotation of the shaft during testing. The height of the vertical prongs 2101 should be sufficient to assure that the test roll does not contact the horizontal base of the fork during testing. The horizontal distance between the prongs must exceed the length of the test roll.

Program the tensile tester to perform a compression test, collecting force and crosshead extension data at an acquisition rate of 100 Hz. Lower the crosshead at a rate of 10 mm/min until 5.00 g is detected at the load cell. Set the current crosshead position as the corrected gage length and zero the crosshead position. Begin data collection and lower the crosshead at a rate of 50 mm/min until the force reaches 10 N. Return the crosshead to the original gage length.

Remove all of the test rolls from their packaging and allow them to condition at about 23° C.±2 C.° and about 50%±2% relative humidity for 2 hours prior to testing. Rolls with cores that are crushed, bent or damaged should not be tested. Insert sample shaft through the test roll's core and then mount the roll and shaft onto the lower stationary fixture. Secure the sample shaft to the vertical prongs then align the midpoint of the roll's width with the probe. Orient the test roll's tail seal so that it faces upward toward the probe. Rotate the roll 90 degrees toward the operator to align it for the initial compression.

Position the tip of the probe approximately 2 cm above the surface of the sample roll. Zero the crosshead position and load cell and start the tensile program. After the crosshead has returned to its starting position, rotate the roll toward the operator 120 degrees and in like fashion acquire a second measurement on the same sample roll.

From the resulting Force (N) verses Distance (mm) curves, read the penetration at 7.00 N as the Roll Firmness and record to the nearest 0.1 mm. In like fashion analyze a total of ten (10) replicate sample rolls. Calculate the arithmetic mean of the 20 values and report Roll Firmness to the nearest 0.1 mm Free Fiber End Measurement Method The Free Fiber End measurements are obtained from analysis of sample images acquired using a flatbed scanner of the torn line of perforation edge of fully separated fibrous structure product specimen sheets. The resulting image is then threshold, identifying the boundary along the perforation edge the sample containing the free fibers in a binary image, and the path length of the binary boundary along the perforation edge measured using an image analysis program. The ratio of the free fiber path length to the length of the actual line of perforation excluding any free fibers is calculated.

Sample Preparation

Samples for Free Fiber End measurement are obtained from the fully separated fibrous structure product specimen sheets remaining after completion of the Full Sheet Average Trapezoidal Tearing Force test.

Image Acquisition

Free Fiber End measurements are performed on images generated using a flatbed scanner capable of scanning in reflectance mode at a resolution of 6400 dpi and 8 bit grayscale (a suitable scanner is the Epson Perfection V750 Pro, Epson, USA). The scanner is interfaced with a computer running image analysis software (suitable image analysis software is ImageJ v. 1.46, National Institute of Health, USA). The sample images are distance calibrated against an acquired calibration image of a ruler certified by NIST at the same resolution as the sample image. The sample is scanned with a black glass tile (P/N 11-0050-30, available from HunterLab, Reston, Va.) as the background. The free fiber ends along the torn line of perforation edge in the scanned sample image are measured using the image analysis software. All testing is performed in a conditioned room maintained at about 23±2° C. and about 50±2% relative humidity.

Lay the sample flat onto the center of the scanner bed, and place the black glass tile on top of the sample covering it completely. Orient the sample so that the torn line of perforation edge is aligned generally parallel with and perpendicular to the sides of the scanner's glass surface. Close the lid and acquire a scanned image of the entire torn line of perforation edge in reflectance mode at a resolution of 6400 dpi (~4 μm/pixel) and 8 bit grayscale. The resultant image will have the torn line of perforation edge centered across the entire field of view. Save the image as an uncompressed TIFF format file. In like fashion, scan the remaining four replicate samples.

Image Analysis

Open the calibration image file in the image analysis program and perform a linear distance calibration using the imaged ruler. This distance calibration scale will be applied to all subsequent specimen images prior to analysis. Open the sample image in the image analysis program. Threshold the image at an appropriate graylevel (GL) value to generate a binary image. The appropriate threshold value will segregate the sample region, with its free fibers along the torn line of perforation edge, from the black background, while maintaining the original dimensions of the free fibers. Initially, the binary image will display the regions containing the sample, those with graylevels above the threshold value as white (GL value of 0), and the regions containing the black background, those with graylevels below the threshold value as black (GL value of 255). Use the fill holes operation to fill in any voids within the black background region. Invert the image so that the sample region above the threshold value will now appear as black (GL value of 255), and those of the background as white (GL value of 0). Use the fill holes operation to fill in any voids within the sample region.

Using the image analysis software, measure the path length of the binary boundary along the perforation edge the sample containing the free fibers in the binary image. Calculate the ratio of the sample boundary length with the free fibers to the measured total line of perforation length excluding any free fibers as measured by the Perforation and Bond Area Length Measurement Method, and record this Free Fiber End value to the nearest 0.1 units. In like fashion, analyze the remaining four sample images. Calculate and report the average Free Fiber End values to the nearest 0.01 units for the five replicates.

Perforation and Bond Area Length Measurement Method

The perforation and bond area length measurements are obtained from analysis of sample images acquired using a flatbed scanner of the line of perforation across a fibrous structure product specimen sheet.

Sample Preparation

Samples for perforation and bond area length measurement are two adjacent sheets of a fibrous structure product fibrous structure product connected by a line of perforation. Do not test sheet samples with defects such as perforation skips, wrinkles, tears, incomplete perforations, holes, etc. At all times the sample should be handled in such a manner that perforations are not damaged or weakened.

Image Acquisition

Perforation and bond area length measurements are performed on images generated using a flatbed scanner capable of scanning in reflectance mode at a resolution of 6400 dpi and 8 bit grayscale (a suitable scanner is the Epson Perfection V750 Pro, Epson, USA). The scanner is interfaced with a computer running image analysis software (suitable image analysis software is ImageJ v. 1.46, National Institute of Health, USA). The sample images are distance calibrated against an acquired calibration image of a ruler certified by NIST at the same resolution as the sample image. The sample is scanned with a black glass tile (P/N 11-0050-30, available from HunterLab, Reston, Va.) as the background. The lengths of perforations and bond areas along the line of perforation in the sample image are measured using the image analysis software. All testing is performed in a conditioned room maintained at about 23±2° C. and about 50±2% relative humidity.

Lay the sample flat onto the center of the scanner bed, and place the black glass tile on top of the sample covering the line of perforation completely. Orient the sample so that the center of the line of perforation is aligned generally parallel with and perpendicular to the sides of the scanner's glass surface. Close the lid and acquire a scanned image of the entire line of perforation in reflectance mode at a resolution of 6400 dpi (~4 µm/pixel) and 8 bit grayscale. The resultant image will have the line of perforation centered across the entire field of view. Save the image as an uncompressed TIFF format file. In like fashion, scan four more replicate samples.

Image Analysis

Open the calibration image file in the image analysis program and perform a linear distance calibration using the imaged ruler. This distance calibration scale will be applied to all subsequent specimen images prior to analysis. Open the sample image in the image analysis program.

Using the image analysis software, measure the linear distance of each individual perforation along the line of perforation and record each of these perforation lengths to the nearest 0.1 mm Using the image analysis software, measure the linear distance of each individual bond area along the line of perforation and record each of these non-perforation lengths to the nearest 0.1 mm Sum all of the perforation lengths and record as the total perforation length to the nearest 0.1 mm Sum all of the bond area non-perforation lengths and record as the total non-perforation length to the nearest 0.1 mm Sum together the total perforation length and non-perforation length and record as the total line of perforation length to the nearest 0.1 mm Divide the total perforation length by the total line of perforation length and multiply by 100 and record as the percent perforation. Divide the total non-perforation length by the total line of perforation length and multiply by 100 and record as the percent bond area non-perforation. In like fashion, analyze the remaining four sample images. Calculate and report the average all perforation and bond area length measurements for the five replicates.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to this disclosure or that claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed:

1. A web of sanitary tissue comprising a shaped line of weakness, wherein the web of sanitary tissue exhibits a Line of Weakness Performance Factor (LWP Factor) of from about 7 to about 30, and a Full Sheet Average Trapezoidal Tear Strength of between about 8 g and about 20 g according to the Full Sheet Average Trapezoidal Tear Force Test Method.

2. The web of claim 1, wherein the web of sanitary tissue exhibits a LWP Factor of greater than about 10.

3. The web of claim 1, wherein the web of sanitary tissue exhibits a LWP Factor of between about 10 and about 20.

4. The web of claim 1, wherein the web of sanitary tissue exhibits a Basis Weight of from about 30 g/m$^2$ to about 90 g/m$^2$, as measured according to the Basis Weight Test Method.

5. The web of claim 1, wherein the web of sanitary tissue exhibits a Dry Burst of between about 100 g and about 1000 g, as measured according to the Dry Burst Test Method.

6. The web of claim 1, wherein the web of sanitary tissue is a through-dried fibrous structure.

7. The web of claim 1, wherein the web of sanitary tissue is an uncreped fibrous structure.

8. A web of sanitary tissue product comprising a shaped line of weakness, wherein the sanitary tissue product exhibits a Line of Weakness Performance Factor (LWP Factor) of from about 7 to about 30, and a Full Sheet Average Trapezoidal Tear Strength of between about 8 g and about 20 g, as measured by the Full Sheet Average Trapezoidal Tear Force Method, and an average Free Fiber End value of greater than about 1.5.

9. The web of claim 8, wherein the sanitary tissue product exhibits a LWP Factor of greater than about 10.

10. The web of claim 8, wherein the sanitary tissue product exhibits a LWP Factor of between about 10 and about 20.

11. The web of claim 8, wherein the sanitary tissue product exhibits a Basis Weight of from about 30 g/m$^2$ to about 90 g/m$^2$, as measured according to the Basis Weight Test Method.

12. The web of claim 8, wherein the sanitary tissue product exhibits a Dry Burst of between about 100 g and about 1000 g, as measured according to the Dry Burst Test Method.

13. The web of claim 8, wherein the sanitary tissue product exhibits a Full Sheet Tensile Strength of between about 400 g and about 850 g, as measured by the Full Sheet Tensile Strength Test Method.

14. A roll of sanitary tissue product comprising a shaped line of weakness having an amplitude of from about 0.1 inches to about 1 inch, wherein the roll of sanitary tissue product exhibits a roll compressibility of from about 2% to about 10%, and the sanitary tissue product and a Line of Weakness Performance Factor (LWP Factor) of from about 7 to about 30, and a Full Sheet Average Trapezoidal Tear Strength of between about 8 g and about 20 g according to the Full Sheet Average Trapezoidal Tear Force Test Method.

15. The roll of claim 14, wherein the roll of sanitary tissue product exhibits a roll compressibility of from about 4% to about 7%.

16. The roll of claim 14, wherein the toilet tissue exhibits a LWP Factor of between about 10 and about 20.

17. The roll of claim 14, wherein the sanitary tissue exhibits a Dry Burst of between about 100 g and about 1000 g, as measured according to the Dry Burst Test Method.

18. The roll of claim 14, wherein the sanitary tissue is a through-dried fibrous structure.

19. The roll of claim 14, wherein the sanitary tissue product exhibits a Basis Weight of from about 30 $g/m^2$ to about 90 $g/m^2$, as measured according to the Basis Weight Test Method.

20. The roll of claim 14, wherein the sanitary tissue product exhibits an average Free Fiber End value of greater than about 1.5.

* * * * *